United States Patent [19]

Andree et al.

[11] Patent Number: 5,681,794
[45] Date of Patent: *Oct. 28, 1997

[54] N-CYANOARYL-NITROGEN HETEROCYCLES

[75] Inventors: Roland Andree; Mark-Wilhelm Drewes, both of Langenfeld; Albrecht Marhold, Leverkusen; Hans-Joachim Santel, Leverkusen; Markus Dollinger, Leverkusen, all of Germany

[73] Assignee: Bayer Aktiengesellschaft, Leverkusen, Germany

[ * ] Notice: The term of this patent shall not extend beyond the expiration date of Pat. No. 5,593,945.

[21] Appl. No.: 316,618

[22] Filed: Sep. 30, 1994

Related U.S. Application Data

[63] Continuation-in-part of Ser. No. 289,071, Aug. 11, 1994, Pat. No. 5,593,945.

[30] Foreign Application Priority Data

Aug. 18, 1993 [DE] Germany .............. 43 27 743.8
Apr. 8, 1994 [DE] Germany .............. 44 12 079.6

[51] Int. Cl.$^6$ .............. C07D 239/54; C07D 239/557; C07D 409/04; A01N 43/54
[52] U.S. Cl. .............. 504/243; 544/309; 544/310; 544/311; 544/313; 544/314; 504/243
[58] Field of Search .............. 544/309, 310, 544/311, 313, 314; 504/243, 242

[56] References Cited

U.S. PATENT DOCUMENTS 5,084,084  1/1992  Satow et al. .............. 71/92

FOREIGN PATENT DOCUMENTS 438209  7/1991  European Pat. Off. .

OTHER PUBLICATIONS

March, Advance Org. Chem. 3rd Edition, (1987) p. 370.0–54, Acylation of Amines by Acyl Halides.

*Primary Examiner*—Mukund J. Shah
*Assistant Examiner*—Sabiha Qazi
*Attorney, Agent, or Firm*—Sprung Kramer Schaefer & Briscoe

[57] ABSTRACT

The invention relates to new N-cyanoaryl-nitrogen heterocycles of the general formula (I)

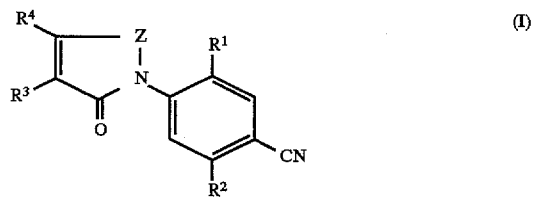

in which $R^1$, $R^2$, $R^3$, $R^4$ and Z have the meanings given in the description, to a plurality of processes for their preparation, to their use as herbicides and to novel intermediates.

32 Claims, No Drawings

N-CYANOARYL-NITROGEN HETEROCYCLES

This is a continuation-in-part of application Ser. No. 08/289,071, filed Aug. 11, 1994, now U.S. Pat. No. 5,593,945.

The invention relates to new N-cyanoaryl-nitrogen heterocycles, to a plurality of processes for their preparation, to their use as herbicides, and to new intermediates.

It has already been disclosed that certain N-cyanoaryl-nitrogen heterocycles have herbicidal properties (cf. WO 91/00278, WO 92/11244, DE 4237920, EP 408382/U.S. Pat. No. 5,084,084, EP 438209, EP 473551).

However, the herbicidal activity or the compatibility of the previously known N-cyanoaryl-nitrogen heterocycles with crop plants are not entirely satisfactory.

The new N-cyanoaryl-nitrogen heterocycles of the general formula (I)

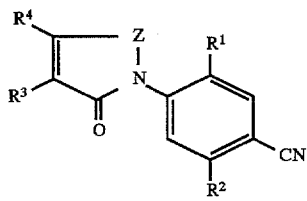

in which $R^1$ represents hydrogen or halogen, $R^2$ represents halogen, cyano, amino or the group $—N(A^1)S_2A$, where A represents in each case optionally substituted alkyl, alkenyl, alkinyl, cycloalkyl, cycloalkylalkyl, aryl, arylalkyl, heterocyclyl or heterocyclylalkyl, and $A^1$ represents hydrogen or optionally substituted alkyl, alkenyl, alkinyl, alkoxy, alkylcarbonyl, alkoxycarbonyl, arylcarbonyl, arylalkylcarbonyl or aryloxycarbonyl, $R^3$ represents hydrogen, halogen, cyano or optionally substituted alkyl, $R^4$ represents optionally substituted alkyl or together with $R^3$ represents alkanediyl, Z represents one of the groups below

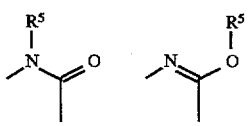

in which $R^5$ represents hydrogen, amino (bonded to N only) or in each case optionally substituted alkyl, alkenyl, alkinyl, alkylcarbonyl or alkoxycarbonyl, and their salts, the compounds 1-(4-cyano-3-ethylsulphonylamino-phenyl)-3,6-dihydro-2,6-dioxo-3-methyl-4-trifluoromethyl-1(2H)-pyrimidine, 1-(4-cyano-3-n-propyl-sulphonylamino-phenyl)-3,6-dihydro-2,6-dioxo-3-methyl-4-trifluoromethyl-1(2H)-pyrimidine, 1-(4-cyano-3-isopropylsulphonylamino-phenyl)-3,6-dihydro-2,6-dioxo-3-methyl-4-trifluoromethyl-1(2H)-pyrimidine, 1-(4-cyano-5-ethylsulphonylamino-2-fluoro-phenyl)-3,6-dihydro-2,6-dioxo-3-methyl-4-trifluoromethyl-1(2H)-pyrimidine, 1-(4-cyano-5-n-propylsulphonylamino-2-fluoro-phenyl)-3,6-dihydro-2,6-dioxo-3-methyl-4-trifluoromethyl-1(2H)-pyrimidine and 1-(4-cyano-5-isopropylsulphonylamino-2-fluoro-phenyl)-3,6-dihydro-2,6-dioxo-3-methyl-4-trifluoromethyl-1(2H)-pyrimidine—all disclosed in U.S. Pat. No. 5084084—being excepted by disclaimer, have now been found.

Thus, the general formula (I) represents the isomeric compounds of the general formulae (IA) and (IB) below

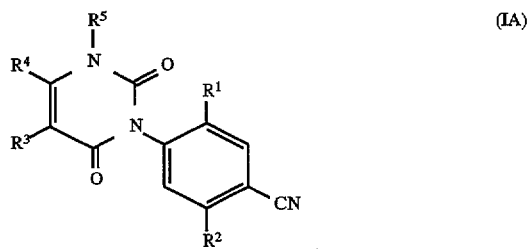

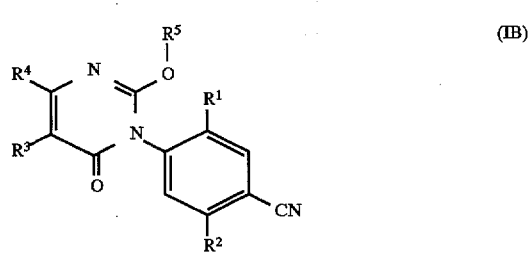

The new N-cyanoaryl-nitrogen heterocycles of the general formula (I) and salts thereof are obtained when, (a) to prepare compounds of the formulae (IA) and (IB) in which $R^5$ represents hydrogen and $R^1$, $R^2$, $R^3$ and $R^4$ have the abovementioned meanings, Aminoalkenoic esters of the general formula (II)

in which $R^3$ and $R^4$ have the abovementioned meanings and

R represents alkyl, aryl or arylalkyl are reacted with cyanoaryl isocyanates of the general formula (III)

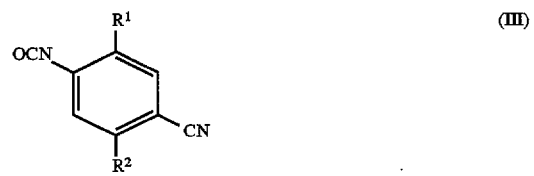

in which $R^1$ and $R^2$ have the abovementioned meanings, or with cyanoarylurethanes (cyanoaryl-carbamates) of the general formula (IV)

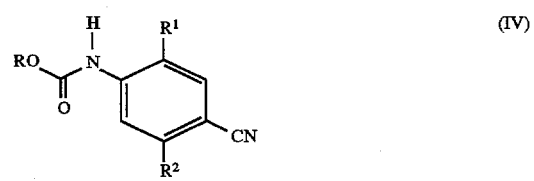

in which $R^1$ and $R^2$ have the abovementioned meanings and

R represents alkyl, aryl or arylalkyl, if appropriate in the presence of a reaction auxiliary and if appropriate in the presence of a diluent, or when, (b) to prepare compounds of the formulae (IA) and/or (IB) in which R⁵ represents in each case optionally substituted alkyl, alkenyl, alkinyl, alkylcarbonyl or alkoxycarbonyl and R¹, R², R³ and R⁴ have the abovementioned meanings, N-cyanoaryl-nitrogen heterocycles of the general formula (IA) or (IB)

in which R⁵ represents hydrogen and R¹, R², R³, and R⁴ have the abovementioned meanings, are reacted with alkylating agents or acylating agents of the general formula (V) or (VI)

X—R⁵                                                   (V)

R⁵—O—SO₂—O—R⁵                      (VI)

in which R⁵ represents in each case optionally substituted alkyl, alkenyl, alkinyl, alkylcarbonyl or alkoxycarbonyl and X in formula (V) represents halogen, if appropriate in the presence of an acid acceptor and if appropriate in the presence of a diluent, or when, (c) to prepare compounds of the formula (I) in which R² represents amino or the group —N(A¹)SO₂A and A, A¹, R¹, R³, R⁴ and Z have the abovementioned meanings, N-cyanoaryl-nitrogen heterocycles of the general formula (I) in which R² represents halogen and R¹, R³, R⁴ and Z have the abovementioned meanings, are reacted with ammonia or with amides of the general formula (VII)

HN(A¹)SO₂A                           (VII)

in which

A and A¹ have the abovementioned meanings, if appropriate in the presence of an acid acceptor and if appropriate in the presence of a diluent.

The compounds of the formula (IA) in which R⁵ represents amino can be prepared in a known manner by reacting corresponding compounds of the formula (IA), in which R⁵ represents hydrogen, with aminating agents, such as, for example, 1-aminooxy-2,4-dinitro-benzene (ADNB) in accordance with the equation below (cf. EP 476697, Example 4):

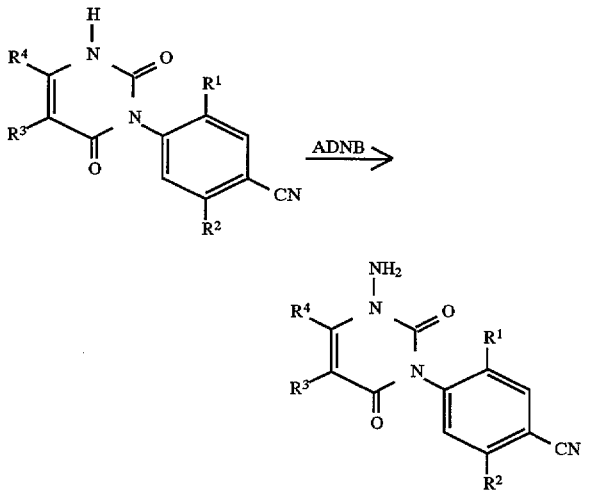

The new N-cyanoaryl-nitrogen heterocycles of the general formula (I) and salts thereof are distinguished by a powerful herbicidal activity.

In the definitions, the saturated or unsaturated hydrocarbon chains, such as alkyl, alkanediyl, alkenyl or alkinyl, are in each case straight chain or branched. Halogen generally represents fluorine, chlorine, bromine or iodine, preferably fluorine, chlorine or bromine, in particular fluorine or chlorine.

The invention preferably relates to compounds of the formula (I) in which

R¹ represents hydrogen, fluorine, chlorine or bromine,

R² represents fluorine, chlorine, bromine, cyano, amino or the group —N(A¹)SO₂A in which A represents a radical from the series comprising alkyl, alkenyl or alkinyl, each of which has up to 10 carbon atoms and each of which is optionally substituted by fluorine, chlorine, bromine, cyano or C₁-C₄-alkoxy, A furthermore represents cycloalkyl or cycloalkylalkyl, each of which has 3 to 8 carbon atoms in the cycloalkyl moiety and, if appropriate, 1 to 4 carbon atoms in the alkyl moiety and each of which is optionally substituted by fluorine, chlorine, bromine, cyano or C₁-C₄-alkyl, A furthermore represents aryl or arylalkyl, each of which has 6 or 10 carbon atoms in the aryl moiety and 1 to 4 carbon atoms in the alkyl moiety and each of which is optionally substituted by fluorine, chlorine, bromine, cyano, nitro, carboxyl, carbamoyl, by C₁-C₄-alkyl, C₁-C₄-alkoxy, C₁-C₄-alkylthio, C₁-C₄-alkylsulphinyl or C₁-C₄-alkylsulphonyl (each of which is optionally substituted by fluorine and/or chlorine), by dimethylaminosulphonyl or diethylaminosulphonyl, by C₁-C₄-alkoxycarbonyl (which is optionally substituted by fluorine, chlorine, bromine, methoxy or ethoxy), by phenyl, phenyloxy or phenylthio (each of which is optionally substituted by fluorine, chlorine, bromine, cyano, methyl, methoxy, trifluoromethyl and/or trifluoromethoxy), A furthermore represents heterocyclyl or heterocyclylalkyl, each of which has 2 to 6 carbon atoms and 1 to 4 nitrogen atoms and/or 1 or 2 oxygen or sulphur atoms in the saturated or unsaturated heterocyclyl moiety and optionally 1 to 4 carbon atoms in the alkyl moiety and each of which is optionally substituted by fluorine, chlorine, bromine, cyano, nitro, carboxyl, carbamoyl, by C₁-C₄-alkyl, C₁-C₄-alkoxy, C₁-C₄-alkylthio, C₁-C₄-alkylsulphinyl, C₁-C₄-alkylsulphonyl or C₁-C₄-alkoxycarbonyl (each of which is optionally substituted by fluorine and/or chlorine), by phenyl, phenoxy or phenylthio (each of which is optionally substituted by fluorine, chlorine, bromine, cyano, methyl, methoxy, trifluoromethyl and/or trifluoromethoxy), and A¹ represents hydrogen or alkyl, alkenyl, alkinyl, alkoxy, alkylcarbonyl or alkoxycarbonyl, each of which has up to 6 carbon atoms and each of which is optionally substituted by halogen or C₁-C₄-alkoxy, or represents phenylcarbonyl, naphthylcarbonyl, phenylmethylcarbonyl, naphthylmethylcarbonyl, phenoxycarbonyl or naphthyloxycarbonyl (each of which is optionally substituted by fluorine, chlorine, bromine, cyano, methyl, methoxy, trifluoromethyl and/or trifluoromethoxy), R³ represents hydrogen, fluorine, chlorine, bromine, cyano or alkyl having 1 to 6 carbon atoms which is optionally substituted by fluorine and/or chlorine, R⁴ represents alkyl having 1 to 6 carbon atoms which is optionally substituted by fluorine, chlorine, bromine, methoxy or ethoxy, or together with $R^3$ represents alkanediyl having 2 to 8 carbon atoms, and Z represents one of the groups below

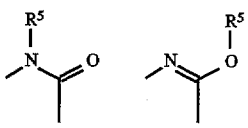

in which $R^5$ represents hydrogen or amino, or represents alkyl, alkenyl, alkinyl, alkylcarbonyl or alkoxycarbonyl, each of which has up to 6 carbon atoms and each of which is optionally substituted by fluorine, chlorine, bromine, cyano, $C_1$–$C_4$-alkoxy, $C_1$–$C_4$-alkylcarbonyl or $C_1$–$C_4$-alkoxy-carbonyl, and salts thereof with bases, such as, for example, sodium, potassium or calcium hydroxide, hydride, amide or carbonate, sodium or potassium $C_1$–$C_4$-alkanolates, ammonia, $C_1$–$C_4$-alkylamines, di-($C_1$–$C_4$-alkyl)-amines, tri-($C_1$–$C_4$-alkyl)-amines or with tris-(2-hydroxyethyl)amine, the abovementioned compounds being excepted.

The invention particularly relates to compounds of the formula (I) in which $R^1$ represents hydrogen, fluorine or chlorine, $R^2$ represents fluorine, chlorine, bromine, cyano, amino or the group —N($A^1$)$SO_2$A in which A represents methyl, ethyl, n- or i-propyl, n-, i-, s- or t-butyl or n-, i-, s- or t-pentyl, each of which is optionally substituted by fluorine or chlorine, A furthermore represents cyclopropyl, cyclobutyl, cyclopentyl, cyclohexyl, cyclopropylmethyl, cyclobutylmethyl, cyclopentylmethyl or cyclohexylmethyl, each of which is optionally substituted by fluorine, chlorine, bromine, methyl and/or ethyl, A furthermore represents phenyl, naphthyl, phenylmethyl or phenylethyl, each of which is optionally substituted by fluorine, chlorine, bromine, cyano, nitro, carboxy, methyl, trifluoromethyl, methoxy, ethoxy, difluoromethoxy, trifluoromethoxy, methylthio, ethylthio, methylsulphinyl, ethylsulphinyl, methylsulphonyl, ethylsulphonyl, dimethylaminosulphonyl, methoxycarbonyl, ethoxycarbonyl, propoxycarbonyl or phenyl, A furthermore represents thienyl, pyrazolyl or pyridyl, each of which is optionally substituted by fluorine, chlorine, bromine, cyano, methyl, ethyl, trifluoromethyl, methoxy, ethoxy, methylthio, ethylthio, methylsulphinyl, ethylsulphinyl, methylsulphonyl, ethylsulphonyl, methoxycarbonyl or ethoxycarbonyl, and $A^1$ represents hydrogen or methyl, ethyl, n- or i-propyl, n-, i- or s-butyl, propenyl, butenyl, propinyl, butinyl, methoxy, ethoxy, n- or i-propoxy, n-, i-, s- or t-butoxy, acetyl, propionyl, methoxycarbonyl or ethoxycarbonyl, each of which is optionally substituted by fluorine, chlorine, methoxy or ethoxy, or represents phenylcarbonyl or phenoxycarbonyl, $R^3$ represents hydrogen, fluorine, chlorine, bromine, methyl, trifluoromethyl, ethyl or n- or i-propyl, $R^4$ represents methyl, ethyl, n- or i-propyl, each of which is optionally substituted by fluorine or chlorine, or together with $R^3$ represents trimethylene or tetramethylene, and Z represents one of the groups below

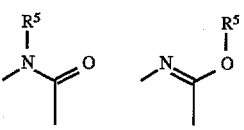

in which $R^5$ represents hydrogen, amino or methyl, ethyl, n- or i-propyl, n-, i- or s-butyl, propenyl, butenyl, propinyl, butinyl, acetyl, propionyl, methoxycarbonyl or ethoxycarbonyl, each of which is optionally substituted by fluorine, chlorine or cyano, and salts thereof with bases, such as, for example, sodium, potassium or calcium hydroxide, hydride, amide or carbonate, sodium or potassium $C_1$–$C_4$-alkanolates, ammonia, $C_1$–$C_4$-alkylamines, di-($C_1$–$C_4$-alkyl)-amines, tri-($C_1$–$C_4$-alkyl)-amines or with tris-(2-hydroxyethyl)amine, the above-mentioned compounds being excepted.

A very particularly preferred group of compounds of the formula (I) are those compounds of the formula (IA) in which $R^1$, $R^2$, $R^3$, $R^4$ and $R^5$ have the meaning given above as being particularly preferred.

The above-listed general radical definitions, or those given in preference ranges, apply both to the end products of the formula (I) and also, correspondingly, to the starting materials or intermediates required in each case for the preparation.

These radical definitions can be combined with each other as desired, that is to say combinations between the ranges of preferred compounds which have been given are also possible.

Examples of the compounds of the formula (I) according to the invention are listed in Table 1 below.

TABLE 1

Examples of the compounds of the Formula (I)

| $R^1$ | $R^2$ | $R^3$ | $R^4$ | $R^5$ |
|---|---|---|---|---|
| F | F | H | $CH_3$ | H |
| F | F | H | $CH_3$ | $CH_3$ |
| F | F | H | $CH_3$ | $CHF_2$ |
| F | F | H | $CH_3$ | $NH_2$ |
| F | $NHSO_2C_2H_5$ | H | $CH_3$ | $CH_3$ |
| F | $NHSO_2CH_3$ | H | $CH_3$ | $CHF_2$ |
| F | $NHSO_2CH_3$ | H | $CH_3$ | $NH_2$ |
| H | $NHSO_2CH_3$ | H | $CH_3$ | $NH_2$ |
| F | F | H | $CF_3$ | $CH_3$ |
| F | F | H | $CF_3$ | $C_3H_7$ |
| Cl | F | $CH_3$ | $CF_3$ | $CHF_2$ |
| F | $NHSO_2CH_3$ | H | $CF_3$ | $CH_3$ |
| F | $NHSO_2C_2H_5$ | H | $CF_3$ | $C_2H_5$ |
| F | $NHSO_2$—◁ | H | $CF_3$ | $CHF_2$ |
| F | $NHSO_2CH_3$ | H | $CF_3$ | $CH_2$—C≡CH |
| F | $NHSO_2C_2H_5$ | H | $CF_3$ | —◁ |
| F | $NHSO_2CH_3$ | H | $CF_3$ | $NH_2$ |
| F | $NHSO_2C_2H_5$ | H | $CH_2Cl$ | $CH_3$ |
| F | F | H | $CF_2CF_3$ | H |
| F | F | H | $CF_2CF_3$ | $CH_3$ |
| H | F | H | $CF_2CF_3$ | $C_2H_5$ |
| H | F | H | $CF_2CF_3$ | $CH_2CH=CH_2$ |

TABLE 1-continued

Examples of the compounds of the Formula (I)

| R¹ | R² | R³ | R⁴ | R⁵ |
|---|---|---|---|---|
| F | NHSO$_2$CH$_3$ | H | CF$_2$CF$_3$ | CH$_3$ |
| F | NHSO$_2$C$_2$H$_5$ | H | CF$_2$CF$_3$ | CH$_3$ |
| F | F | H | CHF$_2$ | H |
| F | F | H | CHF$_2$ | CH$_3$ |
| F | F | H | CHF$_2$ | CHF$_2$ |
| F | F | H | CHF$_2$ | NH$_2$ |
| F | NHSO$_2$CH$_3$ | H | CHF$_2$ | CH$_3$ |
| F | NHSO$_2$CH$_3$ | H | CHF$_2$ | CHF$_2$ |
| F | NHSO$_2$CH$_3$ | H | CHF$_2$ | NH$_2$ |
| F | NHSO$_2$C$_2$H$_5$ | Cl | CHF$_2$ | CH$_2$CH=CH$_2$ |
| F | NHSO$_2$CF$_3$ | H | CH$_3$ | CH$_3$ |
| F | NHSO$_2$CH$_3$ | H | CF$_3$ | H |
| F | NSO$_2$CH$_3$<br>\|<br>CH$_3$ | H | CF$_3$ | CH$_3$ |
| F | ⁻NSO$_2$CH$_3$ K⁺ | H | CF$_3$ | CH$_3$ |
| F | ⁻NSO$_2$C$_2$H$_5$ Na⁺ | H | CF$_3$ | CH$_3$ |
| F | ⁻NSO$_2$C$_3$H$_7$-n K⁺ | H | CF$_3$ | CH$_3$ |
| F | ⁻NSO$_2$C$_3$H$_7$-i Na⁺ | H | CF$_3$ | CH$_3$ |
| F | ⁻NSO$_2$CH$_3$ K⁺ | H | CF$_3$ | CH$_3$ |
| H | NHSO$_2$CH$_3$ | H | CH$_3$ | CH$_3$ |
| H | NHSO$_2$C$_2$H$_5$ | H | CH$_3$ | CH$_3$ |
| H | NHSO$_2$C$_3$H$_7$-n | H | CH$_3$ | CH$_3$ |
| H | NHSO$_2$C$_3$H$_7$-i | H | CH$_3$ | CH$_3$ |
| H | NHSO$_2$—◁ | H | CH$_3$ | CH$_3$ |
| H | NHSO$_2$C$_4$H$_9$-n | H | CH$_3$ | CH$_3$ |
| H | NHSO$_2$C$_6$H$_5$ | H | CH$_3$ | CH$_3$ |
| H | NHSO$_2$—⌬—CH$_3$ | H | CH$_3$ | CH$_3$ |
| F | NHSO$_2$CH$_3$ | H | CH$_3$ | CH$_3$ |
| F | NHSO$_2$C$_2$H$_5$ | H | CH$_3$ | CH$_3$ |
| F | NHSO$_2$C$_3$H$_7$-n | H | CH$_3$ | CH$_3$ |
| F | NHSO$_2$C$_3$H$_7$-i | H | CH$_3$ | CH$_3$ |
| F | NHSO$_2$—◁ | H | CH$_3$ | CH$_3$ |
| F | NHSO$_2$C$_4$H$_9$-n | H | CH$_3$ | CH$_3$ |
| F | NHSO$_2$C$_6$H$_5$ | H | CH$_3$ | CH$_3$ |
| F | NHSO$_2$—⌬—CH$_3$ | H | CH$_3$ | CH$_3$ |
| F | NHSO$_2$CH$_3$ | CH$_3$ | CH$_3$ | CH$_3$ |
| F | NHSO$_2$C$_2$H$_5$ | CH$_3$ | CH$_3$ | CH$_3$ |
| F | NHSO$_2$C$_3$H$_7$-n | CH$_3$ | CH$_3$ | CH$_3$ |
| F | NHSO$_2$C$_3$C$_7$-i | CH$_3$ | CH$_3$ | CH$_3$ |
| F | NHSO$_2$—◁ | CH$_3$ | CH$_3$ | CH$_3$ |
| F | NHSO$_2$C$_4$H$_9$-n | CH$_3$ | CH$_3$ | CH$_3$ |
| F | NHSO$_2$C$_6$H$_5$ | CH$_3$ | CH$_3$ | CH$_3$ |
| F | NHSO$_2$—⌬—CH$_3$ | CH$_3$ | CH$_3$ | CH$_3$ |
| F | NHSO$_2$CH$_3$ | Cl | CH$_3$ | CH$_3$ |
| F | NHSO$_2$C$_2$H$_5$ | Cl | CH$_3$ | CH$_3$ |
| F | NHSO$_2$C$_3$H$_7$-n | Cl | CH$_3$ | CH$_3$ |
| F | NHSO$_2$C$_3$H$_7$-i | Cl | CH$_3$ | CH$_3$ |
| F | NHSO$_2$—◁ | Cl | CH$_3$ | CH$_3$ |
| F | NHSO$_2$C$_4$H$_9$-n | Cl | CH$_3$ | CH$_3$ |
| F | NHSO$_2$C$_6$H$_5$ | Cl | CH$_3$ | CH$_3$ |
| F | NHSO$_2$—⌬—CH$_3$ | Cl | CH$_3$ | CH$_3$ |
| F | NHSO$_2$CH$_3$ | F | CH$_3$ | CH$_3$ |
| F | NHSO$_2$C$_2$H$_5$ | F | CH$_3$ | CH$_3$ |
| F | NHSO$_2$C$_3$H$_7$-n | F | CH$_3$ | CH$_3$ |
| F | NHSO$_2$C$_3$H$_7$-i | F | CH$_3$ | CH$_3$ |
| F | NHSO$_2$—◁ | F | CH$_3$ | CH$_3$ |
| F | NHSO$_2$C$_4$H$_9$-n | F | CH$_3$ | CH$_3$ |
| F | NHSO$_2$C$_6$H$_5$ | F | CH$_3$ | CH$_3$ |
| F | NHSO$_2$—⌬—CH$_3$ | F | CH$_3$ | CH$_3$ |
| H | NHSO$_2$CH$_3$ | H | CH$_3$ | CHF$_2$ |
| H | NHSO$_2$C$_2$H$_5$ | H | CH$_3$ | CHF$_2$ |
| H | NHSO$_2$C$_3$H$_7$-n | H | CH$_3$ | CHF$_2$ |
| H | NHSO$_2$C$_3$H$_7$-i | H | CH$_3$ | CHF$_2$ |
| H | NHSO$_2$—◁ | H | CH$_3$ | CHF$_2$ |
| H | NHSO$_2$C$_4$H$_9$-n | H | CH$_3$ | CHF$_2$ |
| H | NHSO$_2$C$_6$H$_5$ | H | CH$_3$ | CHF$_2$ |
| H | NHSO$_2$—⌬—CH$_3$ | H | CH$_3$ | CHF$_2$ |
| F | NHSO$_2$CH$_3$ | H | CH$_3$ | CHF$_2$ |
| F | NHSO$_2$C$_2$H$_5$ | H | CH$_3$ | CHF$_2$ |
| F | NHSO$_2$C$_3$H$_7$-n | H | CH$_3$ | CHF$_2$ |
| F | NHSO$_2$C$_3$H$_7$-i | H | CH$_3$ | CHF$_2$ |
| F | NHSO$_2$—◁ | H | CH$_3$ | CHF$_2$ |
| F | NHSO$_2$C$_4$H$_9$-n | H | CH$_3$ | CHF$_2$ |
| F | NHSO$_2$C$_6$H$_5$ | H | CH$_3$ | CHF$_2$ |
| F | NHSO$_2$—⌬—CH$_3$ | H | CH$_3$ | CHF$_2$ |
| F | NHSO$_2$CH$_3$ | CH$_3$ | CH$_3$ | CHF$_2$ |
| F | NHSO$_2$C$_2$H$_5$ | CH$_3$ | CH$_3$ | CHF$_2$ |
| F | NHSO$_2$C$_3$H$_7$-n | CH$_3$ | CH$_3$ | CHF$_2$ |
| F | NHSO$_2$C$_3$H$_7$-i | CH$_3$ | CH$_3$ | CHF$_2$ |
| F | NHSO$_2$—◁ | CH$_3$ | CH$_3$ | CHF$_2$ |
| F | NHSO$_2$C$_4$H$_9$-n | CH$_3$ | CH$_3$ | CHF$_2$ |
| F | NHSO$_2$C$_6$H$_5$ | CH$_3$ | CH$_3$ | CHF$_2$ |

TABLE 1-continued

Examples of the compounds of the Formula (I)

| R¹ | R² | R³ | R⁴ | R⁵ |
|---|---|---|---|---|
| F | NHSO₂-C₆H₄-CH₃ (p) | CH₃ | CH₃ | CHF₂ |
| F | NHSO₂CH₃ | Cl | CH₃ | CHF₂ |
| F | NHSO₂C₂H₅ | Cl | CH₃ | CHF₂ |
| F | NHSO₂C₃H₇-n | Cl | CH₃ | CHF₂ |
| F | NHSO₂C₃H₇-i | Cl | CH₃ | CHF₂ |
| F | NHSO₂-cyclopropyl | Cl | CH₃ | CHF₂ |
| F | NHSO₂C₄H₉-n | Cl | CH₃ | CHF₂ |
| F | NHSO₂C₆H₅ | Cl | CH₃ | CHF₂ |
| F | NHSO₂-C₆H₄-CH₃ (p) | Cl | CH₃ | CHF₂ |
| F | NHSO₂CH₃ | F | CH₃ | CHF₂ |
| F | NHSO₂C₂H₅ | F | CH₃ | CHF₂ |
| F | NHSO₂C₃H₇-n | F | CH₃ | CHF₂ |
| F | NHSO₂C₃H₇-i | F | CH₃ | CHF₂ |
| F | NHSO₂-cyclopropyl | F | CH₃ | CHF₂ |
| F | NHSO₂C₄H₉-n | F | CH₃ | CHF₂ |
| F | NHSO₂C₆H₅ | F | CH₃ | CHF₂ |
| F | NHSO₂-C₆H₄-CH₃ (p) | F | CH₃ | CHF₂ |
| F | NHSO₂CH₃ | H | CH₃ | C₂H₅ |
| F | NHSO₂C₂H₅ | H | CH₃ | C₂H₅ |
| F | NHSO₂C₃H₇-n | H | CH₃ | C₂H₅ |
| F | NHSO₂C₃H₇-i | H | CH₃ | C₂H₅ |
| F | NHSO₂-cyclopropyl | H | CH₃ | C₂H₅ |
| F | NHSO₂C₄H₉-n | H | CH₃ | C₂H₅ |
| F | NHSO₂C₆H₅ | H | CH₃ | C₂H₅ |
| F | NHSO₂-C₆H₄-CH₃ (p) | H | CH₃ | C₂H₅ |
| H | NHSO₂CH₃ | H | CH₃ | NH₂ |
| H | NHSO₂C₂H₅ | H | CH₃ | NH₂ |
| H | NHSO₂C₃H₇-n | H | CH₃ | NH₂ |
| H | NHSO₂C₃H₇-i | H | CH₃ | NH₂ |
| H | NHSO₂-cyclopropyl | H | CH₃ | NH₂ |
| H | NHSO₂C₄H₉-n | H | CH₃ | NH₂ |
| H | NHSO₂C₆H₅ | H | CH₃ | NH₂ |
| H | NHSO₂-C₆H₄-CH₃ (p) | H | CH₃ | NH₂ |
| F | NHSO₂CH₃ | H | CH₃ | NH₂ |
| F | NHSO₂C₂H₅ | H | CH₃ | NH₂ |
| F | NHSO₂C₃H₇-n | H | CH₃ | NH₂ |
| F | NHSO₂C₃H₇-i | H | CH₃ | NH₂ |
| F | NHSO₂-cyclopropyl | H | CH₃ | NH₂ |
| F | NHSO₂C₄H₉-n | H | CH₃ | NH₂ |
| F | NHSO₂C₆H₅ | H | CH₃ | NH₂ |
| F | NHSO₂-C₆H₄-CH₃ (p) | H | CH₃ | NH₂ |
| F | NHSO₂CH₃ | CH₃ | CH₃ | NH₂ |
| F | NHSO₂C₂H₅ | CH₃ | CH₃ | NH₂ |
| F | NHSO₂C₃H₇-n | CH₃ | CH₃ | NH₂ |
| F | NHSO₂C₃H₇-i | CH₃ | CH₃ | NH₂ |
| F | NHSO₂-cyclopropyl | CH₃ | CH₃ | NH₂ |
| F | NHSO₂C₄H₉-n | CH₃ | CH₃ | NH₂ |
| F | NHSO₂C₆H₅ | CH₃ | CH₃ | NH₂ |
| F | NHSO₂-C₆H₄-CH₃ (p) | CH₃ | CH₃ | NH₂ |
| H | NHSO₂CH₃ | H | CF₃ | CH₃ |
| H | NHSO₂CF₃ | H | CF₃ | CH₃ |
| H | NHSO₂C₂H₅ | H | CF₃ | CH₃ |
| H | NHSO₂CH₂CF₃ | H | CF₃ | CH₃ |
| H | NHSO₂C₃H₇-n | H | CF₃ | CH₃ |
| H | NHSO₂C₃H₇-i | H | CF₃ | CH₃ |
| H | NHSO₂-cyclopropyl | H | CF₃ | CH₃ |
| H | NHSO₂CH₂CH₂CH₂Cl | H | CF₃ | CH₃ |
| H | NHSO₂C₄H₉-n | H | CF₃ | CH₃ |
| H | NHSO₂C₄H₉-sec | H | CF₃ | CH₃ |
| H | NHSO₂C₄H₉-iso | H | CF₃ | CH₃ |
| H | NHSO₂C₅H₁₀-n | H | CF₃ | CH₃ |
| H | NHSO₂-C₆H₅ | H | CF₃ | CH₃ |
| H | NHSO₂-C₆H₄-CH₃ (p) | H | CF₃ | CH₃ |
| H | NHSO₂-C₆H₄-Cl (p) | H | CF₃ | CH₃ |
| F | NHSO₂CH₃ | H | CF₃ | CH₃ |
| F | NHSO₂CF₃ | H | CF₃ | CH₃ |
| F | NHSO₂C₂H₅ | H | CF₃ | CH₃ |
| F | NHSO₂CH₂CF₃ | H | CF₃ | CH₃ |
| F | NHSO₂C₃H₇-n | H | CF₃ | CH₃ |
| F | NHSO₂C₃H₇-i | H | CF₃ | CH₃ |
| F | NHSO₂-cyclopropyl | H | CF₃ | CH₃ |
| F | NHSO₂CH₂CH₂CH₂Cl | H | CF₃ | CH₃ |
| F | NHSO₂C₄H₉-n | H | CF₃ | CH₃ |

TABLE 1-continued

Examples of the compounds of the Formula (I)

| $R^1$ | $R^2$ | $R^3$ | $R^4$ | $R^5$ |
|---|---|---|---|---|
| F | NHSO$_2$C$_4$H$_9$-sec | H | CF$_3$ | CH$_3$ |
| F | NHSO$_2$C$_4$H$_9$-iso | H | CF$_3$ | CH$_3$ |
| F | NHSO$_2$C$_5$H$_{10}$-n | H | CF$_3$ | CH$_3$ |
| F | NHSO$_2$—C$_6$H$_5$ | H | CF$_3$ | CH$_3$ |
| F | NHSO$_2$—C$_6$H$_4$—CH$_3$ | H | CF$_3$ | CH$_3$ |
| F | NHSO$_2$—C$_6$H$_4$—Cl | H | CF$_3$ | CH$_3$ |
| H | N(CH$_3$)—SO$_2$CH$_3$ | H | CF$_3$ | CH$_3$ |
| H | N(CH$_3$)—SO$_2$CF$_3$ | H | CF$_3$ | CH$_3$ |
| H | N(CH$_3$)—SO$_2$C$_2$H$_5$ | H | CF$_3$ | CH$_3$ |
| H | N(CH$_3$)—SO$_2$CH$_2$CF$_3$ | H | CF$_3$ | CF$_3$ |
| H | N(CH$_3$)—SO$_2$C$_3$H$_7$-n | H | CF$_3$ | CH$_3$ |
| H | N(CH$_3$)—SO$_2$C$_3$H$_7$-i | H | CF$_3$ | CH$_3$ |
| H | N(CH$_3$)—SO$_2$-cyclopropyl | H | CF$_3$ | CH$_3$ |
| H | N(CH$_3$)—SO$_2$CH$_2$CH$_2$CH$_2$Cl | H | CF$_3$ | CH$_3$ |
| H | N(CH$_3$)—SO$_2$C$_4$H$_9$-n | H | CF$_3$ | CH$_3$ |
| H | N(CH$_3$)—SO$_2$C$_4$H$_9$-sec | H | CF$_3$ | CH$_3$ |
| H | N(CH$_3$)—SO$_2$C$_4$H$_9$-iso | H | CF$_3$ | CH$_3$ |
| H | N(CH$_3$)—SO$_2$C$_5$H$_{10}$-n | H | CF$_3$ | CH$_3$ |
| H | N(CH$_3$)—SO$_2$—C$_6$H$_5$ | H | CF$_3$ | CH$_3$ |
| H | N(CH$_3$)—SO$_2$—C$_6$H$_4$—CH$_3$ | H | CF$_3$ | CH$_3$ |
| H | N(CH$_3$)—SO$_2$—C$_6$H$_4$—Cl | H | CF$_3$ | CH$_3$ |
| F | N(CH$_3$)—SO$_2$CH$_3$ | H | CF$_3$ | CH$_3$ |
| F | N(CH$_3$)—SO$_2$CF$_3$ | H | CF$_3$ | CH$_3$ |
| F | N(CH$_3$)—SO$_2$C$_2$H$_5$ | H | CF$_3$ | CH$_3$ |
| F | N(CH$_3$)—SO$_2$CH$_2$CF$_3$ | H | CF$_3$ | CH$_3$ |
| F | N(CH$_3$)—SO$_2$C$_3$H$_7$-n | H | CF$_3$ | CH$_3$ |
| F | N(CH$_3$)—SO$_2$C$_3$H$_7$-i | H | CF$_3$ | CH$_3$ |
| F | N(CH$_3$)—SO$_2$-cyclopropyl | H | CF$_3$ | CH$_3$ |
| F | N(CH$_3$)—SO$_2$CH$_2$CH$_2$CH$_2$Cl | H | CF$_3$ | CH$_3$ |
| F | N(CH$_3$)—SO$_2$C$_4$H$_9$-n | H | CF$_3$ | CH$_3$ |
| F | N(CH$_3$)—SO$_2$C$_4$H$_9$-sec | H | CF$_3$ | CH$_3$ |
| F | N(CH$_3$)—SO$_2$C$_4$H$_9$-iso | H | CF$_3$ | CH$_3$ |
| F | N(CH$_3$)—SO$_2$C$_5$H$_{10}$-n | H | CF$_3$ | CH$_3$ |
| F | N(CH$_3$)—SO$_2$—C$_6$H$_5$ | H | CF$_3$ | CH$_3$ |
| F | N(CH$_3$)—SO$_2$—C$_6$H$_4$—CH$_3$ | H | CF$_3$ | CH$_3$ |
| F | N(CH$_3$)—SO$_2$—C$_6$H$_4$—Cl | H | CF$_3$ | CH$_3$ |
| H | N(C$_2$H$_5$)—SO$_2$CH$_3$ | H | CF$_3$ | CH$_3$ |
| H | N(C$_2$H$_5$)—SO$_2$CF$_3$ | H | CF$_3$ | CH$_3$ |

TABLE 1-continued

Examples of the compounds of the Formula (I)

| R¹ | R² | R³ | R⁴ | R⁵ |
|---|---|---|---|---|
| H | N(C₂H₅)—SO₂C₂H₅ | H | CF₃ | CH₃ |
| H | N(C₂H₅)—SO₂CH₂CF₃ | H | CF₃ | CH₃ |
| H | N(C₂H₅)—SO₂C₃H₇-n | H | CF₃ | CH₃ |
| H | N(C₂H₅)—SO₂C₃H₇-i | H | CF₃ | CH₃ |
| H | N(C₂H₅)—SO₂-cyclopropyl | H | CF₃ | CH₃ |
| H | N(C₂H₅)—SO₂CH₂CH₂CH₂Cl | H | CF₃ | CH₃ |
| H | N(C₂H₅)—SO₂C₄H₉-n | H | CF₃ | CH₃ |
| H | N(C₂H₅)—SO₂C₄H₉-sec | H | CF₃ | CH₃ |
| H | N(C₂H₅)—SO₂C₄H₉-iso | H | CF₃ | CH₃ |
| H | N(C₂H₅)—SO₂C₅H₁₀-n | H | CF₃ | CH₃ |
| H | N(C₂H₅)—SO₂—C₆H₅ | H | CF₃ | CH₃ |
| H | N(C₂H₅)—SO₂—C₆H₄—CH₃ | H | CF₃ | CH₃ |
| H | N(C₂H₅)—SO₂—C₆H₄—Cl | H | CF₃ | CH₃ |
| F | N(C₂H₅)—SO₂CH₃ | H | CF₃ | CH₃ |
| F | N(C₂H₅)—SO₂CF₃ | H | CF₃ | CH₃ |
| F | N(C₂H₅)—SO₂C₂H₅ | H | CF₃ | CH₃ |
| F | N(C₂H₅)—SO₂CH₂CF₃ | H | CF₃ | CH₃ |
| F | N(C₂H₅)—SO₂C₃H₇-n | H | CF₃ | CH₃ |
| F | N(C₂H₅)—SO₂C₃H₇-i | H | CF₃ | CH₃ |
| F | N(C₂H₅)—SO₂-cyclopropyl | H | CF₃ | CH₃ |
| F | N(C₂H₅)—SO₂CH₂CH₂CH₂Cl | H | CF₃ | CH₃ |
| F | N(C₂H₅)—SO₂C₄H₉-n | H | CF₃ | CH₃ |
| F | N(C₂H₅)—SO₂C₄H₉-sec | H | CF₃ | CH₃ |
| F | N(C₂H₅)—SO₂C₄H₉-iso | H | CF₃ | CH₃ |
| F | N(C₂H₅)—SO₂C₅H₁₀-n | H | CF₃ | CH₃ |
| F | N(C₂H₅)—SO₂—C₆H₅ | H | CF₃ | CH₃ |
| F | N(C₂H₅)—SO₂—C₆H₄—CH₃ | H | CF₃ | CH₃ |
| F | N(C₂H₅)—SO₂—C₆H₄—Cl | H | CF₃ | CH₃ |
| F | N(C₂H₅)—SO₂CH₃ | H | CF₃ | C₂H₅ |
| F | N(C₂H₅)—SO₂CF₃ | H | CF₃ | C₂H₅ |
| F | N(C₂H₅)—SO₂C₂H₅ | H | CF₃ | C₂H₅ |
| F | N(C₂H₅)—SO₂CH₂CF₃ | H | CF₃ | C₂H₅ |
| F | N(C₂H₅)—SO₂C₃H₇-n | H | CF₃ | C₂H₅ |
| F | N(C₂H₅)—SO₂C₃H₇-i | H | CF₃ | C₂H₅ |
| F | N(C₂H₅)—SO₂-cyclopropyl | H | CF₃ | C₂H₅ |
| F | N(C₂H₅)—SO₂CH₂CH₂CH₂Cl | H | CF₃ | C₂H₅ |

TABLE 1-continued

Examples of the compounds of the Formula (I)

| $R^1$ | $R^2$ | $R^3$ | $R^4$ | $R^5$ |
|---|---|---|---|---|
| F | $N(C_2H_5)-SO_2C_4H_9\text{-}n$ | H | $CF_3$ | $C_2H_5$ |
| F | $N(C_2H_5)-SO_2C_4H_9\text{-sec}$ | H | $CF_3$ | $C_2H_5$ |
| F | $N(C_2H_5)-SO_2C_4H_9\text{-iso}$ | H | $CF_3$ | $C_2H_5$ |
| F | $N(C_2H_5)-SO_2C_5H_{10}\text{-}n$ | H | $CF_3$ | $C_2H_5$ |
| F | $N(C_2H_5)-SO_2-C_6H_5$ | H | $CF_3$ | $C_2H_5$ |
| F | $N(C_2H_5)-SO_2-C_6H_4-CH_3$ | H | $CF_3$ | $C_2H_5$ |
| F | $N(C_2H_5)-SO_2-C_6H_4-Cl$ | H | $CF_3$ | $C_2H_5$ |
| H | $NHSO_2CH_3$ | H | $CF_3$ | $C_2H_5$ |
| H | $NHSO_2CF_3$ | H | $CF_3$ | $C_2H_5$ |
| H | $NHSO_2C_2H_5$ | H | $CF_3$ | $C_2H_5$ |
| H | $NHSO_2CH_2CF_3$ | H | $CF_3$ | $C_2H_5$ |
| H | $NHSO_2C_3H_7\text{-}n$ | H | $CF_3$ | $C_2H_5$ |
| H | $NHSO_2C_3H_7\text{-}i$ | H | $CF_3$ | $C_2H_5$ |
| H | $NHSO_2\text{-cyclopropyl}$ | H | $CF_3$ | $C_2H_5$ |
| H | $NHSO_2CH_2CH_2CH_2Cl$ | H | $CF_3$ | $C_2H_5$ |
| H | $NHSO_2C_4H_9\text{-}n$ | H | $CF_3$ | $C_2H_5$ |
| H | $NHSO_2C_4H_9\text{-sec}$ | H | $CF_3$ | $C_2H_5$ |
| H | $NHSO_2C_4H_9\text{-iso}$ | H | $CF_3$ | $C_2H_5$ |
| H | $NHSO_2C_5H_{10}\text{-}n$ | H | $CF_3$ | $C_2H_5$ |
| H | $NHSO_2-C_6H_5$ | H | $CF_3$ | $C_2H_5$ |
| H | $NHSO_2-C_6H_4-CH_3$ | H | $CF_3$ | $C_2H_5$ |
| H | $NHSO_2-C_6H_4-Cl$ | H | $CF_3$ | $C_2H_5$ |
| F | $NHSO_2CH_3$ | H | $CF_3$ | $C_2H_5$ |
| F | $NHSO_2CF_3$ | H | $CF_3$ | $C_2H_5$ |
| F | $NHSO_2C_2H_5$ | H | $CF_3$ | $C_2H_5$ |
| F | $NHSO_2CH_2CF_3$ | H | $CF_3$ | $C_2H_5$ |
| F | $NHSO_2C_3H_7\text{-}n$ | H | $CF_3$ | $C_2H_5$ |
| F | $NHSO_2C_3H_7\text{-}i$ | H | $CF_3$ | $C_2H_5$ |
| F | $NHSO_2\text{-cyclopropyl}$ | H | $CF_3$ | $C_2H_5$ |
| F | $NHSO_2CH_2CH_2CH_2Cl$ | H | $CF_3$ | $C_2H_5$ |
| F | $NHSO_2C_4H_9\text{-}n$ | H | $CF_3$ | $C_2H_5$ |
| F | $NHSO_2C_4H_9\text{-sec}$ | H | $CF_3$ | $C_2H_5$ |
| F | $NHSO_2C_4H_9\text{-iso}$ | H | $CF_3$ | $C_2H_5$ |
| F | $NHSO_2C_5H_{10}\text{-}n$ | H | $CF_3$ | $C_2H_5$ |
| F | $NHSO_2-C_6H_5$ | H | $CF_3$ | $C_2H_5$ |
| F | $NHSO_2-C_6H_4-CH_3$ | H | $CF_3$ | $C_2H_5$ |
| F | $NHSO_2-C_6H_4-Cl$ | H | $CF_3$ | $C_2H_5$ |
| H | $NHSO_2CH_3$ | $CH_3$ | $CF_3$ | $CH_3$ |
| H | $NHSO_2CF_3$ | $CH_3$ | $CF_3$ | $CH_3$ |
| H | $NHSO_2C_2H_5$ | $CH_3$ | $CF_3$ | $CH_3$ |
| H | $NHSO_2CH_2CF_3$ | $CH_3$ | $CF_3$ | $CH_3$ |
| H | $NHSO_2C_3H_7\text{-}n$ | $CH_3$ | $CF_3$ | $CH_3$ |
| H | $NHSO_2C_3H_7\text{-}i$ | $CH_3$ | $CF_3$ | $CH_3$ |
| H | $NHSO_2\text{-cyclopropyl}$ | $CH_3$ | $CF_3$ | $CH_3$ |
| H | $NHSO_2CH_2CH_2CH_2Cl$ | $CH_3$ | $CF_3$ | $CH_3$ |
| H | $NHSO_2C_4H_9\text{-}n$ | $CH_3$ | $CF_3$ | $CH_3$ |
| H | $NHSO_2C_4H_9\text{-sec}$ | $CH_3$ | $CF_3$ | $CH_3$ |
| H | $NHSO_2C_4H_9\text{-iso}$ | $CH_3$ | $CF_3$ | $CH_3$ |
| H | $NHSO_2C_5H_{10}\text{-}n$ | $CH_3$ | $CF_3$ | $CH_3$ |
| H | $NHSO_2-C_6H_5$ | $CH_3$ | $CF_3$ | $CH_3$ |
| H | $NHSO_2-C_6H_4-CH_3$ | $CH_3$ | $CF_3$ | $CH_3$ |
| H | $NHSO_2-C_6H_4-Cl$ | $CH_3$ | $CF_3$ | $CH_3$ |
| F | $NHSO_2CH_3$ | $CH_3$ | $CF_3$ | $CH_3$ |
| F | $NHSO_2CF_3$ | $CH_3$ | $CF_3$ | $CH_3$ |
| F | $NHSO_2C_2H_5$ | $CH_3$ | $CF_3$ | $CH_3$ |
| F | $NHSO_2CH_2CF_3$ | $CH_3$ | $CF_3$ | $CH_3$ |
| F | $NHSO_2C_3H_7\text{-}n$ | $CH_3$ | $CF_3$ | $CH_3$ |
| F | $NHSO_2C_3H_7\text{-}i$ | $CH_3$ | $CF_3$ | $CH_3$ |
| F | $NHSO_2\text{-cyclopropyl}$ | $CH_3$ | $CF_3$ | $CH_3$ |
| F | $NHSO_2CH_2CH_2CH_2Cl$ | $CH_3$ | $CF_3$ | $CH_3$ |
| F | $NHSO_2C_4H_9\text{-}n$ | $CH_3$ | $CF_3$ | $CH_3$ |
| F | $NHSO_2C_4H_9\text{-sec}$ | $CH_3$ | $CF_3$ | $CH_3$ |
| F | $NHSO_2C_4H_9\text{-iso}$ | $CH_3$ | $CF_3$ | $CH_3$ |
| F | $NHSO_2C_5H_{10}\text{-}n$ | $CH_3$ | $CF_3$ | $CH_3$ |
| F | $NHSO_2-C_6H_5$ | $CH_3$ | $CF_3$ | $CH_3$ |

TABLE 1-continued

Examples of the compounds of the Formula (I)

| R¹ | R² | R³ | R⁴ | R⁵ |
|---|---|---|---|---|
| F | NHSO₂—C₆H₄—CH₃ (p) | CH₃ | CF₃ | CH₃ |
| F | NHSO₂—C₆H₄—Cl (p) | CH₃ | CF₃ | CH₃ |
| F | NHSO₂CH₃ | Cl | CF₃ | CH₃ |
| F | NHSO₂CF₃ | Cl | CF₃ | CH₃ |
| F | NHSO₂C₂H₅ | Cl | CF₃ | CH₃ |
| F | NHSO₂CH₂CF₃ | Cl | CF₃ | CH₃ |
| F | NHSO₂C₃H₇-n | Cl | CF₃ | CH₃ |
| F | NHSO₂C₃H₇-i | Cl | CF₃ | CH₃ |
| F | NHSO₂—cyclopropyl | Cl | CF₃ | CH₃ |
| F | NHSO₂CH₂CH₂CH₂Cl | Cl | CF₃ | CH₃ |
| F | NHSO₂C₄H₉-n | Cl | CF₃ | CH₃ |
| F | NHSO₂C₄H₉-sec | Cl | CF₃ | CH₃ |
| F | NHSO₂C₄H₉-iso | Cl | CF₃ | CH₃ |
| F | NHSO₂C₅H₁₀-n | Cl | CF₃ | CH₃ |
| F | NHSO₂—C₆H₅ | Cl | CF₃ | CH₃ |
| F | NHSO₂—C₆H₄—CH₃ (p) | Cl | CF₃ | CH₃ |
| F | NHSO₂—C₆H₄—Cl (p) | Cl | CF₃ | CH₃ |
| F | NHSO₂CH₃ | F | CF₃ | CH₃ |
| F | NHSO₂CF₃ | F | CF₃ | CH₃ |
| F | NHSO₂C₂H₅ | F | CF₃ | CH₃ |
| F | NHSO₂CH₂CF₃ | F | CF₃ | CH₃ |
| F | NHSO₂C₃H₇-n | F | CF₃ | CH₃ |
| F | NHSO₂C₃H₇-i | F | CF₃ | CH₃ |
| F | NHSO₂—cyclopropyl | F | CF₃ | CH₃ |
| F | NHSO₂CH₂CH₂CH₂Cl | F | CF₃ | CH₃ |
| F | NHSO₂C₄H₉-n | F | CF₃ | CH₃ |
| F | NHSO₂C₄H₉-sec | F | CF₃ | CH₃ |
| F | NHSO₂C₄H₉-iso | F | CF₃ | CH₃ |
| F | NHSO₂C₅H₁₀-n | F | CF₃ | CH₃ |
| F | NHSO₂—C₆H₅ | F | CF₃ | CH₃ |
| F | NHSO₂—C₆H₄—CH₃ (p) | F | CF₃ | CH₃ |
| F | NHSO₂—C₆H₄—Cl (p) | F | CF₃ | CH₃ |
| F | N(CH₃)—SO₂CH₃ | CH₃ | CF₃ | CH₃ |
| F | N(CH₃)—SO₂CF₃ | CH₃ | CF₃ | CH₃ |
| F | N(CH₃)—SO₂C₂H₅ | CH₃ | CF₃ | CH₃ |
| F | N(CH₃)—SO₂CH₂CF₃ | CH₃ | CF₃ | CH₃ |
| F | N(CH₃)—SO₂C₃H₇-n | CH₃ | CF₃ | CH₃ |
| F | N(CH₃)—SO₂C₃H₇-i | CH₃ | CF₃ | CH₃ |
| F | N(CH₃)—SO₂—cyclopropyl | CH₃ | CF₃ | CH₃ |
| F | N(CH₃)—SO₂CH₂CH₂CH₂Cl | CH₃ | CF₃ | CH₃ |
| F | N(CH₃)—SO₂C₄H₉-n | CH₃ | CF₃ | CH₃ |
| F | N(CH₃)—SO₂C₄H₉-sec | CH₃ | CF₃ | CH₃ |
| F | N(CH₃)—SO₂C₄H₉-iso | CH₃ | CF₃ | CH₃ |
| F | N(CH₃)—SO₂C₅H₁₀-n | CH₃ | CF₃ | CH₃ |
| F | N(CH₃)—SO₂—C₆H₅ | CH₃ | CF₃ | CH₃ |
| F | N(CH₃)—SO₂—C₆H₄—CH₃ (p) | CH₃ | CF₃ | CH₃ |
| F | N(CH₃)—SO₂—C₆H₄—Cl (p) | CH₃ | CF₃ | CH₃ |
| F | N(CH₃)—SO₂CH₃ | Cl | CF₃ | CH₃ |
| F | N(CH₃)—SO₂CF₃ | Cl | CF₃ | CH₃ |
| F | N(CH₃)—SO₂C₂H₅ | Cl | CF₃ | CH₃ |

TABLE 1-continued

Examples of the compounds of the Formula (I)

| R¹ | R² | R³ | R⁴ | R⁵ |
|---|---|---|---|---|
| F | N(CH₃)—SO₂CH₂CF₃ | Cl | CF₃ | CH₃ |
| F | N(CH₃)—SO₂C₃H₇-n | Cl | CF₃ | CH₃ |
| F | N(CH₃)—SO₂C₃H₇-i | Cl | CF₃ | CH₃ |
| F | N(CH₃)—SO₂-cyclopropyl | Cl | CF₃ | CH₃ |
| F | N(CH₃)—SO₂CH₂CH₂CH₂Cl | Cl | CF₃ | CH₃ |
| F | N(CH₃)—SO₂C₄H₉-n | Cl | CF₃ | CH₃ |
| F | N(CH₃)—SO₂C₄H₉-sec | Cl | CF₃ | CH₃ |
| F | N(CH₃)—SO₂C₄H₉-iso | Cl | CF₃ | CH₃ |
| F | N(CH₃)—SO₂C₅H₁₀-n | Cl | CF₃ | CH₃ |
| F | N(CH₃)—SO₂—C₆H₅ | Cl | CF₃ | CH₃ |
| F | N(CH₃)—SO₂—C₆H₄—CH₃ | Cl | CF₃ | CH₃ |
| F | N(CH₃)—SO₂—C₆H₄—Cl | Cl | CF₃ | CH₃ |
| F | N(CH₃)—SO₂CH₃ | F | CF₃ | CH₃ |
| F | N(CH₃)—SO₂CF₃ | F | CF₃ | CH₃ |
| F | N(CH₃)—SO₂C₂H₅ | F | CF₃ | CH₃ |
| F | N(CH₃)—SO₂CH₂CF₃ | F | CF₃ | CH₃ |
| F | N(CH₃)—SO₂C₃H₇-n | F | CF₃ | CH₃ |
| F | N(CH₃)—SO₂C₃H₇-i | F | CF₃ | CH₃ |
| F | N(CH₃)—SO₂-cyclopropyl | F | CF₃ | CH₃ |
| F | N(CH₃)—SO₂CH₂CH₂CH₂Cl | F | CF₃ | CH₃ |
| F | N(CH₃)—SO₂C₄H₉-n | F | CF₃ | CH₃ |
| F | N(CH₃)—SO₂C₄H₉-sec | F | CF₃ | CH₃ |
| F | N(CH₃)—SO₂C₄H₉-iso | F | CF₃ | CH₃ |
| F | N(CH₃)—SO₂C₅H₁₀-n | F | CF₃ | CH₃ |
| F | N(CH₃)—SO₂—C₆H₅ | F | CF₃ | CH₃ |
| F | N(CH₃)—SO₂—C₆H₄—CH₃ | F | CF₃ | CH₃ |
| F | N(CH₃)—SO₂—C₆H₄—Cl | F | CF₃ | CH₃ |
| F | NHSO₂CH₃ | H | CF₃ | NH₂ |
| F | NHSO₂CF₃ | H | CF₃ | NH₂ |
| F | NHSO₂C₂H₅ | H | CF₃ | NH₂ |
| F | NHSO₂CH₂CF₃ | H | CF₃ | NH₂ |
| F | NHSO₂C₃H₇-n | H | CF₃ | NH₂ |
| F | NHSO₂C₃H₇-i | H | CF₃ | NH₂ |
| F | NHSO₂-cyclopropyl | H | CF₃ | NH₂ |
| F | NHSO₂CH₂CH₂CH₂Cl | H | CF₃ | NH₂ |
| F | NHSO₂C₄H₉-n | H | CF₃ | NH₂ |
| F | NHSO₂C₄H₉-sec | H | CF₃ | NH₂ |
| F | NHSO₂C₄H₉-iso | H | CF₃ | NH₂ |
| F | NHSO₂C₅H₁₀-n | H | CF₃ | NH₂ |
| F | NHSO₂—C₆H₅ | H | CF₃ | NH₂ |
| F | NHSO₂—C₆H₄—CH₃ | H | CF₃ | NH₂ |
| F | NHSO₂—C₆H₄—Cl | H | CF₃ | NH₂ |
| F | N(CH₃)—SO₂CH₃ | H | CF₃ | NH₂ |

TABLE 1-continued

Examples of the compounds of the Formula (I)

| R¹ | R² | R³ | R⁴ | R⁵ |
|---|---|---|---|---|
| F | N(CH₃)—SO₂CF₃ | H | CF₃ | NH₂ |
| F | N(CH₃)—SO₂C₂H₅ | H | CF₃ | NH₂ |
| F | N(CH₃)—SO₂C₃H₇-n | H | CF₃ | NH₂ |
| F | N(CH₃)—SO₂C₃H₇-i | H | CF₃ | NH₂ |
| F | N(CH₃)—SO₂-cyclopropyl | H | CF₃ | NH₂ |
| F | N(CH₃)—SO₂CH₂CH₂CH₂Cl | H | CF₃ | NH₂ |
| F | N(CH₃)—SO₂C₄H₉-n | H | CF₃ | NH₂ |
| F | N(CH₃)—SO₂C₄H₉-sec | H | CF₃ | NH₂ |
| F | N(CH₃)—SO₂C₄H₉-iso | H | CF₃ | NH₂ |
| F | N(CH₃)—SO₂C₅H₁₀-n | H | CF₃ | NH₂ |
| F | N(CH₃)—SO₂-C₆H₅ | H | CF₃ | NH₂ |
| F | N(CH₃)—SO₂-C₆H₄-CH₃ | H | CF₃ | NH₂ |
| F | N(CH₃)—SO₂-C₆H₄-Cl | H | CF₃ | NH₂ |
| F | NHSO₂CH₃ | CH₃ | CF₃ | NH₂ |
| F | NHSO₂CF₃ | CH₃ | CF₃ | NH₂ |
| F | NHSO₂C₂H₅ | CH₃ | CF₃ | NH₂ |
| F | NHSO₂CH₂CF₃ | CH₃ | CF₃ | NH₂ |
| F | NHSO₂C₃H₇-n | CH₃ | CF₃ | NH₂ |
| F | NHSO₂C₃H₇-i | CH₃ | CF₃ | NH₂ |
| F | NHSO₂-cyclopropyl | CH₃ | CF₃ | NH₂ |
| F | NHSO₂CH₂CH₂CH₂Cl | CH₃ | CF₃ | NH₂ |
| F | NHSO₂C₄H₉-n | CH₃ | CF₃ | NH₂ |
| F | NHSO₂C₄H₉-sec | CH₃ | CF₃ | NH₂ |
| F | NHSO₂C₄H₉-iso | CH₃ | CF₃ | NH₂ |
| F | NHSO₂C₅H₁₀-n | CH₃ | CF₃ | NH₂ |
| F | NHSO₂-C₆H₅ | CH₃ | CF₃ | NH₂ |
| F | NHSO₂-C₆H₄-CH₃ | CH₃ | CF₃ | NH₂ |
| F | NHSO₂-C₆H₄-Cl | CH₃ | CF₃ | NH₂ |
| F | NHSO₂CH₃ | H | CF₃ | CHF₂ |
| F | NHSO₂CF₃ | H | CF₃ | CHF₂ |
| F | NHSO₂C₂H₅ | H | CF₃ | CHF₂ |
| F | NHSO₂CH₂CF₃ | H | CF₃ | CHF₂ |
| F | NHSO₂C₃H₇-n | H | CF₃ | CHF₂ |
| F | NHSO₂C₃H₇-i | H | CF₃ | CHF₂ |
| F | NHSO₂-cyclopropyl | H | CF₃ | CHF₂ |
| F | NHSO₂CH₂CH₂CH₂Cl | H | CF₃ | CHF₂ |
| F | NHSO₂C₄H₉-n | H | CF₃ | CHF₂ |
| F | NHSO₂C₄H₉-sec | H | CF₃ | CHF₂ |
| F | NHSO₂C₄H₉-iso | H | CF₃ | CHF₂ |
| F | NHSO₂C₅H₁₀-n | H | CF₃ | CHF₂ |
| F | NHSO₂-C₆H₅ | H | CF₃ | CHF₂ |
| F | NHSO₂-C₆H₄-CH₃ | H | CF₃ | CHF₂ |
| F | NHSO₂-C₆H₄-Cl | H | CF₃ | CHF₂ |
| F | N(CH₃)—SO₂CH₃ | H | CF₃ | CHF₂ |
| F | N(CH₃)—SO₂CF₃ | H | CF₃ | CHF₂ |
| F | N(CH₃)—SO₂C₂H₅ | H | CF₃ | CHF₂ |
| F | N(CH₃)—SO₂CH₂CF₃ | H | CF₃ | CHF₂ |
| F | N(CH₃)—SO₂C₃H₇-n | H | CF₃ | CHF₂ |
| F | N(CH₃)—SO₂C₃H₇-i | H | CF₃ | CHF₂ |
| F | N(CH₃)—SO₂-cyclopropyl | H | CF₃ | CHF₂ |
| F | N(CH₃)—SO₂CH₂CH₂CH₂Cl | H | CF₃ | CHF₂ |

TABLE 1-continued

Examples of the compounds of the Formula (I)

| R¹ | R² | R³ | R⁴ | R⁵ |
|---|---|---|---|---|
| F | N(CH₃)—SO₂C₄H₉-n | H | CF₃ | CHF₂ |
| F | N(CH₃)—SO₂C₄H₉-sec | H | CF₃ | CHF₂ |
| F | N(CH₃)—SO₂C₄H₉-iso | H | CF₃ | CHF₂ |
| F | N(CH₃)—SO₂C₅H₁₀-n | H | CF₃ | CHF₂ |
| F | N(CH₃)—SO₂—C₆H₅ | H | CF₃ | CHF₂ |
| F | N(CH₃)—SO₂—C₆H₄—CH₃ | H | CF₃ | CHF₂ |
| F | N(CH₃)—SO₂—C₆H₄—Cl | H | CF₃ | CHF₂ |
| F | NHSO₂CH₃ | CH₃ | CF₃ | CHF₂ |
| F | NHSO₂CF₃ | CH₃ | CF₃ | CHF₂ |
| F | NHSO₂C₂H₅ | CH₃ | CF₃ | CHF₂ |
| F | NHSO₂CH₂CF₃ | CH₃ | CF₃ | CHF₂ |
| F | NHSO₂C₃H₇-n | CH₃ | CF₃ | CHF₂ |
| F | NHSO₂C₃H₇-i | CH₃ | CF₃ | CHF₂ |
| F | NHSO₂-cyclopropyl | CH₃ | CF₃ | CHF₂ |
| F | NHSO₂CH₂CH₂CH₂Cl | CH₃ | CF₃ | CHF₂ |
| F | NHSO₂C₄H₉-n | CH₃ | CF₃ | CHF₂ |
| F | NHSO₂C₄H₉-sec | CH₃ | CF₃ | CHF₂ |
| F | NHSO₂C₄H₉-iso | CH₃ | CF₃ | CHF₂ |
| F | NHSO₂C₅H₁₀-n | CH₃ | CF₃ | CHF₂ |
| F | NHSO₂—C₆H₅ | CH₃ | CF₃ | CHF₂ |
| F | NHSO₂—C₆H₄—CH₃ | CH₃ | CF₃ | CHF₂ |
| F | NHSO₂—C₆H₄—Cl | CH₃ | CF₃ | CHF₂ |
| H | NHSO₂CH₃ | H | CHF₂ | CH₃ |
| H | NHSO₂CF₃ | H | CHF₂ | CH₃ |
| H | NHSO₂C₂H₅ | H | CHF₂ | CH₃ |
| H | NHSO₂CH₂CF₃ | H | CHF₂ | CH₃ |
| H | NHSO₂C₃H₇-n | H | CHF₂ | CH₃ |
| H | NHSO₂C₃H₇-i | H | CHF₂ | CH₃ |
| H | NHSO₂-cyclopropyl | H | CHF₂ | CH₃ |
| H | NHSO₂CH₂CH₂CH₂Cl | H | CHF₂ | CH₃ |
| H | NHSO₂C₄H₉-n | H | CHF₂ | CH₃ |
| H | NHSO₂C₄H₉-sec | H | CHF₂ | CH₃ |
| H | NHSO₂C₄H₉-iso | H | CHF₂ | CH₃ |
| H | NHSO₂C₅H₁₀-n | H | CHF₂ | CH₃ |
| H | NHSO₂—C₆H₅ | H | CHF₂ | CH₃ |
| H | NHSO₂—C₆H₄—CH₃ | H | CHF₂ | CH₃ |
| H | NHSO₂—C₆H₄—Cl | H | CHF₂ | CH₃ |
| F | NHSO₂CH₃ | H | CHF₂ | CH₃ |
| F | NHSO₂CF₃ | H | CHF₂ | CH₃ |
| F | NHSO₂C₂H₅ | H | CHF₂ | CH₃ |
| F | NHSO₂CH₂CF₃ | H | CHF₂ | CH₃ |
| F | NHSO₂C₃H₇-n | H | CHF₂ | CH₃ |
| F | NHSO₂C₃H₇-i | H | CHF₂ | CH₃ |
| F | NHSO₂-cyclopropyl | H | CHF₂ | CH₃ |
| F | NHSO₂CH₂CH₂CH₂Cl | H | CHF₂ | CH₃ |
| F | NHSO₂C₄H₉-n | H | CHF₂ | CH₃ |
| F | NHSO₂C₄H₉-sec | H | CHF₂ | CH₃ |
| F | NHSO₂C₄H₉-iso | H | CHF₂ | CH₃ |
| F | NHSO₂C₅H₁₀-n | H | CHF₂ | CH₃ |
| F | NHSO₂—C₆H₅ | H | CHF₂ | CH₃ |
| F | NHSO₂—C₆H₄—CH₃ | H | CHF₂ | CH₃ |
| F | NHSO₂—C₆H₄—Cl | H | CHF₂ | CH₃ |
| H | N(CH₃)—SO₂CH₃ | H | CHF₂ | CH₃ |
| H | N(CH₃)—SO₂CF₃ | H | CHF₂ | CH₃ |
| H | N(CH₃)—SO₂C₂H₅ | H | CHF₂ | CH₃ |
| H | N(CH₃)—SO₂CH₂CF₃ | H | CHF₂ | CH₃ |
| H | N(CH₃)—SO₂C₃H₇-n | H | CHF₂ | CH₃ |
| H | N(CH₃)—SO₂C₃H₇-i | H | CHF₂ | CH₃ |

TABLE 1-continued

Examples of the compounds of the Formula (I)

| $R^1$ | $R^2$ | $R^3$ | $R^4$ | $R^5$ |
|---|---|---|---|---|
| H | N(CH$_3$)—SO$_2$-cyclopropyl | H | CHF$_2$ | CH$_3$ |
| H | N(CH$_3$)—SO$_2$CH$_2$CH$_2$CH$_2$Cl | H | CHF$_2$ | CH$_3$ |
| H | N(CH$_3$)—SO$_2$C$_4$H$_9$-n | H | CHF$_2$ | CH$_3$ |
| H | N(CH$_3$)—SO$_2$C$_4$H$_9$-sec | H | CHF$_2$ | CH$_3$ |
| H | N(CH$_3$)—SO$_2$C$_4$H$_9$-iso | H | CHF$_2$ | CH$_3$ |
| H | N(CH$_3$)—SO$_2$C$_5$H$_{10}$-n | H | CHF$_2$ | CH$_3$ |
| H | N(CH$_3$)—SO$_2$-phenyl | H | CHF$_2$ | CH$_3$ |
| H | N(CH$_3$)—SO$_2$-C$_6$H$_4$-CH$_3$ | H | CHF$_2$ | CH$_3$ |
| H | N(CH$_3$)—SO$_2$-C$_6$H$_4$-Cl | H | CHF$_2$ | CH$_3$ |
| F | N(CH$_3$)—SO$_2$CH$_3$ | H | CHF$_2$ | CH$_3$ |
| F | N(CH$_3$)—SO$_2$CF$_3$ | H | CHF$_2$ | CH$_3$ |
| F | N(CH$_3$)—SO$_2$C$_2$H$_5$ | H | CHF$_2$ | CH$_3$ |
| F | N(CH$_3$)—SO$_2$CH$_2$CF$_3$ | H | CHF$_2$ | CH$_3$ |
| F | N(CH$_3$)—SO$_2$C$_3$H$_7$-n | H | CHF$_2$ | CH$_3$ |
| F | N(CH$_3$)—SO$_2$C$_3$H$_7$-i | H | CHF$_2$ | CH$_3$ |
| F | N(CH$_3$)—SO$_2$-cyclopropyl | H | CHF$_2$ | CH$_3$ |
| F | N(CH$_3$)—SO$_2$CH$_2$CH$_2$CH$_2$Cl | H | CHF$_2$ | CH$_3$ |
| F | N(CH$_3$)—SO$_2$C$_4$H$_9$-n | H | CHF$_2$ | CH$_3$ |
| F | N(CH$_3$)—SO$_2$C$_4$H$_9$-sec | H | CHF$_2$ | CH$_3$ |
| F | N(CH$_3$)—SO$_2$C$_4$H$_9$-iso | H | CHF$_2$ | CH$_3$ |
| F | N(CH$_3$)—SO$_2$C$_5$H$_{10}$-n | H | CHF$_2$ | CH$_3$ |
| F | N(CH$_3$)—SO$_2$-phenyl | H | CHF$_2$ | CH$_3$ |
| F | N(CH$_3$)—SO$_2$-C$_6$H$_4$-CH$_3$ | H | CHF$_2$ | CH$_3$ |
| F | N(CH$_3$)—SO$_2$-C$_6$H$_4$-Cl | H | CHF$_2$ | CH$_3$ |
| H | N(C$_2$H$_5$)—SO$_2$CH$_3$ | H | CHF$_2$ | CH$_3$ |
| H | N(C$_2$H$_5$)—SO$_2$CF$_3$ | H | CHF$_2$ | CH$_3$ |
| H | N(C$_2$H$_5$)—SO$_2$C$_2$H$_5$ | H | CHF$_2$ | CH$_3$ |
| H | N(C$_2$H$_5$)—SO$_2$CH$_2$CF$_3$ | H | CHF$_2$ | CH$_3$ |
| H | N(C$_2$H$_5$)—SO$_2$C$_3$H$_7$-n | H | CHF$_2$ | CH$_3$ |
| H | N(C$_2$H$_5$)—SO$_2$C$_3$H$_7$-i | H | CHF$_2$ | CH$_3$ |
| H | N(C$_2$H$_5$)—SO$_2$-cyclopropyl | H | CHF$_2$ | CH$_3$ |
| H | N(C$_2$H$_5$)—SO$_2$CH$_2$CH$_2$CH$_2$Cl | H | CHF$_2$ | CH$_3$ |
| H | N(C$_2$H$_5$)—SO$_2$C$_4$H$_9$-n | H | CHF$_2$ | CH$_3$ |
| H | N(C$_2$H$_5$)—SO$_2$C$_4$H$_9$-sec | H | CHF$_2$ | CH$_3$ |
| H | N(C$_2$H$_5$)—SO$_2$C$_4$H$_9$-iso | H | CHF$_2$ | CH$_3$ |
| H | N(C$_2$H$_5$)—SO$_2$C$_5$H$_{10}$-n | H | CHF$_2$ | CH$_3$ |

TABLE 1-continued

Examples of the compounds of the Formula (I)

| $R^1$ | $R^2$ | $R^3$ | $R^4$ | $R^5$ |
|---|---|---|---|---|
| H | N(C$_2$H$_5$)—SO$_2$—C$_6$H$_5$ | H | CHF$_2$ | CH$_3$ |
| H | N(C$_2$H$_5$)—SO$_2$—C$_6$H$_4$—CH$_3$ | H | CHF$_2$ | CH$_3$ |
| H | N(C$_2$H$_5$)—SO$_2$—C$_6$H$_4$—Cl | H | CHF$_2$ | CH$_3$ |
| F | N(C$_2$H$_5$)—SO$_2$CH$_3$ | H | CHF$_2$ | CH$_3$ |
| F | N(C$_2$H$_5$)—SO$_2$CF$_3$ | H | CHF$_2$ | CH$_3$ |
| F | N(C$_2$H$_5$)—SO$_2$C$_2$H$_5$ | H | CHF$_2$ | CH$_3$ |
| F | N(C$_2$H$_5$)—SO$_2$CH$_2$CF$_3$ | H | CHF$_2$ | CH$_3$ |
| F | N(C$_2$H$_5$)—SO$_2$C$_3$H$_7$-n | H | CHF$_2$ | CH$_3$ |
| F | N(C$_2$H$_5$)—SO$_2$C$_3$H$_7$-i | H | CHF$_2$ | CH$_3$ |
| F | N(C$_2$H$_5$)—SO$_2$-cyclopropyl | H | CHF$_2$ | CH$_3$ |
| F | N(C$_2$H$_5$)—SO$_2$CH$_2$CH$_2$CH$_2$Cl | H | CHF$_2$ | CH$_3$ |
| F | N(C$_2$H$_5$)—SO$_2$C$_4$H$_9$-n | H | CHF$_2$ | CH$_3$ |
| F | N(C$_2$H$_5$)—SO$_2$C$_4$H$_9$-sec | H | CHF$_2$ | CH$_3$ |
| F | N(C$_2$H$_5$)—SO$_2$C$_4$H$_9$-iso | H | CHF$_2$ | CH$_3$ |
| F | N(C$_2$H$_5$)—SO$_2$CH$_3$ | H | CHF$_2$ | CH$_3$ |
| F | N(C$_2$H$_5$)—SO$_2$CF$_3$ | H | CHF$_2$ | CH$_3$ |
| F | N(C$_2$H$_5$)—SO$_2$C$_2$H$_5$ | H | CHF$_2$ | CH$_3$ |
| F | N(C$_2$H$_5$)—SO$_2$CH$_2$CF$_3$ | H | CHF$_2$ | CH$_3$ |
| F | N(C$_2$H$_5$)—SO$_2$C$_3$H$_7$-n | H | CHF$_2$ | CH$_3$ |
| F | N(C$_2$H$_5$)—SO$_2$C$_3$H$_7$-i | H | CHF$_2$ | CH$_3$ |
| F | N(C$_2$H$_5$)—SO$_2$-cyclopropyl | H | CHF$_2$ | CH$_3$ |
| F | N(C$_2$H$_5$)—SO$_2$CH$_2$CH$_2$CH$_2$Cl | H | CHF$_2$ | CH$_3$ |
| F | N(C$_2$H$_5$)—SO$_2$C$_4$H$_9$-n | H | CHF$_2$ | CH$_3$ |
| F | N(C$_2$H$_5$)—SO$_2$C$_4$H$_9$-sec | H | CHF$_2$ | CH$_3$ |
| F | N(C$_2$H$_5$)—SO$_2$C$_4$H$_9$-iso | H | CHF$_2$ | CH$_3$ |
| F | N(C$_2$H$_5$)—SO$_2$C$_5$H$_{10}$-n | H | CHF$_2$ | CH$_3$ |
| F | N(C$_2$H$_5$)—SO$_2$—C$_6$H$_5$ | H | CHF$_2$ | CH$_3$ |
| F | N(C$_2$H$_5$)—SO$_2$—C$_6$H$_4$—CH$_3$ | H | CHF$_2$ | CH$_3$ |
| F | N(C$_2$H$_5$)—SO$_2$—C$_6$H$_4$—Cl | H | CHF$_2$ | CH$_3$ |
| F | N(C$_2$H$_5$)—SO$_2$CH$_3$ | H | CHF$_2$ | C$_2$H$_5$ |
| F | N(C$_2$H$_5$)—SO$_2$CF$_3$ | H | CHF$_2$ | C$_2$H$_5$ |
| F | N(C$_2$H$_5$)—SO$_2$C$_2$H$_5$ | H | CHF$_2$ | C$_2$H$_5$ |
| F | N(C$_2$H$_5$)—SO$_2$CH$_2$CF$_3$ | H | CHF$_2$ | C$_2$H$_5$ |
| F | N(C$_2$H$_5$)—SO$_2$C$_3$H$_7$-n | H | CHF$_2$ | C$_2$H$_5$ |
| F | N(C$_2$H$_5$)—SO$_2$C$_3$H$_7$-i | H | CHF$_2$ | C$_2$H$_5$ |
| F | N(C$_2$H$_5$)—SO$_2$-cyclopropyl | H | CHF$_2$ | C$_2$H$_5$ |

TABLE 1-continued

Examples of the compounds of the Formula (I)

| R¹ | R² | R³ | R⁴ | R⁵ |
|---|---|---|---|---|
| F | N(C₂H₅)—SO₂CH₂CH₂CH₂Cl | H | CHF₂ | C₂H₅ |
| F | N(C₂H₅)—SO₂C₄H₉-n | H | CHF₂ | C₂H₅ |
| F | N(C₂H₅)—SO₂C₄H₉-sec | H | CHF₂ | C₂H₅ |
| F | N(C₂H₅)—SO₂C₄H₉-sec | H | CHF₂ | C₂H₅ |
| F | N(C₂H₅)—SO₂C₄H₉-iso | H | CHF₂ | C₂H₅ |
| F | N(C₂H₅)—SO₂C₅H₁₀-n | H | CHF₂ | C₂H₅ |
| F | N(C₂H₅)—SO₂—C₆H₅ | H | CHF₂ | C₂H₅ |
| F | N(C₂H₅)—SO₂—C₆H₄—CH₃ | H | CHF₂ | C₂H₅ |
| F | N(C₂H₅)—SO₂—C₆H₄—Cl | H | CHF₂ | C₂H₅ |
| H | NHSO₂CH₃ | H | CHF₂ | C₂H₅ |
| H | NHSO₂CF₃ | H | CHF₂ | C₂H₅ |
| H | NHSO₂C₂H₅ | H | CHF₂ | C₂H₅ |
| H | NHSO₂CH₂CF₃ | H | CHF₂ | C₂H₅ |
| H | NHSO₂C₃H₇-n | H | CHF₂ | C₂H₅ |
| H | NHSO₂C₃H₇-i | H | CHF₂ | C₂H₅ |
| H | NHSO₂-cyclopropyl | H | CHF₂ | C₂H₅ |
| H | NHSO₂CH₂CH₂CH₂Cl | H | CHF₂ | C₂H₅ |
| H | NHSO₂C₄H₉-n | H | CHF₂ | C₂H₅ |
| H | NHSO₂C₄H₉-sec | H | CHF₂ | C₂H₅ |
| H | NHSO₂C₄H₉-iso | H | CHF₂ | C₂H₅ |
| H | NHSO₂C₅H₁₀-n | H | CHF₂ | C₂H₅ |
| H | NHSO₂—C₆H₅ | H | CHF₂ | C₂H₅ |
| H | NHSO₂—C₆H₄—CH₃ | H | CHF₂ | C₂H₅ |
| H | NHSO₂—C₆H₄—Cl | H | CHF₂ | C₂H₅ |
| F | NHSO₂CH₃ | H | CHF₂ | C₂H₅ |
| F | NHSO₂CF₃ | H | CHF₂ | C₂H₅ |
| F | NHSO₂C₂H₅ | H | CHF₂ | C₂H₅ |
| F | NHSO₂CH₂CF₃ | H | CHF₂ | C₂H₅ |
| F | NHSO₂C₃H₇-n | H | CHF₂ | C₂H₅ |
| F | NHSO₂C₃H₇-i | H | CHF₂ | C₂H₅ |
| F | NHSO₂-cyclopropyl | H | CHF₂ | C₂H₅ |
| F | NHSO₂CH₂CH₂CH₂Cl | H | CHF₂ | C₂H₅ |
| F | NHSO₂C₄H₉-n | H | CHF₂ | C₂H₅ |
| F | NHSO₂C₄H₉-sec | H | CHF₂ | C₂H₅ |
| F | NHSO₂C₄H₉-iso | H | CHF₂ | C₂H₅ |
| F | NHSO₂C₅H₁₀-n | H | CHF₂ | C₂H₅ |
| F | NHSO₂—C₆H₅ | H | CHF₂ | C₂H₅ |
| F | NHSO₂—C₆H₄—CH₃ | H | CHF₂ | C₂H₅ |
| F | NHSO₂—C₆H₄—Cl | H | CHF₂ | C₂H₅ |
| H | NHSO₂CH₃ | CH₃ | CHF₂ | CH₃ |
| H | NHSO₂CF₃ | CH₃ | CHF₂ | CH₃ |
| H | NHSO₂C₂H₅ | CH₃ | CHF₂ | CH₃ |
| H | NHSO₂CH₂CF₃ | CH₃ | CHF₂ | CH₃ |
| H | NHSO₂C₃H₇-n | CH₃ | CHF₂ | CH₃ |
| H | NHSO₂C₃H₇-i | CH₃ | CHF₂ | CH₃ |
| H | NHSO₂-cyclopropyl | CH₃ | CHF₂ | CH₃ |
| H | NHSO₂CH₂CH₂CH₂Cl | CH₃ | CHF₂ | CH₃ |
| H | NHSO₂C₄H₉-n | CH₃ | CHF₂ | CH₃ |
| H | NHSO₂C₄H₉-sec | CH₃ | CHF₂ | CH₃ |
| H | NHSO₂C₄H₉-iso | CH₃ | CHF₂ | CH₃ |
| H | NHSO₂C₄H₁₀-n | CH₃ | CHF₂ | CH₃ |
| H | NHSO₂—C₆H₅ | CH₃ | CHF₂ | CH₃ |
| H | NHSO₂—C₆H₄—CH₃ | CH₃ | CHF₂ | CH₃ |
| H | NHSO₂—C₆H₄—Cl | CH₃ | CHF₂ | CH₃ |
| F | NHSO₂CH₃ | CH₃ | CHF₂ | CH₃ |
| F | NHSO₂CF₃ | CH₃ | CHF₂ | CH₃ |
| F | NHSO₂C₂H₅ | CH₃ | CHF₂ | CH₃ |
| F | NHSO₂CH₂CF₃ | CH₃ | CHF₂ | CH₃ |
| F | NHSO₂C₃H₇-n | CH₃ | CHF₂ | CH₃ |
| F | NHSO₂C₃H₇-i | CH₃ | CHF₂ | CH₃ |
| F | NHSO₂-cyclopropyl | CH₃ | CHF₂ | CH₃ |
| F | NHSO₂CH₂CH₂CH₂Cl | CH₃ | CHF₂ | CH₃ |
| F | NHSO₂C₄H₉-n | CH₃ | CHF₂ | CH₃ |
| F | NHSO₂C₄H₉-sec | CH₃ | CHF₂ | CH₃ |
| F | NHSO₂C₄H₉-iso | CH₃ | CHF₂ | CH₃ |

TABLE 1-continued

Examples of the compounds of the Formula (I)

| R¹ | R² | R³ | R⁴ | R⁵ |
|---|---|---|---|---|
| F | NHSO$_2$C$_5$H$_{10}$-n | CH$_3$ | CHF$_2$ | CH$_3$ |
| F | NHSO$_2$—<phenyl> | CH$_3$ | CHF$_2$ | CH$_3$ |
| F | NHSO$_2$—<phenyl>—CH$_3$ | CH$_3$ | CHF$_2$ | CH$_3$ |
| F | NHSO$_2$—<phenyl>—Cl | CH$_3$ | CHF$_2$ | CH$_3$ |
| F | NHSO$_2$CH$_3$ | Cl | CHF$_2$ | CH$_3$ |
| F | NHSO$_2$CF$_3$ | Cl | CHF$_2$ | CH$_3$ |
| F | NHSO$_2$C$_2$H$_5$ | Cl | CHF$_2$ | CH$_3$ |
| F | NHSO$_2$CH$_2$CF$_3$ | Cl | CHF$_2$ | CH$_3$ |
| F | NHSO$_2$C$_3$H$_7$-n | Cl | CHF$_2$ | CH$_3$ |
| F | NHSO$_2$C$_3$H$_7$-i | Cl | CHF$_2$ | CH$_3$ |
| F | NHSO$_2$—<cyclopropyl> | Cl | CHF$_2$ | CH$_3$ |
| F | NHSO$_2$CH$_2$CH$_2$CH$_2$Cl | Cl | CHF$_2$ | CH$_3$ |
| F | NHSO$_2$C$_4$H$_9$-n | Cl | CHF$_2$ | CH$_3$ |
| F | NHSO$_2$C$_4$H$_9$-sec | Cl | CHF$_2$ | CH$_3$ |
| F | NHSO$_2$C$_4$H$_9$-iso | Cl | CHF$_2$ | CH$_3$ |
| F | NHSO$_2$C$_5$H$_{10}$-n | Cl | CHF$_2$ | CH$_3$ |
| F | NHSO$_2$—<phenyl> | Cl | CHF$_2$ | CH$_3$ |
| F | NHSO$_2$—<phenyl>—CH$_3$ | Cl | CHF$_2$ | CH$_3$ |
| F | NHSO$_2$—<phenyl>—Cl | Cl | CHF$_2$ | CH$_3$ |
| F | NHSO$_2$CH$_3$ | F | CHF$_2$ | CH$_3$ |
| F | NHSO$_2$CF$_3$ | F | CHF$_2$ | CH$_3$ |
| F | NHSO$_2$C$_2$H$_5$ | F | CHF$_2$ | CH$_3$ |
| F | NHSO$_2$CH$_2$CF$_3$ | F | CHF$_2$ | CH$_3$ |
| F | NHSO$_2$C$_3$H$_7$-n | F | CHF$_2$ | CH$_3$ |
| F | NHSO$_2$C$_3$H$_7$-i | F | CHF$_2$ | CH$_3$ |
| F | NHSO$_2$—<cyclopropyl> | F | CHF$_2$ | CH$_3$ |
| F | NHSO$_2$CH$_2$CH$_2$CH$_2$Cl | F | CHF$_2$ | CH$_3$ |
| F | NHSO$_2$C$_4$H$_9$-n | F | CHF$_2$ | CH$_3$ |
| F | NHSO$_2$C$_4$H$_9$-sec | F | CHF$_2$ | CH$_3$ |
| F | NHSO$_2$C$_4$H$_9$-iso | F | CHF$_2$ | CH$_3$ |
| F | NHSO$_2$C$_5$H$_{10}$-n | F | CHF$_2$ | CH$_3$ |
| F | NHSO$_2$—<phenyl> | F | CHF$_2$ | CH$_3$ |
| F | NHSO$_2$—<phenyl>—CH$_3$ | F | CHF$_2$ | CH$_3$ |
| F | NHSO$_2$—<phenyl>—Cl | F | CHF$_2$ | CH$_3$ |
| F | N(CH$_3$)—SO$_2$CH$_3$ | CH$_3$ | CHF$_2$ | CH$_3$ |
| F | N(CH$_3$)—SO$_2$CF$_3$ | CH$_3$ | CHF$_2$ | CH$_3$ |
| F | N(CH$_3$)—SO$_2$C$_2$H$_5$ | CH$_3$ | CHF$_2$ | CH$_3$ |
| F | N(CH$_3$)—SO$_2$CH$_2$CF$_3$ | CH$_3$ | CHF$_2$ | CH$_3$ |
| F | N(CH$_3$)—SO$_2$C$_3$H$_7$-n | CH$_3$ | CHF$_2$ | CH$_3$ |
| F | N(CH$_3$)—SO$_2$C$_3$H$_7$-i | CH$_3$ | CHF$_2$ | CH$_3$ |
| F | N(CH$_3$)—SO$_2$—<cyclopropyl> | CH$_3$ | CHF$_2$ | CH$_3$ |
| F | N(CH$_3$)—SO$_2$CH$_2$CH$_2$CH$_2$Cl | CH$_3$ | CHF$_2$ | CH$_3$ |
| F | N(CH$_3$)—SO$_2$C$_4$H$_9$-n | CH$_3$ | CHF$_2$ | CH$_3$ |
| F | N(CH$_3$)—SO$_2$C$_4$H$_9$-sec | CH$_3$ | CHF$_2$ | CH$_3$ |
| F | N(CH$_3$)—SO$_2$C$_4$H$_9$-iso | CH$_3$ | CHF$_2$ | CH$_3$ |
| F | N(CH$_3$)—SO$_2$C$_5$H$_{10}$-n | CH$_3$ | CHF$_2$ | CH$_3$ |
| F | N(CH$_3$)—SO$_2$—<phenyl> | CH$_3$ | CHF$_2$ | CH$_3$ |
| F | N(CH$_3$)—SO$_2$—<phenyl>—CH$_3$ | CH$_3$ | CHF$_2$ | CH$_3$ |
| F | N(CH$_3$)—SO$_2$—<phenyl>—Cl | CH$_3$ | CHF$_2$ | CH$_3$ |
| F | N(CH$_3$)—SO$_2$CH$_3$ | Cl | CHF$_2$ | CH$_3$ |

TABLE 1-continued

Examples of the compounds of the Formula (I)

| R¹ | R² | R³ | R⁴ | R⁵ |
|---|---|---|---|---|
| F | N(CH₃)—SO₂CF₃ | Cl | CHF₂ | CH₃ |
| F | N(CH₃)—SO₂C₂H₅ | Cl | CHF₂ | CH₃ |
| F | N(CH₃)—SO₂CH₂CF₃ | Cl | CHF₂ | CH₃ |
| F | N(CH₃)—SO₂C₃H₇-n | Cl | CHF₂ | CH₃ |
| F | N(CH₃)—SO₂C₃H₇-i | Cl | CHF₂ | CH₃ |
| F | N(CH₃)—SO₂—cyclopropyl | Cl | CHF₂ | CH₃ |
| F | N(CH₃)—SO₂CH₂CH₂CH₂Cl | Cl | CHF₂ | CH₃ |
| F | N(CH₃)—SO₂C₄H₉-n | Cl | CHF₂ | CH₃ |
| F | N(CH₃)—SO₂C₄H₉-sec | Cl | CHF₂ | CH₃ |
| F | N(CH₃)—SO₂C₄H₉-iso | Cl | CHF₂ | CH₃ |
| F | N(CH₃)—SO₂C₅H₁₀-n | Cl | CHF₂ | CH₃ |
| F | N(CH₃)—SO₂—C₆H₅ | Cl | CHF₂ | CH₃ |
| F | N(CH₃)—SO₂—C₆H₄—CH₃ | Cl | CHF₂ | CH₃ |
| F | N(CH₃)—SO₂—C₆H₄—Cl | Cl | CHF₂ | CH₃ |
| F | N(CH₃)—SO₂CH₃ | F | CHF₂ | CH₃ |
| F | N(CH₃)—SO₂CF₃ | F | CHF₂ | CH₃ |
| F | N(CH₃)—SO₂C₂H₅ | F | CHF₂ | CH₃ |
| F | N(CH₃)—SO₂CH₂CF₃ | F | CHF₂ | CH₃ |
| F | N(CH₃)—SO₂C₃H₇-n | F | CHF₂ | CH₃ |
| F | N(CH₃)—SO₂C₃H₇-i | F | CHF₂ | CH₃ |
| F | N(CH₃)—SO₂—cyclopropyl | F | CHF₂ | CH₃ |
| F | N(CH₃)—SO₂CH₂CH₂CH₂Cl | F | CHF₂ | CH₃ |
| F | N(CH₃)—SO₂C₄H₉-n | F | CHF₂ | CH₃ |
| F | N(CH₃)—SO₂C₄H₉-sec | F | CHF₂ | CH₃ |
| F | N(CH₃)—SO₂C₄H₉-iso | F | CHF₂ | CH₃ |
| F | N(CH₃)—SO₂C₅H₁₀-n | F | CHF₂ | CH₃ |
| F | N(CH₃)—SO₂—C₆H₅ | F | CHF₂ | CH₃ |
| F | N(CH₃)—SO₂—C₆H₄—CH₃ | F | CHF₂ | CH₃ |
| F | N(CH₃)—SO₂—C₆H₄—Cl | F | CHF₂ | CH₃ |
| F | NHSO₂CH₃ | H | CHF₂ | NH₂ |
| F | NHSO₂CF₃ | H | CHF₂ | NH₂ |
| F | NHSO₂C₂H₅ | H | CHF₂ | NH₂ |
| F | NHSO₂CH₂CF₃ | H | CHF₂ | NH₂ |
| F | NHSO₂C₃H₇-n | H | CHF₂ | NH₂ |
| F | NHSO₂C₃H₇-i | H | CHF₂ | NH₂ |
| F | NHSO₂—cyclopropyl | H | CHF₂ | NH₂ |
| F | NHSO₂CH₂CH₂CH₂Cl | H | CHF₂ | NH₂ |
| F | NHSO₂C₄H₉-n | H | CHF₂ | NH₂ |
| F | NHSO₂C₄H₉-sec | H | CHF₂ | NH₂ |
| F | NHSO₂C₄H₉-iso | H | CHF₂ | NH₂ |
| F | NHSO₂C₅H₁₀-n | H | CHF₂ | NH₂ |
| F | NHSO₂—C₆H₅ | H | CHF₂ | NH₂ |
| F | NHSO₂—C₆H₄—CH₃ | H | CHF₂ | NH₂ |

TABLE 1-continued

Examples of the compounds of the Formula (I)

| R¹ | R² | R³ | R⁴ | R⁵ |
|---|---|---|---|---|
| F | NHSO₂—C₆H₄—Cl (para) | H | CHF₂ | NH₂ |
| F | N(CH₃)—SO₂CH₃ | H | CHF₂ | NH₂ |
| F | N(CH₃)—SO₂CF₃ | H | CHF₂ | NH₂ |
| F | N(CH₃)—SO₂C₂H₅ | H | CHF₂ | NH₂ |
| F | N(CH₃)—SO₂CH₂CF₃ | H | CHF₂ | NH₂ |
| F | N(CH₃)—SO₂C₃H₇-n | H | CHF₂ | NH₂ |
| F | N(CH₃)—SO₂C₃H₇-i | H | CHF₂ | NH₂ |
| F | N(CH₃)—SO₂-cyclopropyl | H | CHF₂ | NH₂ |
| F | N(CH₃)—SO₂CH₂CH₂CH₂Cl | H | CHF₂ | NH₂ |
| F | N(CH₃)—SO₂C₄H₉-n | H | CHF₂ | NH₂ |
| F | N(CH₃)—SO₂C₄H₉-sec | H | CHF₂ | NH₂ |
| F | N(CH₃)—SO₂C₄H₉-iso | H | CHF₂ | NH₂ |
| F | N(CH₃)—SO₂C₅H₁₀-n | H | CHF₂ | NH₂ |
| F | N(CH₃)—SO₂—C₆H₅ | H | CHF₂ | NH₂ |
| F | N(CH₃)—SO₂—C₆H₄—CH₃ | H | CHF₂ | NH₂ |
| F | N(CH₃)—SO₂—C₆H₄—Cl | H | CHF₂ | NH₂ |
| F | NHSO₂CH₃ | CH₃ | CHF₂ | NH₂ |
| F | NHSO₂CF₃ | CH₃ | CHF₂ | NH₂ |
| F | NHSO₂C₂H₅ | CH₃ | CHF₂ | NH₂ |
| F | NHSO₂CH₂CF₃ | CH₃ | CHF₂ | NH₂ |
| F | NHSO₂C₃H₇-n | CH₃ | CHF₂ | NH₂ |
| F | NHSO₂C₃H₇-i | CH₃ | CHF₂ | NH₂ |
| F | NHSO₂-cyclopropyl | CH₃ | CHF₂ | NH₂ |
| F | NHSO₂CH₂CH₂CH₂Cl | CH₃ | CHF₂ | NH₂ |
| F | NHSO₂C₄H₉-n | CH₃ | CHF₂ | NH₂ |
| F | NHSO₂C₄H₉-sec | CH₃ | CHF₂ | NH₂ |
| F | NHSO₂C₄H₉-iso | CH₃ | CHF₂ | NH₂ |
| F | NHSO₂C₅H₁₀-n | CH₃ | CHF₂ | NH₂ |
| F | NHSO₂—C₆H₅ | CH₃ | CHF₂ | NH₂ |
| F | NHSO₂—C₆H₄—CH₃ | CH₃ | CHF₂ | NH₂ |
| F | NHSO₂—C₆H₄—Cl | CH₃ | CHF₂ | NH₂ |
| F | NHSO₂CH₃ | H | CHF₂ | CHF₂ |
| F | NHSO₂CF₃ | H | CHF₂ | CHF₂ |
| F | NHSO₂C₂H₅ | H | CHF₂ | CHF₂ |
| F | NHSO₂CH₂CF₃ | H | CHF₂ | CHF₂ |
| F | NHSO₂C₃H₇-n | H | CHF₂ | CHF₂ |
| F | NHSO₂C₃H₇-i | H | CHF₂ | CHF₂ |
| F | NHSO₂-cyclopropyl | H | CHF₂ | CHF₂ |
| F | NHSO₂CH₂CH₂CH₂Cl | H | CHF₂ | CHF₂ |
| F | NHSO₂C₄H₉-n | H | CHF₂ | CHF₂ |
| F | NHSO₂C₄H₉-sec | H | CHF₂ | CHF₂ |
| F | NHSO₂C₄H₉-iso | H | CHF₂ | CHF₂ |
| F | NHSO₂C₅H₁₀-n | H | CHF₂ | CHF₂ |
| F | NHSO₂—C₆H₅ | H | CHF₂ | CHF₂ |
| F | NHSO₂—C₆H₄—CH₃ | H | CHF₂ | CHF₂ |
| F | NHSO₂—C₆H₄—Cl | H | CHF₂ | CHF₂ |
| F | N(CH₃)—SO₂CH₃ | H | CHF₂ | CHF₂ |
| F | N(CH₃)—SO₂CF₃ | H | CHF₂ | CHF₂ |
| F | N(CH₃)—SO₂C₂H₅ | H | CHF₂ | CHF₂ |
| F | N(CH₃)—SO₂CH₂CF₃ | H | CHF₂ | CHF₂ |
| F | N(CH₃)—SO₂C₃H₇-n | H | CHF₂ | CHF₂ |

TABLE 1-continued

Examples of the compounds of the Formula (I)

| R¹ | R² | R³ | R⁴ | R⁵ |
|---|---|---|---|---|
| F | N(CH₃)—SO₂C₃H₇-i | H | CHF₂ | CHF₂ |
| F | N(CH₃)—SO₂-cyclopropyl | H | CHF₂ | CHF₂ |
| F | N(CH₃)—SO₂CH₂CH₂CH₂Cl | H | CHF₂ | CHF₂ |
| F | N(CH₃)—SO₂C₄H₉-n | H | CHF₂ | CHF₂ |
| F | N(CH₃)—SO₂C₄H₉-sec | H | CHF₂ | CHF₂ |
| F | N(CH₃)—SO₂C₄H₉-iso | H | CHF₂ | CHF₂ |
| F | N(CH₃)—SO₂C₅H₁₀-n | H | CHF₂ | CHF₂ |
| F | N(CH₃)—SO₂—C₆H₅ | H | CHF₂ | CHF₂ |
| F | N(CH₃)—SO₂—C₆H₄—CH₃ | H | CHF₂ | CHF₂ |
| F | N(CH₃)—SO₂—C₆H₄—Cl | H | CHF₂ | CHF₂ |
| F | NHSO₂CH₃ | CH₃ | CHF₂ | CHF₂ |
| F | NHSO₂CF₃ | CH₃ | CHF₂ | CHF₂ |
| F | NHSO₂C₂H₅ | CH₃ | CHF₂ | CHF₂ |
| F | NHSO₂CH₂CF₃ | CH₃ | CHF₂ | CHF₂ |
| F | NHSO₂C₃F₇-n | CH₃ | CHF₂ | CHF₂ |
| F | NHSO₂C₃F₇-i | CH₃ | CHF₂ | CHF₂ |
| F | NHSO₂-cyclopropyl | CH₃ | CHF₂ | CHF₂ |
| F | NHSO₂CH₂CH₂CH₂Cl | CH₃ | CHF₂ | CHF₂ |
| F | NHSO₂C₄H₉-n | CH₃ | CHF₂ | CHF₂ |
| F | NHSO₂C₄F₉-sec | CH₃ | CHF₂ | CHF₂ |
| F | NHSO₂C₄H₉-iso | CH₃ | CHF₂ | CHF₂ |
| F | NHSO₂C₅H₁₀-n | CH₃ | CHF₂ | CHF₂ |
| F | NHSO₂—C₆H₅ | CH₃ | CHF₂ | CHF₂ |
| F | NHSO₂—C₆H₄—CH₃ | CH₃ | CHF₂ | CHF₂ |
| H | NHSO₂C₃H₇-n | H | C₂F₅ | CH₃ |
| H | NHSO₂C₃H₇-i | H | C₂F₅ | CH₃ |
| H | NHSO₂-cyclopropyl | H | C₂F₅ | CH₃ |
| H | NHSO₂CH₂CH₂CH₂Cl | H | C₂F₅ | CH₃ |
| H | NHSO₂C₄H₉-n | H | C₂F₅ | CH₃ |
| H | NHSO₂C₄H₉-sec | H | C₂F₅ | CH₃ |
| H | NHSO₂C₄H₉-iso | H | C₂F₅ | CH₃ |
| H | NHSO₂C₅H₁₀-n | H | C₂F₅ | CH₃ |
| H | NHSO₂—C₆H₅ | H | C₂F₅ | CH₃ |
| H | NHSO₂—C₆H₄—CH₃ | H | C₂F₅ | CH₃ |
| H | NHSO₂—C₆H₄—Cl | H | C₂F₅ | CH₃ |
| F | NHSO₂CH₃ | H | C₂F₅ | CH₃ |
| F | NHSO₂CF₃ | H | C₂F₅ | CH₃ |
| F | NHSO₂C₂H₅ | H | C₂F₅ | CH₃ |
| F | NHSO₂CH₂CF₃ | H | C₂F₅ | CH₃ |
| F | NHSO₂C₃H₇-n | H | C₂F₅ | CH₃ |
| F | NHSO₂C₃H₇-i | H | C₂F₅ | CH₃ |
| F | NHSO₂-cyclopropyl | H | C₂F₅ | CH₃ |
| F | NHSO₂CH₂CH₂CH₂Cl | H | C₂F₅ | CH₃ |
| F | NHSO₂C₄H₉-n | H | C₂F₅ | CH₃ |
| F | NHSO₂C₄H₉-sec | H | C₂F₅ | CH₃ |
| F | NHSO₂C₄H₉-iso | H | C₂F₅ | CH₃ |
| F | NHSO₂C₅H₁₀-n | H | C₂F₅ | CH₃ |
| F | NHSO₂—C₆H₅ | H | C₂F₅ | CH₃ |
| F | NHSO₂—C₆H₄—CH₃ | H | C₂F₅ | CH₃ |
| F | NHSO₂—C₆H₄—Cl | H | C₂F₅ | CH₃ |
| H | N(CH₃)—SO₂CH₃ | H | C₂F₅ | CH₃ |
| H | N(CH₃)—SO₂CF₃ | H | C₂F₅ | CH₃ |
| H | N(CH₃)—SO₂C₂H₅ | H | C₂F₅ | CH₃ |
| H | N(CH₃)—SO₂CH₂CF₃ | H | C₂F₅ | CH₃ |
| H | N(CH₃)—SO₂C₃H₇-n | H | C₂F₅ | CH₃ |

TABLE 1-continued

Examples of the compounds of the Formula (I)

| R¹ | R² | R³ | R⁴ | R⁵ |
|---|---|---|---|---|
| H | N(CH₃)—SO₂C₃H₇-i | H | C₂F₅ | CH₃ |
| H | N(CH₃)—SO₂-cyclopropyl  | H | C₂F₅ | CH₃ |
| H | N(CH₃)—SO₂CH₂CH₂CH₂Cl | H | C₂F₅ | CH₃ |
| H | N(CH₃)—SO₂C₄H₉-n | H | C₂F₅ | CH₃ |
| H | N(CH₃)—SO₂C₄H₉-sec | H | C₂F₅ | CH₃ |
| H | N(CH₃)—SO₂C₄H₉-iso | H | C₂F₅ | CH₃ |
| H | N(CH₃)—SO₂C₅H₁₀-n | H | C₂F₅ | CH₃ |
| H | N(CH₃)—SO₂—C₆H₅  | H | C₂F₅ | CH₃ |
| H | N(CH₃)—SO₂—C₆H₄—CH₃  | H | C₂F₅ | CH₃ |
| H | N(CH₃)—SO₂—C₆H₄—Cl | H | C₂F₅ | CH₃ |
| F | N(CH₃)—SO₂CH₃ | H | C₂F₅ | CH₃ |
| F | N(CH₃)—SO₂CF₃ | H | C₂F₅ | CH₃ |
| F | N(CH₃)—SO₂C₂H₅ | H | C₂F₅ | CH₃ |
| F | N(CH₃)—SO₂CH₂CF₃ | H | C₂F₅ | CH₃ |
| F | N(CH₃)—SO₂C₃H₇-n | H | C₂F₅ | CH₃ |
| F | N(CH₃)—SO₂C₃H₇-i | H | C₂F₅ | CH₃ |
| F | N(CH₃)—SO₂-cyclopropyl  | H | C₂F₅ | CH₃ |
| F | N(CH₃)—SO₂CH₂CH₂CH₂Cl | H | C₂F₅ | CH₃ |
| F | N(CH₃)—SO₂C₄H₉-n | H | C₂F₅ | CH₃ |
| F | N(CH₃)—SO₂C₄H₉-sec | H | C₂F₅ | CH₃ |
| F | N(CH₃)—SO₂C₄H₉-iso | H | C₂F₅ | CH₃ |
| F | N(CH₃)—SO₂C₅H₁₀-n | H | C₂F₅ | CH₃ |
| F | N(CH₃)—SO₂—C₆H₅  | H | C₂F₅ | CH₃ |
| F | N(CH₃)—SO₂—C₆H₄—CH₃  | H | C₂F₅ | CH₃ |
| F | N(CH₃)—SO₂—C₆H₄—Cl | H | C₂F₅ | CH₃ |
| H | N(C₂H₅)—SO₂CH₃ | H | C₂F₅ | CH₃ |
| H | N(C₂H₅)—SO₂CF₃ | H | C₂F₅ | CH₃ |
| H | N(C₂H₅)—SO₂C₂H₅ | H | C₂F₅ | CH₃ |
| H | N(C₂H₅)—SO₂CH₂CF₃ | H | C₂F₅ | CH₃ |
| H | N(C₂H₅)—SO₂C₃H₇-n | H | C₂F₅ | CH₃ |
| H | N(C₂H₅)—SO₂C₃H₇-i | H | C₂F₅ | CH₃ |
| H | N(C₂H₅)—SO₂-cyclopropyl  | H | C₂F₅ | CH₃ |
| H | N(C₂H₅)—SO₂CH₂CH₂CH₂Cl | H | C₂F₅ | CH₃ |
| H | N(C₂H₅)—SO₂C₄H₉-n | H | C₂F₅ | CH₃ |
| H | N(C₂H₅)—SO₂C₄H₉-sec | H | C₂F₅ | CH₃ |
| H | N(C₂H₅)—SO₂C₄H₉-iso | H | C₂F₅ | CH₃ |

TABLE 1-continued

Examples of the compounds of the Formula (I)

| R¹ | R² | R³ | R⁴ | R⁵ |
|---|---|---|---|---|
| F | N(CH₃)—SO₂C₃H₇-i | H | CHF₂ | CHF₂ |
| F | N(CH₃)—SO₂-cyclopropyl | H | CHF₂ | CHF₂ |
| F | N(CH₃)—SO₂CH₂CH₂CH₂Cl | H | CHF₂ | CHF₂ |
| F | N(CH₃)—SO₂C₄H₉-n | H | CHF₂ | CHF₂ |
| F | N(CH₃)—SO₂C₄H₉-sec | H | CHF₂ | CHF₂ |
| F | N(CH₃)—SO₂C₄H₉-iso | H | CHF₂ | CHF₂ |
| F | N(CH₃)—SO₂C₅H₁₀-n | H | CHF₂ | CHF₂ |
| F | N(CH₃)—SO₂—C₆H₅ | H | CHF₂ | CHF₂ |
| F | N(CH₃)—SO₂—C₆H₄—CH₃ | H | CHF₂ | CHF₂ |
| F | N(CH₃)—SO₂—C₆H₄—Cl | H | CHF₂ | CHF₂ |
| F | NHSO₂CH₃ | CH₃ | CHF₂ | CHF₂ |
| F | NHSO₂CF₃ | CH₃ | CHF₂ | CHF₂ |
| F | NHSO₂C₂H₅ | CH₃ | CHF₂ | CHF₂ |
| F | NHSO₂CH₂CF₃ | CH₃ | CHF₂ | CHF₂ |
| F | NHSO₂C₃F₇-n | CH₃ | CHF₂ | CHF₂ |
| F | NHSO₂C₃F₇-i | CH₃ | CHF₂ | CHF₂ |
| F | NHSO₂-cyclopropyl | CH₃ | CHF₂ | CHF₂ |
| F | NHSO₂CH₂CH₂CH₂Cl | CH₃ | CHF₂ | CHF₂ |
| F | NHSO₂C₄H₉-n | CH₃ | CHF₂ | CHF₂ |
| F | NHSO₂C₄H₉-sec | CH₃ | CHF₂ | CHF₂ |
| F | NHSO₂C₄H₉-iso | CH₃ | CHF₂ | CHF₂ |
| F | NHSO₂C₅H₁₀-n | CH₃ | CHF₂ | CHF₂ |
| F | NHSO₂—C₆H₅ | CH₃ | CHF₂ | CHF₂ |
| F | NHSO₂—C₆H₄—CH₃ | CH₃ | CHF₂ | CHF₂ |
| H | NHSO₂C₃H₇-n | H | C₂F₅ | CH₃ |
| H | NHSO₂C₃H₇-i | H | C₂F₅ | CH₃ |
| H | NHSO₂-cyclopropyl | H | C₂F₅ | CH₃ |
| H | NHSO₂CH₂CH₂CH₂Cl | H | C₂F₅ | CH₃ |
| H | NHSO₂C₄H₉-n | H | C₂F₅ | CH₃ |
| H | NHSO₂C₄H₉-sec | H | C₂F₅ | CH₃ |
| H | NHSO₂C₄H₉-iso | H | C₂F₅ | CH₃ |
| H | NHSO₂C₅H₁₀-n | H | C₂F₅ | CH₃ |
| H | NHSO₂—C₆H₅ | H | C₂F₅ | CH₃ |
| H | NHSO₂—C₆H₄—CH₃ | H | C₂F₅ | CH₃ |
| H | NHSO₂—C₆H₄—Cl | H | C₂F₅ | CH₃ |
| F | NHSO₂CH₃ | H | C₂F₅ | CH₃ |
| F | NHSO₂CF₃ | H | C₂F₅ | CH₃ |
| F | NHSO₂C₂H₅ | H | C₂F₅ | CH₃ |
| F | NHSO₂CH₂CF₃ | H | C₂F₅ | CH₃ |
| F | NHSO₂C₃H₇-n | H | C₂F₅ | CH₃ |
| F | NHSO₂C₃H₇-i | H | C₂F₅ | CH₃ |
| F | NHSO₂-cyclopropyl | H | C₂F₅ | CH₃ |
| F | NHSO₂CH₂CH₂CH₂Cl | H | C₂F₅ | CH₃ |
| F | NHSO₂C₄H₉-n | H | C₂F₅ | CH₃ |
| F | NHSO₂C₄H₉-sec | H | C₂F₅ | CH₃ |
| F | NHSO₂C₄H₉-iso | H | C₂F₅ | CH₃ |
| F | NHSO₂C₅H₁₀-n | H | C₂F₅ | CH₃ |
| F | NHSO₂—C₆H₅ | H | C₂F₅ | CH₃ |
| F | NHSO₂—C₆H₄—CH₃ | H | C₂F₅ | CH₃ |
| F | NHSO₂—C₆H₄—Cl | H | C₂F₅ | CH₃ |
| H | N(CH₃)—SO₂CH₃ | H | C₂F₅ | CH₃ |
| H | N(CH₃)—SO₂CF₃ | H | C₂F₅ | CH₃ |
| H | N(CH₃)—SO₂C₂H₅ | H | C₂F₅ | CH₃ |
| H | N(CH₃)—SO₂CH₂CF₃ | H | C₂F₅ | CH₃ |
| H | N(CH₃)—SO₂C₃H₇-n | H | C₂F₅ | CH₃ |

TABLE 1-continued

Examples of the compounds of the Formula (I)

| $R^1$ | $R^2$ | $R^3$ | $R^4$ | $R^5$ |
|---|---|---|---|---|
| H | NHSO$_2$-cyclopropyl | H | $C_2F_5$ | $C_2H_5$ |
| H | NHSO$_2$CH$_2$CH$_2$CH$_2$Cl | H | $C_2F_5$ | $C_2H_5$ |
| H | NHSO$_2$C$_4$H$_9$-n | H | $C_2F_5$ | $C_2H_5$ |
| H | NHSO$_2$C$_4$H$_9$-sec | H | $C_2F_5$ | $C_2H_5$ |
| H | NHSO$_2$C$_4$H$_9$-iso | H | $C_2F_5$ | $C_2H_5$ |
| H | NHSO$_2$C$_5$H$_{10}$-n | H | $C_2F_5$ | $C_2H_5$ |
| H | NHSO$_2$-phenyl | H | $C_2F_5$ | $C_2H_5$ |
| H | NHSO$_2$-C$_6$H$_4$-CH$_3$ | H | $C_2F_5$ | $C_2H_5$ |
| H | NHSO$_2$-C$_6$H$_4$-Cl | H | $C_2F_5$ | $C_2H_5$ |
| F | NHSO$_2$CH$_3$ | H | $C_2F_5$ | $C_2H_5$ |
| F | NHSO$_2$CF$_3$ | H | $C_2F_5$ | $C_2H_5$ |
| F | NHSO$_2$C$_2$H$_5$ | H | $C_2F_5$ | $C_2H_5$ |
| F | NHSO$_2$CH$_2$CF$_3$ | H | $C_2F_5$ | $C_2H_5$ |
| F | NHSO$_2$C$_3$H$_7$-n | H | $C_2F_5$ | $C_2H_5$ |
| F | NHSO$_2$C$_3$H$_7$-i | H | $C_2F_5$ | $C_2H_5$ |
| F | NHSO$_2$-cyclopropyl | H | $C_2F_5$ | $C_2H_5$ |
| F | NHSO$_2$CH$_2$CH$_2$CH$_2$Cl | H | $C_2F_5$ | $C_2H_5$ |
| F | NHSO$_2$C$_4$H$_9$-n | H | $C_2F_5$ | $C_2H_5$ |
| F | NHSO$_2$C$_4$H$_9$-sec | H | $C_2F_5$ | $C_2H_5$ |
| F | NHSO$_2$C$_4$H$_9$-iso | H | $C_2F_5$ | $C_2H_5$ |
| F | NHSO$_2$C$_5$H$_{10}$-n | H | $C_2F_5$ | $C_2H_5$ |
| F | NHSO$_2$-phenyl | H | $C_2F_5$ | $C_2H_5$ |
| F | NHSO$_2$-C$_6$H$_4$-CH$_3$ | H | $C_2F_5$ | $C_2H_5$ |
| F | NHSO$_2$-C$_6$H$_4$-Cl | H | $C_2F_5$ | $C_2H_5$ |
| H | NHSO$_2$CH$_3$ | CH$_3$ | $C_2F_5$ | CH$_3$ |
| H | NHSO$_2$CF$_3$ | CH$_3$ | $C_2F_5$ | CH$_3$ |
| H | NHSO$_2$C$_2$H$_5$ | CH$_3$ | $C_2F_5$ | CH$_3$ |
| H | NHSO$_2$CH$_2$CF$_3$ | CH$_3$ | $C_2F_5$ | CH$_3$ |
| H | NHSO$_2$C$_3$H$_7$-n | CH$_3$ | $C_2F_5$ | CH$_3$ |
| H | NHSO$_2$C$_3$H$_7$-i | CH$_3$ | $C_2F_5$ | CH$_3$ |
| H | NHSO$_2$-cyclopropyl | CH$_3$ | $C_2F_5$ | CH$_3$ |
| H | NHSO$_2$CH$_2$CH$_2$CH$_2$Cl | CH$_3$ | $C_2F_5$ | CH$_3$ |
| H | NHSO$_2$C$_4$H$_9$-n | CH$_3$ | $C_2F_5$ | CH$_3$ |
| H | NHSO$_2$C$_4$H$_9$-sec | CH$_3$ | $C_2F_5$ | CH$_3$ |
| H | NHSO$_2$C$_4$H$_9$-iso | CH$_3$ | $C_2F_5$ | CH$_3$ |
| H | NHSO$_2$C$_5$H$_{10}$-n | CH$_3$ | $C_2F_5$ | CH$_3$ |
| H | NHSO$_2$-phenyl | CH$_3$ | $C_2F_5$ | CH$_3$ |
| H | NHSO$_2$-C$_6$H$_4$-CH$_3$ | CH$_3$ | $C_2F_5$ | CH$_3$ |
| H | NHSO$_2$-C$_6$H$_4$-Cl | CH$_3$ | $C_2F_5$ | CH$_3$ |
| F | NHSO$_2$CH$_3$ | CH$_3$ | $C_2F_5$ | CH$_3$ |
| F | NHSO$_2$CF$_3$ | CH$_3$ | $C_2F_5$ | CH$_3$ |
| F | NHSO$_2$C$_2$H$_5$ | CH$_3$ | $C_2F_5$ | CH$_3$ |
| F | NHSO$_2$CH$_2$CF$_3$ | CH$_3$ | $C_2F_5$ | CH$_3$ |
| F | NHSO$_2$C$_3$H$_7$-n | CH$_3$ | $C_2F_5$ | CH$_3$ |
| F | NHSO$_2$C$_3$H$_7$-i | CH$_3$ | $C_2F_5$ | CH$_3$ |
| F | NHSO$_2$-cyclopropyl | CH$_3$ | $C_2F_5$ | CH$_3$ |
| F | NHSO$_2$CH$_2$CH$_2$CH$_2$Cl | CH$_3$ | $C_2F_5$ | CH$_3$ |
| F | NHSO$_2$C$_4$H$_9$-n | CH$_3$ | $C_2F_5$ | CH$_3$ |
| F | NHSO$_2$C$_4$H$_9$-sec | CH$_3$ | $C_2F_5$ | CH$_3$ |
| F | NHSO$_2$C$_4$H$_9$-iso | CH$_3$ | $C_2F_5$ | CH$_3$ |
| F | NHSO$_2$C$_5$H$_{10}$-n | CH$_3$ | $C_2F_5$ | CH$_3$ |
| F | NHSO$_2$-phenyl | CH$_3$ | $C_2F_5$ | CH$_3$ |
| F | NHSO$_2$-C$_6$H$_4$-CH$_3$ | CH$_3$ | $C_2F_5$ | CH$_3$ |
| F | NHSO$_2$-C$_6$H$_4$-Cl | CH$_3$ | $C_2F_5$ | CH$_3$ |
| F | NHSO$_2$CH$_3$ | Cl | $C_2F_5$ | CH$_3$ |
| F | NHSO$_2$CF$_3$ | Cl | $C_2F_5$ | CH$_3$ |
| F | NHSO$_2$C$_2$H$_5$ | Cl | $C_2F_5$ | CH$_3$ |
| F | NHSO$_2$CH$_2$CF$_3$ | Cl | $C_2F_5$ | CH$_3$ |
| F | NHSO$_2$C$_3$H$_7$-n | Cl | $C_2F_5$ | CH$_3$ |
| F | NHSO$_2$C$_3$H$_7$-i | Cl | $C_2F_5$ | CH$_3$ |
| F | NHSO$_2$-cyclopropyl | Cl | $C_2F_5$ | CH$_3$ |
| F | NHSO$_2$CH$_2$CH$_2$CH$_2$Cl | Cl | $C_2F_5$ | CH$_3$ |
| F | NHSO$_2$C$_4$H$_9$-n | Cl | $C_2F_5$ | CH$_3$ |
| F | NHSO$_2$C$_4$H$_9$-sec | Cl | $C_2F_5$ | CH$_3$ |
| F | NHSO$_2$C$_4$H$_9$-iso | Cl | $C_2F_5$ | CH$_3$ |
| F | NHSO$_2$C$_5$H$_{10}$-n | Cl | $C_2F_5$ | CH$_3$ |
| F | NHSO$_2$-phenyl | Cl | $C_2F_5$ | CH$_3$ |
| F | NHSO$_2$-C$_6$H$_4$-CH$_3$ | Cl | $C_2F_5$ | CH$_3$ |

TABLE 1-continued

Examples of the compounds of the Formula (I)

| R¹ | R² | R³ | R⁴ | R⁵ |
|---|---|---|---|---|
| F | NHSO₂—C₆H₄—Cl (4-Cl-phenyl) | Cl | C₂F₅ | CH₃ |
| F | NHSO₂CH₃ | F | C₂F₅ | CH₃ |
| F | NHSO₂CF₃ | F | C₂F₅ | CH₃ |
| F | NHSO₂C₂H₅ | F | C₂F₅ | CH₃ |
| F | NHSO₂CH₂CF₃ | F | C₂F₅ | CH₃ |
| F | NHSO₂C₃H₇-n | F | C₂F₅ | CH₃ |
| F | NHSO₂C₃H₇-i | F | C₂F₅ | CH₃ |
| F | NHSO₂—cyclopropyl | F | C₂F₅ | CH₃ |
| F | NHSO₂CH₂CH₂CH₂Cl | F | C₂F₅ | CH₃ |
| F | NHSO₂C₄H₉-n | F | C₂F₅ | CH₃ |
| F | NHSO₂C₄H₉-sec | F | C₂F₅ | CH₃ |
| F | NHSO₂C₄H₉-iso | F | C₂F₅ | CH₃ |
| F | NHSO₂C₅H₁₀-n | F | C₂F₅ | CH₃ |
| F | NHSO₂—C₆H₅ | F | C₂F₅ | CH₃ |
| F | NHSO₂—C₆H₄—CH₃ | F | C₂F₅ | CH₃ |
| F | NHSO₂—C₆H₄—Cl | F | C₂F₅ | CH₃ |
| F | N(CH₃)—SO₂CH₃ | CH₃ | C₂F₅ | CH₃ |
| F | N(CH₃)—SO₂CF₃ | CH₃ | C₂F₅ | CH₃ |
| F | N(CH₃)—SO₂C₂H₅ | CH₃ | C₂F₅ | CH₃ |
| F | N(CH₃)—SO₂CH₂CF₃ | CH₃ | C₂F₅ | CH₃ |
| F | N(CH₃)—SO₂C₃H₇-n | CH₃ | C₂F₅ | CH₃ |
| F | N(CH₃)—SO₂C₃H₇-i | CH₃ | C₂F₅ | CH₃ |
| F | N(CH₃)—SO₂—cyclopropyl | CH₃ | C₂F₅ | CH₃ |
| F | N(CH₃)—SO₂CH₂CH₂CH₂Cl | CH₃ | C₂F₅ | CH₃ |
| F | N(CH₃)—SO₂C₄H₉-n | CH₃ | C₂F₅ | CH₃ |
| F | N(CH₃)—SO₂C₄H₉-sec | CH₃ | C₂F₅ | CH₃ |
| F | N(CH₃)—SO₂C₄H₉-iso | CH₃ | C₂F₅ | CH₃ |
| F | N(CH₃)—SO₂C₅H₁₀-n | CH₃ | C₂F₅ | CH₃ |
| F | N(CH₃)—SO₂—C₆H₅ | CH₃ | C₂F₅ | CH₃ |
| F | N(CH₃)—SO₂—C₆H₄—CH₃ | CH₃ | C₂F₅ | CH₃ |
| F | N(CH₃)—SO₂—C₆H₄—Cl | CH₃ | C₂F₅ | CH₃ |
| F | N(CH₃)—SO₂CH₃ | Cl | C₂F₅ | CH₃ |
| F | N(CH₃)—SO₂CF₃ | Cl | C₂F₅ | CH₃ |
| F | N(CH₃)—SO₂C₂H₅ | Cl | C₂F₅ | CH₃ |
| F | N(CH₃)—SO₂CH₂CF₃ | Cl | C₂F₅ | CH₃ |
| F | N(CH₃)—SO₂C₃H₇-n | Cl | C₂F₅ | CH₃ |
| F | N(CH₃)—SO₂C₃H₇-i | Cl | C₂F₅ | CH₃ |
| F | N(CH₃)—SO₂—cyclopropyl | Cl | C₂F₅ | CH₃ |
| F | N(CH₃)—SO₂CH₂CH₂CH₂Cl | Cl | C₂F₅ | CH₃ |
| F | N(CH₃)—SO₂C₄H₉-n | Cl | C₂F₅ | CH₃ |
| F | N(CH₃)—SO₂C₄H₉-sec | Cl | C₂F₅ | CH₃ |
| F | N(CH₃)—SO₂C₄H₉-iso | Cl | C₂F₅ | CH₃ |
| F | N(CH₃)—SO₂C₅H₁₀-n | Cl | C₂F₅ | CH₃ |
| F | N(CH₃)—SO₂—C₆H₅ | Cl | C₂F₅ | CH₃ |

TABLE 1-continued

Examples of the compounds of the Formula (I)

| R¹ | R² | R³ | R⁴ | R⁵ |
|---|---|---|---|---|
| F | 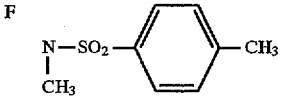 N—SO₂—⟨C₆H₄⟩—CH₃ with N-CH₃ | Cl | C₂F₅ | CH₃ |
| F | N—SO₂—⟨C₆H₄⟩—Cl with N-CH₃ | Cl | C₂F₅ | CH₃ |
| F | N—SO₂CH₃ with N-CH₃ | F | C₂F₅ | CH₃ |
| F | N—SO₂CF₃ with N-CH₃ | F | C₂F₅ | CH₃ |
| F | N—SO₂C₂H₅ with N-CH₃ | F | C₂F₅ | CH₃ |
| F | N—SO₂CH₂CF₃ with N-CH₃ | F | C₂F₅ | CH₃ |
| F | N—SO₂C₃H₇-n with N-CH₃ | F | C₂F₅ | CH₃ |
| F | N—SO₂C₃H₇-i with N-CH₃ | F | C₂F₅ | CH₃ |
| F | N—SO₂—⟨cyclopropyl⟩ with N-CH₃ | F | C₂F₅ | CH₃ |
| F | N—SO₂CH₂CH₂CH₂Cl with N-CH₃ | F | C₂F₅ | CH₃ |
| F | N—SO₂C₄H₉-n with N-CH₃ | F | C₂F₅ | CH₃ |
| F | N—SO₂C₄H₉-sec with N-CH₃ | F | C₂F₅ | CH₃ |
| F | N—SO₂C₄H₉-iso with N-CH₃ | F | C₂F₅ | CH₃ |
| F | N—SO₂C₅H₁₀-n with N-CH₃ | F | C₂F₅ | CH₃ |
| F | N—SO₂—⟨C₆H₅⟩ with N-CH₃ | F | C₂F₅ | CH₃ |
| F | N—SO₂—⟨C₆H₄⟩—CH₃ with N-CH₃ | F | C₂F₅ | CH₃ |
| F | N—SO₂—⟨C₆H₄⟩—Cl with N-CH₃ | F | C₂F₅ | CH₃ |
| F | NHSO₂CH₃ | H | C₂F₅ | NH₂ |
| F | NHSO₂CF₃ | H | C₂F₅ | NH₂ |
| F | NHSO₂C₂H₅ | H | C₂F₅ | NH₂ |
| F | NHSO₂CH₂CF₃ | H | C₂F₅ | NH₂ |
| F | NHSO₂C₃H₇-n | H | C₂F₅ | NH₂ |
| F | NHSO₂C₃H₇-i | H | C₂F₅ | NH₂ |
| F | NHSO₂—⟨cyclopropyl⟩ | H | C₂F₅ | NH₂ |
| F | NHSO₂CH₂CH₂CH₂Cl | H | C₂F₅ | NH₂ |
| F | NHSO₂C₄H₉-n | H | C₂F₅ | NH₂ |
| F | NHSO₂C₄H₉-sec | H | C₂F₅ | NH₂ |
| F | NHSO₂C₄H₉-iso | H | C₂F₅ | NH₂ |
| F | NHSO₂C₅H₁₀-n | H | C₂F₅ | NH₂ |
| F | NHSO₂—⟨C₆H₅⟩ | H | C₂F₅ | NH₂ |
| F | NHSO₂—⟨C₆H₄⟩—CH₃ | H | C₂F₅ | NH₂ |
| F | NHSO₂—⟨C₆H₄⟩—Cl | H | C₂F₅ | NH₂ |
| F | N—SO₂CH₃ with N-CH₃ | H | C₂F₅ | NH₂ |
| F | N—SO₂CF₃ with N-CH₃ | H | C₂F₅ | NH₂ |
| F | N—SO₂C₂H₅ with N-CH₃ | H | C₂F₅ | NH₂ |
| F | N—SO₂CH₂CF₃ with N-CH₃ | H | C₂F₅ | NH₂ |
| F | N—SO₂C₃H₇-n with N-CH₃ | H | C₂F₅ | NH₂ |
| F | N—SO₂C₃H₇-i with N-CH₃ | H | C₂F₅ | NH₂ |
| F | N—SO₂—⟨cyclopropyl⟩ with N-CH₃ | H | C₂F₅ | NH₂ |
| F | N—SO₂CH₂CH₂CH₂Cl with N-CH₃ | H | C₂F₅ | NH₂ |
| F | N—SO₂C₄H₉-n with N-CH₃ | H | C₂F₅ | NH₂ |
| F | N—SO₂C₄H₉-sec with N-CH₃ | H | C₂F₅ | NH₂ |
| F | N—SO₂C₄H₉-iso with N-CH₃ | H | C₂F₅ | NH₂ |

TABLE 1-continued

Examples of the compounds of the Formula (I)

| R¹ | R² | R³ | R⁴ | R⁵ |
|----|----|----|----|----|
| F | NHSO₂—⟨C₆H₄⟩—Cl | Cl | C₂F₅ | CH₃ |
| F | NHSO₂CH₃ | F | C₂F₅ | CH₃ |
| F | NHSO₂CF₃ | F | C₂F₅ | CH₃ |
| F | NHSO₂C₂H₅ | F | C₂F₅ | CH₃ |
| F | NHSO₂CH₂CF₃ | F | C₂F₅ | CH₃ |
| F | NHSO₂C₃H₇-n | F | C₂F₅ | CH₃ |
| F | NHSO₂C₃H₇-i | F | C₂F₅ | CH₃ |
| F | NHSO₂—⟨cyclopropyl⟩ | F | C₂F₅ | CH₃ |
| F | NHSO₂CH₂CH₂CH₂Cl | F | C₂F₅ | CH₃ |
| F | NHSO₂C₄H₉-n | F | C₂F₅ | CH₃ |
| F | NHSO₂C₄H₉-sec | F | C₂F₅ | CH₃ |
| F | NHSO₂C₄H₉-iso | F | C₂F₅ | CH₃ |
| F | NHSO₂C₅H₁₀-n | F | C₂F₅ | CH₃ |
| F | NHSO₂—⟨C₆H₅⟩ | F | C₂F₅ | CH₃ |
| F | NHSO₂—⟨C₆H₄⟩—CH₃ | F | C₂F₅ | CH₃ |
| F | NHSO₂—⟨C₆H₄⟩—Cl | F | C₂F₅ | CH₃ |
| F | N(CH₃)—SO₂CH₃ | CH₃ | C₂F₅ | CH₃ |
| F | N(CH₃)—SO₂CF₃ | CH₃ | C₂F₅ | CH₃ |
| F | N(CH₃)—SO₂C₂H₅ | CH₃ | C₂F₅ | CH₃ |
| F | N(CH₃)—SO₂CH₂CF₃ | CH₃ | C₂F₅ | CH₃ |
| F | N(CH₃)—SO₂C₃H₇-n | CH₃ | C₂F₅ | CH₃ |
| F | N(CH₃)—SO₂C₃H₇-i | CH₃ | C₂F₅ | CH₃ |
| F | N(CH₃)—SO₂—⟨cyclopropyl⟩ | CH₃ | C₂F₅ | CH₃ |
| F | N(CH₃)—SO₂CH₂CH₂CH₂Cl | CH₃ | C₂F₅ | CH₃ |
| F | N(CH₃)—SO₂C₄H₉-n | CH₃ | C₂F₅ | CH₃ |
| F | N(CH₃)—SO₂C₄H₉-sec | CH₃ | C₂F₅ | CH₃ |
| F | N(CH₃)—SO₂C₄H₉-iso | CH₃ | C₂F₅ | CH₃ |
| F | N(CH₃)—SO₂C₅H₁₀-n | CH₃ | C₂F₅ | CH₃ |
| F | N(CH₃)—SO₂—⟨C₆H₅⟩ | CH₃ | C₂F₅ | CH₃ |
| F | N(CH₃)—SO₂—⟨C₆H₄⟩—CH₃ | CH₃ | C₂F₅ | CH₃ |
| F | N(CH₃)—SO₂—⟨C₆H₄⟩—Cl | CH₃ | C₂F₅ | CH₃ |
| F | N(CH₃)—SO₂CH₃ | Cl | C₂F₅ | CH₃ |
| F | N(CH₃)—SO₂CF₃ | Cl | C₂F₅ | CH₃ |
| F | N(CH₃)—SO₂C₂H₅ | Cl | C₂F₅ | CH₃ |
| F | N(CH₃)—SO₂CH₂CF₃ | Cl | C₂F₅ | CH₃ |
| F | N(CH₃)—SO₂C₃H₇-n | Cl | C₂F₅ | CH₃ |
| F | N(CH₃)—SO₂C₃H₇-i | Cl | C₂F₅ | CH₃ |
| F | N(CH₃)—SO₂—⟨cyclopropyl⟩ | Cl | C₂F₅ | CH₃ |
| F | N(CH₃)—SO₂CH₂CH₂CH₂Cl | Cl | C₂F₅ | CH₃ |
| F | N(CH₃)—SO₂C₄H₉-n | Cl | C₂F₅ | CH₃ |
| F | N(CH₃)—SO₂C₄H₉-sec | Cl | C₂F₅ | CH₃ |
| F | N(CH₃)—SO₂C₄H₉-iso | Cl | C₂F₅ | CH₃ |
| F | N(CH₃)—SO₂C₅H₁₀-n | Cl | C₂F₅ | CH₃ |
| F | N(CH₃)—SO₂—⟨C₆H₅⟩ | Cl | C₂F₅ | CH₃ |

TABLE 1-continued

Examples of the compounds of the Formula (I)

| R¹ | R² | R³ | R⁴ | R⁵ |
|---|---|---|---|---|
| F | NHSO$_2$CH$_2$CF$_3$ | CH$_3$ | C$_2$F$_5$ | CHF$_2$ |
| F | NHSO$_2$C$_3$H$_7$-n | CH$_3$ | C$_2$F$_5$ | CHF$_2$ |
| F | NHSO$_2$C$_3$H$_7$-i | CH$_3$ | C$_2$F$_5$ | CHF$_2$ |
| F | NHSO$_2$— | CH$_3$ | C$_2$F$_5$ | CHF$_2$ |
| F | NHSO$_2$CH$_2$CH$_2$CH$_2$Cl | CH$_3$ | C$_2$F$_5$ | CHF$_2$ |
| F | NHSO$_2$C$_4$H$_9$-n | CH$_3$ | C$_2$F$_5$ | CHF$_2$ |
| F | NHSO$_2$C$_4$H$_9$-sec | CH$_3$ | C$_2$F$_5$ | CHF$_2$ |
| F | NHSO$_2$C$_4$H$_9$-iso | CH$_3$ | C$_2$F$_5$ | CHF$_2$ |
| F | NHSO$_2$C$_5$H$_{10}$-n | CH$_3$ | C$_2$F$_5$ | CHF$_2$ |
| F | NHSO$_2$—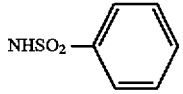 | CH$_3$ | C$_2$F$_5$ | CHF$_2$ |
| F | NHSO$_2$—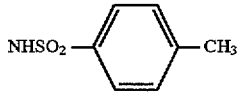—CH$_3$ | CH$_3$ | C$_2$F$_5$ | CHF$_2$ |
| F | NHSO$_2$—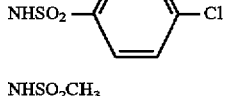—Cl | CH$_3$ | C$_2$F$_5$ | CHF$_2$ |
| H | NHSO$_2$CH$_3$ | H | CF$_2$Cl | CH$_3$ |
| H | NHSO$_2$CF$_3$ | H | CF$_2$Cl | CH$_3$ |
| H | NHSO$_2$C$_2$H$_5$ | H | CF$_2$Cl | CH$_3$ |
| H | NHSO$_2$CH$_2$CF$_3$ | H | CF$_2$Cl | CH$_3$ |
| H | NHSO$_2$C$_3$H$_7$-n | H | CF$_2$Cl | CH$_3$ |
| H | NHSO$_2$C$_3$H$_7$-i | H | CF$_2$Cl | CH$_3$ |
| H | NHSO$_2$— | H | CF$_2$Cl | CH$_3$ |
| H | NHSO$_2$CH$_2$CH$_2$CH$_2$Cl | H | CF$_2$Cl | CH$_3$ |
| H | NHSO$_2$C$_4$H$_9$-n | H | CF$_2$Cl | CH$_3$ |
| H | NHSO$_2$C$_4$H$_9$-sec | H | CF$_2$Cl | CH$_3$ |
| H | NHSO$_2$C$_4$H$_9$-iso | H | CF$_2$Cl | CH$_3$ |
| H | NHSO$_2$C$_5$H$_{10}$-n | H | CF$_2$Cl | CH$_3$ |
| H | NHSO$_2$—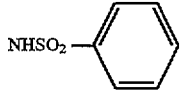 | H | CF$_2$Cl | CH$_3$ |
| H | NHSO$_2$—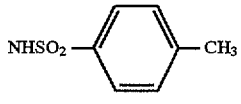—CH$_3$ | H | CF$_2$Cl | CH$_3$ |
| H | NHSO$_2$—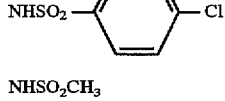—Cl | H | CF$_2$Cl | CH$_3$ |
| F | NHSO$_2$CH$_3$ | H | CF$_2$Cl | CH$_3$ |
| F | NHSO$_2$CF$_3$ | H | CF$_2$Cl | CH$_3$ |
| F | NHSO$_2$C$_2$H$_5$ | H | CF$_2$Cl | CH$_3$ |
| F | NHSO$_2$CH$_2$CF$_3$ | H | CF$_2$Cl | CH$_3$ |
| F | NHSO$_2$C$_3$H$_7$-n | H | CF$_2$Cl | CH$_3$ |
| F | NHSO$_2$C$_3$H$_7$-i | H | CF$_2$Cl | CH$_3$ |
| F | NHSO$_2$— | H | CF$_2$Cl | CH$_3$ |
| F | NHSO$_2$CH$_2$CH$_2$CH$_2$Cl | H | CF$_2$Cl | CH$_3$ |
| F | NHSO$_2$C$_4$H$_9$-n | H | CF$_2$Cl | CH$_3$ |
| F | NHSO$_2$C$_4$H$_9$-sec | H | CF$_2$Cl | CH$_3$ |
| F | NHSO$_2$C$_4$H$_9$-iso | H | CF$_2$Cl | CH$_3$ |
| F | NHSO$_2$C$_5$H$_{10}$-n | H | CF$_2$Cl | CH$_3$ |
| F | NHSO$_2$—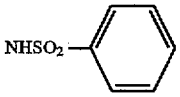 | H | CF$_2$Cl | CH$_3$ |
| F | NHSO$_2$—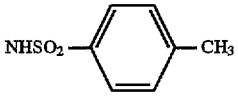—CH$_3$ | H | CF$_2$Cl | CH$_3$ |
| F | NHSO$_2$—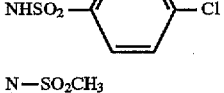—Cl | H | CF$_2$Cl | CH$_3$ |
| H | N—SO$_2$CH$_3$<br>\|<br>CH$_3$ | H | CF$_2$Cl | CH$_3$ |
| H | N—SO$_2$CF$_3$<br>\|<br>CH$_3$ | H | CF$_2$Cl | CH$_3$ |
| H | N—SO$_2$C$_2$H$_5$<br>\|<br>CH$_3$ | H | CF$_2$Cl | CH$_3$ |
| H | N—SO$_2$CH$_2$CF$_3$<br>\|<br>CH$_3$ | H | CF$_2$Cl | CH$_3$ |
| H | N—SO$_2$C$_3$H$_7$-n<br>\|<br>CH$_3$ | H | CF$_2$Cl | CH$_3$ |
| H | N—SO$_2$C$_3$H$_7$-i<br>\|<br>CH$_3$ | H | CF$_2$Cl | CH$_3$ |
| H | N—SO$_2$—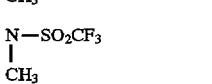<br>\|<br>CH$_3$ | H | CF$_2$Cl | CH$_3$ |
| H | N—SO$_2$CH$_2$CH$_2$CH$_2$Cl<br>\|<br>CH$_3$ | H | CF$_2$Cl | CH$_3$ |
| H | N—SO$_2$C$_4$H$_9$-n<br>\|<br>CH$_3$ | H | CF$_2$Cl | CH$_3$ |
| H | N—SO$_2$C$_4$H$_9$-sec<br>\|<br>CH$_3$ | H | CF$_2$Cl | CH$_3$ |
| H | N—SO$_2$C$_4$H$_9$-iso<br>\|<br>CH$_3$ | H | CF$_2$Cl | CH$_3$ |
| H | N—SO$_2$C$_5$H$_{10}$-n<br>\|<br>CH$_3$ | H | CF$_2$Cl | CH$_3$ |
| H | N—SO$_2$—phenyl<br>\|<br>CH$_3$ | H | CF$_2$Cl | CH$_3$ |
| H | N—SO$_2$—phenyl—CH$_3$<br>\|<br>CH$_3$ | H | CF$_2$Cl | CH$_3$ |

TABLE 1-continued

Examples of the compounds of the Formula (I)

| $R^1$ | $R^2$ | $R^3$ | $R^4$ | $R^5$ |
|---|---|---|---|---|
| H | N(CH₃)—SO₂—C₆H₄—Cl (p) | H | $CF_2Cl$ | $CH_3$ |
| F | N(CH₃)—SO₂CH₃ | H | $CF_2Cl$ | $CH_3$ |
| F | N(CH₃)—SO₂CF₃ | H | $CF_2Cl$ | $CH_3$ |
| F | N(CH₃)—SO₂C₂H₅ | H | $CF_2Cl$ | $CH_3$ |
| F | N(CH₃)—SO₂CH₂CF₃ | H | $CF_2Cl$ | $CH_3$ |
| F | N(CH₃)—SO₂C₃H₇-n | H | $CF_2Cl$ | $CH_3$ |
| F | N(CH₃)—SO₂C₃H₇-i | H | $CF_2Cl$ | $CH_3$ |
| F | N(CH₃)—SO₂-cyclopropyl | H | $CF_2Cl$ | $CH_3$ |
| F | N(CH₃)—SO₂CH₂CH₂CH₂Cl | H | $CF_2Cl$ | $CH_3$ |
| F | N(CH₃)—SO₂C₄H₉-n | H | $CF_2Cl$ | $CH_3$ |
| F | N(CH₃)—SO₂C₄H₉-sec | H | $CF_2Cl$ | $CH_3$ |
| F | N(CH₃)—SO₂C₄H₉-iso | H | $CF_2Cl$ | $CH_3$ |
| F | N(CH₃)—SO₂C₅H₁₀-n | H | $CF_2Cl$ | $CH_3$ |
| F | N(CH₃)—SO₂—C₆H₅ | H | $CF_2Cl$ | $CH_3$ |
| F | N(CH₃)—SO₂—C₆H₄—CH₃ (p) | H | $CF_2Cl$ | $CH_3$ |
| F | N(CH₃)—SO₂—C₆H₄—Cl (p) | H | $CF_2Cl$ | $CH_3$ |
| H | N(C₂H₅)—SO₂CH₃ | H | $CF_2Cl$ | $CH_3$ |
| H | N(C₂H₅)—SO₂CF₃ | H | $CF_2Cl$ | $CH_3$ |
| H | N(C₂H₅)—SO₂C₂H₅ | H | $CF_2Cl$ | $CH_3$ |
| H | N(C₂H₅)—SO₂CH₂CF₃ | H | $CF_2Cl$ | $CH_3$ |
| H | N(C₂H₅)—SO₂C₃H₇-n | H | $CF_2Cl$ | $CH_3$ |
| H | N(C₂H₅)—SO₂C₃H₇-i | H | $CF_2Cl$ | $CH_3$ |
| H | N(C₂H₅)—SO₂-cyclopropyl | H | $CF_2Cl$ | $CH_3$ |
| H | N(C₂H₅)—SO₂CH₂CH₂CH₂Cl | H | $CF_2Cl$ | $CH_3$ |
| H | N(C₂H₅)—SO₂C₄H₉-n | H | $CF_2Cl$ | $CH_3$ |
| H | N(C₂H₅)—SO₂C₄H₉-sec | H | $CF_2Cl$ | $CH_3$ |
| H | N(C₂H₅)—SO₂C₄H₉-iso | H | $CF_2Cl$ | $CH_3$ |
| H | N(C₂H₅)—SO₂C₅H₁₀-n | H | $CF_2Cl$ | $CH_3$ |
| H | N(C₂H₅)—SO₂—C₆H₅ | H | $CF_2Cl$ | $CH_3$ |
| H | N(C₂H₅)—SO₂—C₆H₄—CH₃ (p) | H | $CF_2Cl$ | $CH_3$ |
| H | N(C₂H₅)—SO₂—C₆H₄—Cl (p) | H | $CF_2Cl$ | $CH_3$ |
| F | N(C₂H₅)—SO₂CH₃ | H | $CF_2Cl$ | $CH_3$ |
| F | N(C₂H₅)—SO₂CF₃ | H | $CF_2Cl$ | $CH_3$ |
| F | N(C₂H₅)—SO₂C₂H₅ | H | $CF_2Cl$ | $CH_3$ |
| F | N(C₂H₅)—SO₂CH₂CF₃ | H | $CF_2Cl$ | $CH_3$ |
| F | N(C₂H₅)—SO₂C₃H₇-n | H | $CF_2Cl$ | $CH_3$ |

TABLE 1-continued

Examples of the compounds of the Formula (I)

| R¹ | R² | R³ | R⁴ | R⁵ |
|---|---|---|---|---|
| F | N(C₂H₅)—SO₂C₃H₇-i | H | CF₂Cl | CH₃ |
| F | N(C₂H₅)—SO₂-cyclopropyl | H | CF₂Cl | CH₃ |
| F | N(C₂H₅)—SO₂CH₂CH₂CH₂Cl | H | CF₂Cl | CH₃ |
| F | N(C₂H₅)—SO₂C₄H₉-n | H | CF₂Cl | CH₃ |
| F | N(C₂H₅)—SO₂C₄H₉-sec | H | CF₂Cl | CH₃ |
| F | N(C₂H₅)—SO₂C₄H₉-iso | H | CF₂Cl | CH₃ |
| F | N(C₂H₅)—SO₂C₅H₁₀-n | H | CF₂Cl | CH₃ |
| F | N(C₂H₅)—SO₂-phenyl | H | CF₂Cl | CH₃ |
| F | N(C₂H₅)—SO₂-(4-CH₃-phenyl) | H | CF₂Cl | CH₃ |
| F | N(C₂H₅)—SO₂-(4-Cl-phenyl) | H | CF₂Cl | CH₃ |
| F | N(C₂H₅)—SO₂CH₃ | H | CF₂Cl | C₂H₅ |
| F | N(C₂H₅)—SO₂CF₃ | H | CF₂Cl | C₂H₅ |
| F | N(C₂H₅)—SO₂C₂H₅ | H | CF₂Cl | C₂H₅ |
| F | N(C₂H₅)—SO₂CH₂CF₃ | H | CF₂Cl | C₂H₅ |
| F | N(C₂H₅)—SO₂C₃H₇-n | H | CF₂Cl | C₂H₅ |
| F | N(C₂H₅)—SO₂C₃H₇-i | H | CF₂Cl | C₂H₅ |
| F | N(C₂H₅)—SO₂-cyclopropyl | H | CF₂Cl | C₂H₅ |
| F | N(C₂H₅)—SO₂CH₂CH₂CH₂Cl | H | CF₂Cl | C₂H₅ |
| F | N(C₂H₅)—SO₂C₄H₉-n | H | CF₂Cl | C₂H₅ |
| F | N(C₂H₅)—SO₂C₄H₉-sec | H | CF₂Cl | C₂H₅ |
| F | N(C₂H₅)—SO₂C₄H₉-iso | H | CF₂Cl | C₂H₅ |
| F | N(C₂H₅)—SO₂C₅H₁₀-n | H | CF₂Cl | C₂H₅ |
| F | N(C₂H₅)—SO₂-phenyl | H | CF₂Cl | C₂H₅ |
| F | N(C₂H₅)—SO₂-(4-CH₃-phenyl) | H | CF₂Cl | C₂H₅ |
| F | N(C₂H₅)—SO₂-(4-Cl-phenyl) | H | CF₂Cl | C₂H₅ |
| H | NHSO₂CH₃ | H | CF₂Cl | C₂H₅ |
| H | NHSO₂CF₃ | H | CF₂Cl | C₂H₅ |
| H | NHSO₂C₂H₅ | H | CF₂Cl | C₂H₅ |
| H | NHSO₂CH₂CF₃ | H | CF₂Cl | C₂H₅ |
| H | NHSO₂C₃H₇-n | H | CF₂Cl | C₂H₅ |
| H | NHSO₂C₃H₇-i | H | CF₂Cl | C₂H₅ |
| H | NHSO₂-cyclopropyl | H | CF₂Cl | C₂H₅ |
| H | NHSO₂CH₂CH₂CH₂Cl | H | CF₂Cl | C₂H₅ |
| H | NHSO₂C₄H₉-n | H | CF₂Cl | C₂H₅ |
| H | NHSO₂C₄H₉-sec | H | CF₂Cl | C₂H₅ |
| H | NHSO₂C₄H₉-iso | H | CF₂Cl | C₂H₅ |
| H | NHSO₂C₅H₁₀-n | H | CF₂Cl | C₂H₅ |
| H | NHSO₂-phenyl | H | CF₂Cl | C₂H₅ |
| H | NHSO₂-(4-CH₃-phenyl) | H | CF₂Cl | C₂H₅ |
| H | NHSO₂-(4-Cl-phenyl) | H | CF₂Cl | C₂H₅ |
| F | NHSO₂CH₃ | H | CF₂Cl | C₂H₅ |
| F | NHSO₂CF₃ | H | CF₂Cl | C₂H₅ |
| F | NHSO₂C₂H₅ | H | CF₂Cl | C₂H₅ |
| F | NHSO₂CH₂CF₃ | H | CF₂Cl | C₂H₅ |
| F | NHSO₂C₃H₇-n | H | CF₂Cl | C₂H₅ |
| F | NHSO₂C₃H₇-i | H | CF₂Cl | C₂H₅ |
| F | NHSO₂-cyclopropyl | H | CF₂Cl | C₂H₅ |
| F | NHSO₂CH₂CH₂CH₂Cl | H | CF₂Cl | C₂H₅ |

TABLE 1-continued

Examples of the compounds of the Formula (I)

| R¹ | R² | R³ | R⁴ | R⁵ |
|---|---|---|---|---|
| F | NHSO$_2$C$_4$H$_9$-n | H | CF$_2$Cl | C$_2$H$_5$ |
| F | NHSO$_2$C$_4$H$_9$-sec | H | CF$_2$Cl | C$_2$H$_5$ |
| F | NHSO$_2$C$_4$H$_9$-iso | H | CF$_2$Cl | C$_2$H$_5$ |
| F | NHSO$_2$C$_5$H$_{10}$-n | H | CF$_2$Cl | C$_2$H$_5$ |
| F | 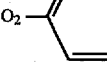 | H | CF$_2$Cl | C$_2$H$_5$ |
| F | 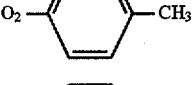 | H | CF$_2$Cl | C$_2$H$_5$ |
| F | 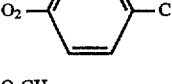 | H | CF$_2$Cl | C$_2$H$_5$ |
| H | NHSO$_2$CH$_3$ | CH$_3$ | CF$_2$Cl | CH$_3$ |
| H | NHSO$_2$CF$_3$ | CH$_3$ | CF$_2$Cl | CH$_3$ |
| H | NHSO$_2$C$_2$H$_5$ | CH$_3$ | CF$_2$Cl | CH$_3$ |
| H | NHSO$_2$CH$_2$CF$_3$ | CH$_3$ | CF$_2$Cl | CH$_3$ |
| H | NHSO$_2$C$_3$H$_7$-n | CH$_3$ | CF$_2$Cl | CH$_3$ |
| H | NHSO$_2$C$_3$H$_7$-i | CH$_3$ | CF$_2$Cl | CH$_3$ |
| H | NHSO$_2$-⊳ (cyclopropyl) | CH$_3$ | CF$_2$Cl | CH$_3$ |
| H | NHSO$_2$CH$_2$CH$_2$CH$_2$Cl | CH$_3$ | CF$_2$Cl | CH$_3$ |
| H | NHSO$_2$C$_4$H$_9$-n | CH$_3$ | CF$_2$Cl | CH$_3$ |
| H | NHSO$_2$C$_4$H$_9$-sec | CH$_3$ | CF$_2$Cl | CH$_3$ |
| H | NHSO$_2$C$_4$H$_9$-iso | CH$_3$ | CF$_2$Cl | CH$_3$ |
| H | NHSO$_2$C$_5$H$_{10}$-n | CH$_3$ | CF$_2$Cl | CH$_3$ |
| H |  | CH$_3$ | CF$_2$Cl | CH$_3$ |
| H | 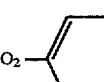 | CH$_3$ | CF$_2$Cl | CH$_3$ |
| H | 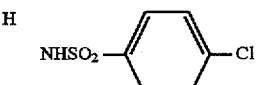 | CH$_3$ | CF$_2$Cl | CH$_3$ |
| F | NHSO$_2$CH$_3$ | CH$_3$ | CF$_2$Cl | CH$_3$ |
| F | NHSO$_2$CF$_3$ | CH$_3$ | CF$_2$Cl | CH$_3$ |
| F | NHSO$_2$C$_2$H$_5$ | CH$_3$ | CF$_2$Cl | CH$_3$ |
| F | NHSO$_2$CH$_2$CF$_3$ | CH$_3$ | CF$_2$Cl | CH$_3$ |
| F | NHSO$_2$C$_3$H$_7$-n | CH$_3$ | CF$_2$Cl | CH$_3$ |
| F | NHSO$_2$C$_3$H$_7$-i | CH$_3$ | CF$_2$Cl | CH$_3$ |
| F | NHSO$_2$-⊳ | CH$_3$ | CF$_2$Cl | CH$_3$ |
| F | NHSO$_2$CH$_2$CH$_2$CH$_2$Cl | CH$_3$ | CF$_2$Cl | CH$_3$ |
| F | NHSO$_2$C$_4$H$_9$-n | CH$_3$ | CF$_2$Cl | CH$_3$ |
| F | NHSO$_2$C$_4$H$_9$-sec | CH$_3$ | CF$_2$Cl | CH$_3$ |
| F | NHSO$_2$C$_4$H$_9$-iso | CH$_3$ | CF$_2$Cl | CH$_3$ |
| F | NHSO$_2$C$_5$H$_{10}$-n | CH$_3$ | CF$_2$Cl | CH$_3$ |
| F | 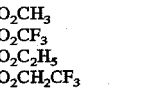 | CH$_3$ | CF$_2$Cl | CH$_3$ |
| F |  | CH$_3$ | CF$_2$Cl | CH$_3$ |
| F | 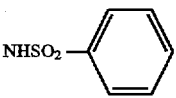 | CH$_3$ | CF$_2$Cl | CH$_3$ |
| F | NHSO$_2$CH$_3$ | Cl | CF$_2$Cl | CH$_3$ |
| F | NHSO$_2$CF$_3$ | Cl | CF$_2$Cl | CH$_3$ |
| F | NHSO$_2$C$_2$H$_5$ | Cl | CF$_2$Cl | CH$_3$ |
| F | NHSO$_2$CH$_2$CF$_3$ | Cl | CF$_2$Cl | CH$_3$ |
| F | NHSO$_2$C$_3$H$_7$-n | Cl | CF$_2$Cl | CH$_3$ |
| F | NHSO$_2$C$_3$H$_7$-i | Cl | CF$_2$Cl | CH$_3$ |
| F | NHSO$_2$-⊳ | Cl | CF$_2$Cl | CH$_3$ |
| F | NHSO$_2$CH$_2$CH$_2$CH$_2$Cl | Cl | CF$_2$Cl | CH$_3$ |
| F | NHSO$_2$C$_4$H$_9$-n | Cl | CF$_2$Cl | CH$_3$ |
| F | NHSO$_2$C$_4$H$_9$-sec | Cl | CF$_2$Cl | CH$_3$ |
| F | NHSO$_2$C$_4$H$_9$-iso | Cl | CF$_2$Cl | CH$_3$ |
| F | NHSO$_2$C$_5$H$_{10}$-n | Cl | CF$_2$Cl | CH$_3$ |
| F | NHSO$_2$-C$_6$H$_5$ | Cl | CF$_2$Cl | CH$_3$ |
| F | NHSO$_2$-C$_6$H$_4$-CH$_3$ | Cl | CF$_2$Cl | CH$_3$ |
| F | NHSO$_2$-C$_6$H$_4$-Cl | Cl | CF$_2$Cl | CH$_3$ |
| F | NHSO$_2$CH$_3$ | F | CF$_2$Cl | CH$_3$ |
| F | NHSO$_2$CF$_3$ | F | CF$_2$Cl | CH$_3$ |
| F | NHSO$_2$C$_2$H$_5$ | F | CF$_2$Cl | CH$_3$ |
| F | NHSO$_2$CH$_2$CF$_3$ | F | CF$_2$Cl | CH$_3$ |
| F | NHSO$_2$C$_3$H$_7$-n | F | CF$_2$Cl | CH$_3$ |
| F | NHSO$_2$C$_3$H$_7$-i | F | CF$_2$Cl | CH$_3$ |
| F | NHSO$_2$-⊳ | F | CF$_2$Cl | CH$_3$ |
| F | NHSO$_2$CH$_2$CH$_2$CH$_2$Cl | F | CF$_2$Cl | CH$_3$ |
| F | NHSO$_2$C$_4$H$_9$-n | F | CF$_2$Cl | CH$_3$ |
| F | NHSO$_2$C$_4$H$_9$-sec | F | CF$_2$Cl | CH$_3$ |
| F | NHSO$_2$C$_4$H$_9$-iso | F | CF$_2$Cl | CH$_3$ |
| F | NHSO$_2$C$_5$H$_{10}$-n | F | CF$_2$Cl | CH$_3$ |
| F | NHSO$_2$-C$_6$H$_5$ | F | CF$_2$Cl | CH$_3$ |
| F | NHSO$_2$-C$_6$H$_4$-CH$_3$ | F | CF$_2$Cl | CH$_3$ |
| F | NHSO$_2$-C$_6$H$_4$-Cl | F | CF$_2$Cl | CH$_3$ |

TABLE 1-continued

Examples of the compounds of the Formula (I)

| R¹ | R² | R³ | R⁴ | R⁵ |
|---|---|---|---|---|
| F | N(CH₃)—SO₂CH₃ | CH₃ | CF₂Cl | CH₃ |
| F | N(CH₃)—SO₂CF₃ | CH₃ | CF₂Cl | CH₃ |
| F | N(CH₃)—SO₂C₂H₅ | CH₃ | CF₂Cl | CH₃ |
| F | N(CH₃)—SO₂CH₂CF₃ | CH₃ | CF₂Cl | CH₃ |
| F | N(CH₃)—SO₂C₃H₇-n | CH₃ | CF₂Cl | CH₃ |
| F | N(CH₃)—SO₂C₃H₇-i | CH₃ | CF₂Cl | CH₃ |
| F | N(CH₃)—SO₂-cyclopropyl | CH₃ | CF₂Cl | CH₃ |
| F | N(CH₃)—SO₂CH₂CH₂CH₂Cl | CH₃ | CF₂Cl | CH₃ |
| F | N(CH₃)—SO₂C₄H₉-n | CH₃ | CF₂Cl | CH₃ |
| F | N(CH₃)—SO₂C₄H₉-sec | CH₃ | CF₂Cl | CH₃ |
| F | N(CH₃)—SO₂C₄H₉-iso | CH₃ | CF₂Cl | CH₃ |
| F | N(CH₃)—SO₂C₅H₁₀-n | CH₃ | CF₂Cl | CH₃ |
| F | N(CH₃)—SO₂-phenyl | CH₃ | CF₂Cl | CH₃ |
| F | N(CH₃)—SO₂-(4-CH₃-phenyl) | CH₃ | CF₂Cl | CH₃ |
| F | N(CH₃)—SO₂-(4-Cl-phenyl) | CH₃ | CF₂Cl | CH₃ |
| F | N(CH₃)—SO₂CH₃ | Cl | CF₂Cl | CH₃ |
| F | N(CH₃)—SO₂CF₃ | Cl | CF₂Cl | CH₃ |
| F | N(CH₃)—SO₂C₂H₅ | Cl | CF₂Cl | CH₃ |
| F | N(CH₃)—SO₂CH₂CF₃ | Cl | CF₂Cl | CH₃ |
| F | N(CH₃)—SO₂C₃H₇-n | Cl | CF₂Cl | CH₃ |
| F | N(CH₃)—SO₂C₃H₇-i | Cl | CF₂Cl | CH₃ |
| F | N(CH₃)—SO₂-cyclopropyl | Cl | CF₂Cl | CH₃ |
| F | N(CH₃)—SO₂CH₂CH₂CH₂Cl | Cl | CF₂Cl | CH₃ |
| F | N(CH₃)—SO₂C₄H₉-n | Cl | CF₂Cl | CH₃ |
| F | N(CH₃)—SO₂C₄H₉-sec | Cl | CF₂Cl | CH₃ |
| F | N(CH₃)—SO₂C₄H₉-iso | Cl | CF₂Cl | CH₃ |
| F | N(CH₃)—SO₂C₅H₁₀-n | Cl | CF₂Cl | CH₃ |
| F | N(CH₃)—SO₂-phenyl | Cl | CF₂Cl | CH₃ |
| F | N(CH₃)—SO₂-(4-CH₃-phenyl) | Cl | CF₂Cl | CH₃ |
| F | N(CH₃)—SO₂-(4-Cl-phenyl) | Cl | CF₂Cl | CH₃ |
| F | N(CH₃)—SO₂CH₃ | F | CF₂Cl | CH₃ |
| F | N(CH₃)—SO₂CF₃ | F | CF₂Cl | CH₃ |
| F | N(CH₃)—SO₂C₂H₅ | F | CF₂Cl | CH₃ |
| F | N(CH₃)—SO₂CH₂CF₃ | F | CF₂Cl | CH₃ |
| F | N(CH₃)—SO₂C₃H₇-n | F | CF₂Cl | CH₃ |
| F | N(CH₃)—SO₂C₃H₇-i | F | CF₂Cl | CH₃ |

TABLE 1-continued

Examples of the compounds of the Formula (I)

| R¹ | R² | R³ | R⁴ | R⁵ |
|---|---|---|---|---|
| F | N(CH₃)—SO₂-cyclopropyl | F | CF₂Cl | CH₃ |
| F | N(CH₃)—SO₂CH₂CH₂CH₂Cl | F | CF₂Cl | CH₃ |
| F | N(CH₃)—SO₂C₄H₉-n | F | CF₂Cl | CH₃ |
| F | N(CH₃)—SO₂C₄H₉-sec | F | CF₂Cl | CH₃ |
| F | N(CH₃)—SO₂C₄H₉-iso | F | CF₂Cl | CH₃ |
| F | N(CH₃)—SO₂C₅H₁₀-n | F | CF₂Cl | CH₃ |
| F | N(CH₃)—SO₂—C₆H₅ | F | CF₂Cl | CH₃ |
| F | N(CH₃)—SO₂—C₆H₄—CH₃ | F | CF₂Cl | CH₃ |
| F | N(CH₃)—SO₂—C₆H₄—Cl | F | CF₂Cl | CH₃ |
| F | NHSO₂CH₃ | H | CF₂Cl | NH₂ |
| F | NHSO₂CF₃ | H | CF₂Cl | NH₂ |
| F | NHSO₂C₂H₅ | H | CF₂Cl | NH₂ |
| F | NHSO₂CH₂CF₃ | H | CF₂Cl | NH₂ |
| F | NHSO₂C₃H₇-n | H | CF₂Cl | NH₂ |
| F | NHSO₂C₃H₇-i | H | CF₂Cl | NH₂ |
| F | NHSO₂-cyclopropyl | H | CF₂Cl | NH₂ |
| F | NHSO₂CH₂CH₂CH₂Cl | H | CF₂Cl | NH₂ |
| F | NHSO₂C₄H₉-n | H | CF₂Cl | NH₂ |
| F | NHSO₂C₄H₉-sec | H | CF₂Cl | NH₂ |
| F | NHSO₂C₄H₉-iso | H | CF₂Cl | NH₂ |
| F | NHSO₂C₅H₁₀-n | H | CF₂Cl | NH₂ |
| F | NHSO₂—C₆H₅ | H | CF₂Cl | NH₂ |
| F | NHSO₂—C₆H₄—CH₃ | H | CF₂Cl | NH₂ |
| F | NHSO₂—C₆H₄—Cl | H | CF₂Cl | NH₂ |
| F | N(CH₃)—SO₂CH₃ | H | CF₂Cl | NH₂ |
| F | N(CH₃)—SO₂CF₃ | H | CF₂Cl | NH₂ |
| F | N(CH₃)—SO₂C₂H₅ | H | CF₂Cl | NH₂ |
| F | N(CH₃)—SO₂CH₂CF₃ | H | CF₂Cl | NH₂ |
| F | N(CH₃)—SO₂C₃H₇-n | H | CF₂Cl | NH₂ |
| F | N(CH₃)—SO₂C₃H₇-i | H | CF₂Cl | NH₂ |
| F | N(CH₃)—SO₂-cyclopropyl | H | CF₂Cl | NH₂ |
| F | N(CH₃)—SO₂CH₂CH₂CH₂Cl | H | CF₂Cl | NH₂ |
| F | N(CH₃)—SO₂C₄H₉-n | H | CF₂Cl | NH₂ |
| F | N(CH₃)—SO₂C₄H₉-sec | H | CF₂Cl | NH₂ |
| F | N(CH₃)—SO₂C₄H₉-iso | H | CF₂Cl | NH₂ |
| F | N(CH₃)—SO₂C₅H₁₀-n | H | CF₂Cl | NH₂ |
| F | N(CH₃)—SO₂—C₆H₅ | H | CF₂Cl | NH₂ |
| F | N(CH₃)—SO₂—C₆H₄—CH₃ | H | CF₂Cl | NH₂ |
| F | N(CH₃)—SO₂—C₆H₄—Cl | H | CF₂Cl | NH₂ |
| F | NHSO₂CH₃ | CH₃ | CF₂Cl | NH₂ |
| F | NHSO₂CF₃ | CH₃ | CF₂Cl | NH₂ |
| F | NHSO₂C₂H₅ | CH₃ | CF₂Cl | NH₂ |
| F | NHSO₂CH₂CF₃ | CH₃ | CF₂Cl | NH₂ |
| F | NHSO₂C₃H₇-n | CH₃ | CF₂Cl | NH₂ |
| F | NHSO₂C₃H₇-i | CH₃ | CF₂Cl | NH₂ |
| F | NHSO₂-cyclopropyl | CH₃ | CF₂Cl | NH₂ |
| F | NHSO₂CH₂CH₂CH₂Cl | CH₃ | CF₂Cl | NH₂ |
| F | NHSO₂C₄H₉-n | CH₃ | CF₂Cl | NH₂ |
| F | NHSO₂C₄H₉-sec | CH₃ | CF₂Cl | NH₂ |
| F | NHSO₂C₄H₉-iso | CH₃ | CF₂Cl | NH₂ |
| F | NHSO₂C₅H₁₀-n | CH₃ | CF₂Cl | NH₂ |

TABLE 1-continued

Examples of the compounds of the Formula (I)

| R¹ | R² | R³ | R⁴ | R⁵ |
|---|---|---|---|---|
| F | NHSO₂—C₆H₅ | CH₃ | CF₂Cl | NH₂ |
| F | NHSO₂—C₆H₄—CH₃ | CH₃ | CF₂Cl | NH₂ |
| F | NHSO₂—C₆H₄—Cl | CH₃ | CF₂Cl | NH₂ |
| F | NHSO₂CH₃ | H | CF₂Cl | CHF₂ |
| F | NHSO₂CF₃ | H | CF₂Cl | CHF₂ |
| F | NHSO₂C₂H₅ | H | CF₂Cl | CHF₂ |
| F | NHSO₂CH₂CF₃ | H | CF₂Cl | CHF₂ |
| F | NHSO₂C₃H₇-n | H | CF₂Cl | CHF₂ |
| F | NHSO₂CH₂CF₃ | CH₃ | CF₂Cl | NH₂ |
| F | NHSO₂C₃H₇-n | CH₃ | CF₂Cl | NH₂ |
| F | NHSO₂C₃H₇-i | CH₃ | CF₂Cl | NH₂ |
| F | NHSO₂—cyclopropyl | CH₃ | CF₂Cl | NH₂ |
| F | NHSO₂CH₂CH₂CH₂Cl | CH₃ | CF₂Cl | NH₂ |
| F | NHSO₂C₄H₉-n | CH₃ | CF₂Cl | NH₂ |
| F | NHSO₂C₄H₉-sec | CH₃ | CF₂Cl | NH₂ |
| F | NHSO₂C₄H₉-iso | CH₃ | CF₂Cl | NH₂ |
| F | NHSO₂C₅H₁₀-n | CH₃ | CF₂Cl | NH₂ |
| F | NHSO₂—C₆H₅ | CH₃ | CF₂Cl | NH₂ |
| F | NHSO₂—C₆H₄—CH₃ | CH₃ | CF₂Cl | NH₂ |
| F | NHSO₂—C₆H₄—Cl | CH₃ | CF₂Cl | NH₂ |
| F | NHSO₂CH₃ | H | CF₂Cl | CHF₂ |
| F | NHSO₂CF₃ | H | CF₂Cl | CHF₂ |
| F | NHSO₂C₂H₅ | H | CF₂Cl | CHF₂ |
| F | NHSO₂CH₂CF₃ | H | CF₂Cl | CHF₂ |
| F | NHSO₂C₃H₇-n | H | CF₂Cl | CHF₂ |
| F | NHSO₂C₃H₇-i | H | CF₂Cl | CHF₂ |
| F | NHSO₂—cyclopropyl | H | CF₂Cl | CHF₂ |
| F | NHSO₂CH₂CH₂CH₂Cl | H | CF₂Cl | CHF₂ |
| F | NHSO₂C₄H₉-n | H | CF₂Cl | CHF₂ |
| F | NHSO₂C₄H₉-sec | H | CF₂Cl | CHF₂ |
| F | NHSO₂C₄H₉-iso | H | CF₂Cl | CHF₂ |
| F | NHSO₂C₅H₁₀-n | H | CF₂Cl | CHF₂ |
| F | NHSO₂—C₆H₅ | H | CF₂Cl | CHF₂ |
| F | NHSO₂—C₆H₄—CH₃ | H | CF₂Cl | CHF₂ |
| F | NHSO₂—C₆H₄—Cl | H | CF₂Cl | CHF₂ |
| F | N(CH₃)—SO₂CH₃ | H | CF₂Cl | CHF₂ |
| F | N(CH₃)—SO₂CF₃ | H | CF₂Cl | CHF₂ |
| F | N(CH₃)—SO₂C₂H₅ | H | CF₂Cl | CHF₂ |
| F | N(CH₃)—SO₂CH₂CF₃ | H | CF₂Cl | CHF₂ |
| F | N(CH₃)—SO₂C₃H₇-n | H | CF₂Cl | CHF₂ |
| F | N(CH₃)—SO₂C₃H₇-i | H | CF₂Cl | CHF₂ |
| F | N(CH₃)—SO₂—cyclopropyl | H | CF₂Cl | CHF₂ |
| F | N(CH₃)—SO₂CH₂CH₂CH₂Cl | H | CF₂Cl | CHF₂ |
| F | N(CH₃)—SO₂C₄H₉-n | H | CF₂Cl | CHF₂ |
| F | N(CH₃)—SO₂C₄H₉-sec | H | CF₂Cl | CHF₂ |
| F | N(CH₃)—SO₂C₄H₉-iso | H | CF₂Cl | CHF₂ |
| F | N(CH₃)—SO₂C₅H₁₀-n | H | CF₂Cl | CHF₂ |
| F | N(CH₃)—SO₂—C₆H₅ | H | CF₂Cl | CHF₂ |
| F | N(CH₃)—SO₂—C₆H₄—CH₃ | H | CF₂Cl | CHF₂ |
| F | N(CH₃)—SO₂—C₆H₄—Cl | H | CF₂Cl | CHF₂ |
| F | NHSO₂CH₃ | CH₃ | CF₂Cl | CHF₂ |
| F | NHSO₂CF₃ | CH₃ | CF₂Cl | CHF₂ |
| F | NHSO₂C₂H₅ | CH₃ | CF₂Cl | CHF₂ |

TABLE 1-continued

Examples of the compounds of the Formula (I)

| R¹ | R² | R³ | R⁴ | R⁵ |
|---|---|---|---|---|
| F | NHSO$_2$CH$_2$CF$_3$ | CH$_3$ | CF$_2$Cl | CHF$_2$ |
| F | NHSO$_2$C$_3$H$_7$-n | CH$_3$ | CF$_2$Cl | CHF$_2$ |
| F | NHSO$_2$C$_3$H$_7$-i | CH$_3$ | CF$_2$Cl | CHF$_2$ |
| F | NHSO$_2$—cyclopropyl | CH$_3$ | CF$_2$Cl | CHF$_2$ |
| F | NHSO$_2$CH$_2$CH$_2$CH$_2$Cl | CH$_3$ | CF$_2$Cl | CHF$_2$ |
| F | NHSO$_2$C$_4$H$_9$-n | CH$_3$ | CF$_2$Cl | CHF$_2$ |
| F | NHSO$_2$C$_4$H$_9$-sec | CH$_3$ | CF$_2$Cl | CHF$_2$ |
| F | NHSO$_2$C$_4$H$_9$-iso | CH$_3$ | CF$_2$Cl | CHF$_2$ |
| F | NHSO$_2$C$_5$H$_{10}$-n | CH$_3$ | CF$_2$Cl | CHF$_2$ |
| F | NHSO$_2$—phenyl | CH$_3$ | CF$_2$Cl | CHF$_2$ |
| F | NHSO$_2$—C$_6$H$_4$—CH$_3$ | CH$_3$ | CF$_2$Cl | CHF$_2$ |
| F | NHSO$_2$—C$_6$H$_4$—Cl | CH$_3$ | CF$_2$Cl | CHF$_2$ |

If, for example, methyl 3-aminocrotonate and 4-cyano-2,5-difluorophenyl isocyanate are used as starting substances, the course of the reaction in process (a) according to the invention can be outlined by the following equation:

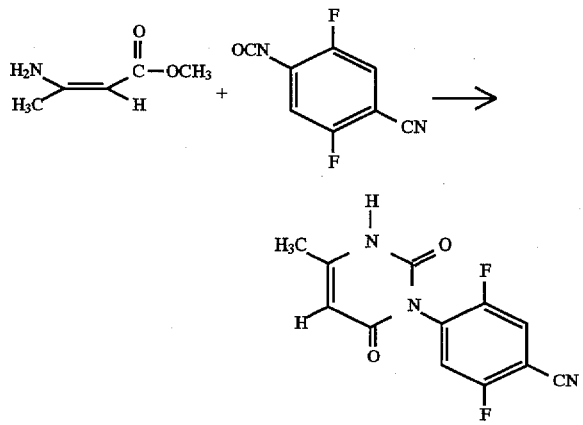

If, for example, 1-(3-chloro-4-cyano-phenyl)-3,6-dihydro-2,6-dioxo-4-trifluoromethyl-1(2H)-pyrimidine and methyl bromide are used as starting substances, the course of the reaction in process (b) according to the invention can be outlined by the following equation:

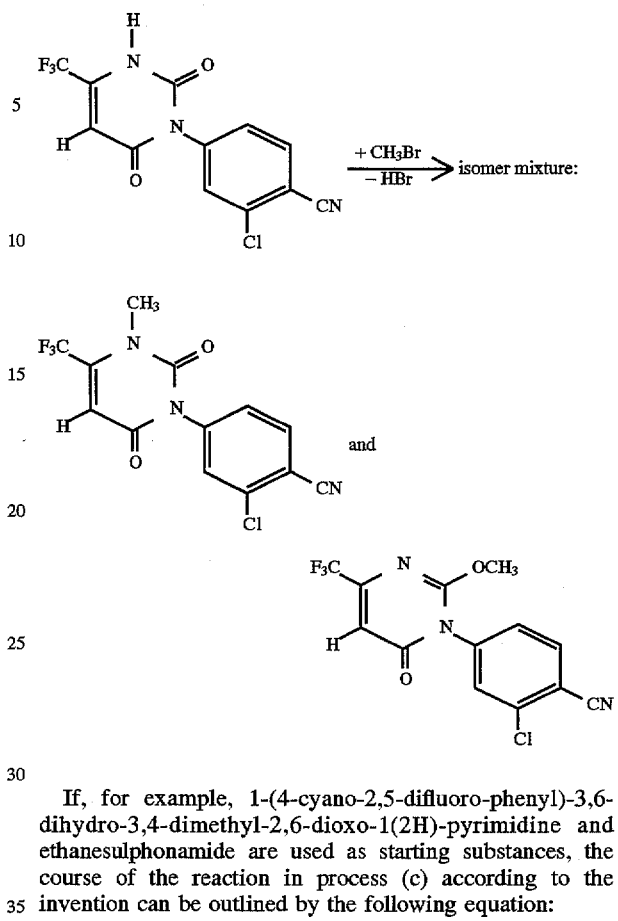

If, for example, 1-(4-cyano-2,5-difluoro-phenyl)-3,6-dihydro-3,4-dimethyl-2,6-dioxo-1(2H)-pyrimidine and ethanesulphonamide are used as starting substances, the course of the reaction in process (c) according to the invention can be outlined by the following equation:

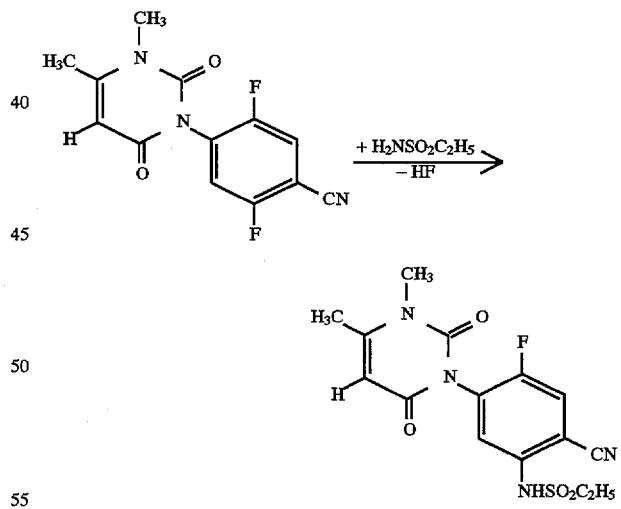

Formula (II) provides a general definition of the aminoalkenoic esters to be used as starting substances in process (a) according to the invention for the preparation of compounds of the formula (I).

In Formula (II) R3 and R⁴, preferably, or in particular, have those meanings which have already been mentioned above in connection with the description of the compounds of the formula (I) according to the invention as being preferred, or particularly preferred, for R³ and R⁴.

R preferably represents C$_1$–C$_4$-alkyl, phenyl or benzyl, in particular methyl or phenyl.

The starting substances of formula (II) are known and/or can be prepared by known processes (cf. J. Heterocycl. Chem. 9 (1972), 513–522).

Formula (III) provides a general definition of the cyanoaryl isocyanates furthermore to be used as starting substances in process (a) according to the invention.

In Formula (III), $R^1$ and $R^2$ preferably, or in particular, have those meanings which have already been mentioned above in connection with the description of compounds of the formula (I) according to the invention as being preferred, or particularly preferred, for $R^1$ and, $R^2$. The cyanoaryl isocyanates of the general formula (III) were hitherto not known from the literature and, being new substances, are the subject of the present application.

The new cyanoaryl isocyanates of the formula (III) are obtained when cyanoarylamines of the general formula (VIII)

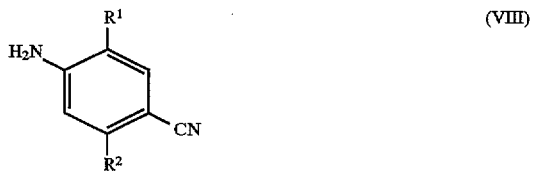

in which $R^1$ and $R^2$ have the abovementioned meanings, are reacted with phosgene in the presence of a diluent, such as, for example, chlorobenzene, at temperatures between −20° C. and +150° C. (cf. the preparation examples).

The cyanoarylurethanes optionally to be used as starting materials in process (a) according to the invention are defined in general by the formula (IV). In the formula (IV), $R^1$ and $R^2$ preferably or in particular have those meanings which have already been mentioned above in connection with the description of the compounds of the formula (I) as being preferred or particularly preferable for $R^1$ and $R^2$; R preferably represents $C_1$–$C_4$-alkyl, phenyl or benzyl, in particular methyl or phenyl.

The cyanoarylurethanes of the general formula (IV) are not yet known from the literature; as novel substances, they are the subject of the present application.

The novel cyanoarylurethanes of the formula (IV) are obtained if cyanoarylamines of the general formula (VIII) —above—are reacted with chlorocarbonyl compounds of the general formula (IX)

$$RO—CO—Cl \quad \text{(IX)}$$

in which

R has the abovementioned meaning, optionally in the presence of an acid acceptor, such as, for example, pyridine, and optionally in the presence of a diluent, such as, for example, methylene chloride, at temperatures between 0° C. and 100° C. (cf. preparation examples).

Process (a) according to the invention for the preparation of the new N-cyanoaryl-nitrogen heterocycles of the formula (I) is preferably carried out using diluents. Diluents which are suitable are virtually all inert organic solvents. These preferably include aliphatic and aromatic, optionally halogenated hydrocarbons, such as pentane, hexane, heptane, cyclohexane, petroleum ether, benzine, ligroin, benzene, toluene, xylene, methylene chloride, ethylene chloride, chloroform, tetrachloromethane, chlorobenzene and o-dichlorobenzene, ethers, such as diethyl ether, dibutyl ether, glycol dimethyl ether, diglycol dimethyl ether, tetrahydrofuran and dioxane, ketones, such as acetone, methyl ethyl ketone, methyl isopropyl ketone and methyl isobutyl ketone, esters, such as methyl acetate and ethyl acetate, nitriles, such as, for example, acetonitrile and propionitrile, amides, such as, for example, dimethylformamide, dimethylacetamide and N-methylpyrrolidone, and also dimethyl sulphoxide, tetramethylene sulphone and hexamethylphosphoric triamide.

Process (a) according to the invention is preferably carried out in the presence of a reaction auxiliary. Suitable as reaction auxiliaries are mainly acid acceptors. The following are preferably suitable: alkali metal hydrides and alkaline earth metal hydrides, such as lithium hydride, sodium hydride, potassium hydride and calcium hydride, alkali metal hydroxides and alkaline earth metal hydroxides, such as lithium hydroxide, sodium hydroxide, potassium hydroxide and calcium hydroxide, alkali metal carbonates, alkali metal hydrogen carbonates, alkaline earth metal carbonates and alkaline earth metal hydrogen carbonates, such as sodium carbonate, sodium hydrogen carbonate, potassium carbonate or potassium hydrogen carbonate, and calcium carbonate, alkali metal acetates, such as sodium acetate and potassium acetate, alkali metal alcoholates, such as sodium methylate, sodium ethylate, sodium propylate, sodium isopropylate, sodium butylate, sodium isobutylate, sodium tertbutylate, potassium methylate, potassium ethylate, potassium propylate, potassium isopropylate, potassium butylate, potassium isobutylate and potassium tertbutylate, furthermore basic nitrogen compounds, such as trimethylamine, triethylamine, tripropylamine, tributylamine, diisobutylamine, dicyclohexylamine, ethyldiisopropylamine, ethyldicyclohexylamine, N,N-dimethylbenzylamine, N,N-dimethyl-aniline, pyridine, 2-methyl-, 3-methyl-, 4-methyl-, 2,4-dimethyl-, 2,6-dimethyl-, 2-ethyl-, 4-ethyl- and 5-ethyl-2-methyl-pyridine, 1,5-diazabicyclo[4,3,0]-non-5-ene (DBN), 1,8-diazabicyclo-[5,4,0]-undec-7-ene (DBU) and 1,4-diazabicyclo-[2,2,2]-octane (DABCO).

When carrying out process (a) according to the invention, the reaction temperatures can be varied within a substantial range. In general the process is carried out at temperatures between −120° C. and +100° C., preferably at temperatures between −70° C. and +80° C.

In general, process (a) according to the invention is carried out under atmospheric pressure. However, it is also possible to carry out the process under elevated or reduced pressure.

To carry out process (a) according to the invention, the starting substances required in each case are generally employed in approximately equimolar amounts. However, it is also possible to use one of the two components employed in each case in a relatively large excess. In general, the reactions are carried out in a suitable diluent in the presence of a reaction auxiliary, and the reaction mixture is stirred for several hours at the temperature required in each case. Working-up in process (a) according to the invention is carried out in each case by customary methods (cf. the preparation examples).

Formulae (IA) and (IB)—with the proviso that $R^5$ in these formulae represents hydrogen—provide a general definition of the N-cyanoaryl-nitrogen heterocycles to be used as starting substances in process (b) according to the invention for the preparation of compounds of the formula (I).

In formulae (IA) and (IB), $R^1$, $R^2$, $R^3$ and $R^4$ preferably, or in particular, have those meanings which have already been mentioned above in connection with the description of the compounds of the formula (I) according to the invention as being preferred, or particularly preferred, for $R^1$, $R^2$, $R^3$ and $R^4$.

The starting substances of the formulae (IA) and (IB) for process (b) are new compounds according to the invention; they can be prepared by process (a) according to the invention.

Formulae (V) and (VI) provide general definitions of the alkylating agents furthermore to be used as starting substances in process (b) according to the invention.

In formulae (V) and (VI), $R^5$ preferably, or in particular, has the meaning which has already been mentioned above in connection with the description of the compounds of the formula (I) according to the invention as being preferred, or particularly preferred, for $R^5$.

The starting substances of the formulae (V) and (VI) are known chemicals for organic synthesis.

Process (b) according to the invention is preferably carried out using a diluent. Suitable diluents are mainly those which have already been mentioned in the description of the process (a) according to the invention.

Acid acceptors which can be employed in process (b) according to the invention are all acid-binding agents which can conventionally be used for such reactions. The following are preferably suitable: alkali metal hydrides and alkaline earth metal hydrides, such as lithium hydride, sodium hydride, potassium hydride and calcium hydride, alkali metal hydroxides and alkaline earth metal hydroxides, such as lithium hydroxide, sodium hydroxide, potassium hydroxide and calcium hydroxide, alkali metal carbonates, alkali metal hydrogen carbonates, alkaline earth metal carbonates and alkaline earth metal hydrogen carbonates, such as sodium carbonate, sodium hydrogen carbonate, potassium carbonate or potassium hydrogen carbonate, and calcium carbonate, alkali metal acetates, such as sodium acetate and potassium acetate, alkali metal alcoholates, such as sodium methylate, sodium ethylate, sodium propylate, sodium isopropylate, sodium butylate, sodium isobutylate, sodium tert-butylate, potassium methylate, potassium ethylate, potassium propylate, potassium isopropylate, potassium butylate, potassium isobutylate and potassium tert-butylate, furthermore basic nitrogen compounds, such as trimethylamine, triethylamine, tripropylamine, tributylamine, diisobutylamine, dicyclohexylamine, ethyldiisopropylamine, ethyldicyclohexylamine, N,N-dimethylbenzylamine, N,N-dimethyl-aniline, pyridine, 2-methyl-, 3-methyl-, 4-methyl-, 2,4-dimethyl-, 2,6-dimethyl-, 2-ethyl-, 4-ethyl- and 5-ethyl-2-methyl-pyridine, 1,5-diazabicyclo[4,3,0]-non-5-ene (DBN), 1,8-diazabicyclo-[5,4,0]-undec-7-en (DBU) and 1,4-diazabicyclo-[2,2,2]-octane (DABCO).

When carrying out process (b) according to the invention, the reaction temperatures can be varied within a substantial range. In general the process is carried out at temperatures between 0° C. and 120° C., preferably at temperatures between 10° C. and 100° C.

In general, process (b) according to the invention is carried out under atmospheric pressure. However, it is also possible to carry out the process under elevated or reduced pressure.

To carry out process (b) according to the invention, the starting substances required in each case are generally employed in approximately equimolar amounts. However, it is also possible to use one of the two components employed in each case in a relatively large excess. In general, the reactions are carried out in a suitable diluent in the presence of an acid acceptor, and the reaction mixture is stirred for several hours at the temperature required in each case. Working-up in process (b) according to the invention is carried out in each case by customary methods (cf. the preparation examples).

Formula (I)—with the proviso that $R^2$ in this formula represents halogen—provides a general definition of the N-cyanoaryl-nitrogen heterocycles to be used as starting substances in process (c) according to the invention for the preparation of compounds of the formula (I).

In formula (I), $R^1$, $R^3$, $R^4$ and Z then preferably, or particularly preferably, have those meanings which have already been mentioned above in connection with the description of the compounds of the formula (I) according to the invention as being preferred, or particularly preferred, for $R^1$, $R^3$, $R^4$ and Z.

The starting substances of the formula (I) for process (c) are new compounds according to the invention; they can be prepared by processes (a) and (b) according to the invention.

Formula (VII) provides a general definition of the amides furthermore to be used as starting substances in process (c) according to the invention.

In formula (VII), A preferably, or in particular, has the meaning which has already been mentioned above in connection with the description of the compounds of the formula (I) according to the invention as being preferred, or particularly preferred, for A.

The starting substances of the formula (VII) are known chemicals for organic synthesis.

Process (c) according to the invention is preferably carried out using a diluent. Suitable diluents are mainly those diluents which have already been mentioned in the description of process (a) according to the invention.

If appropriate, process (c) according to the invention is carried out in the presence of an acid acceptor. Suitable acid acceptors are those which have already been mentioned in the description of the process (b) according to the invention.

When carrying out process (c) according to the invention, the reaction temperatures can be varied within a substantial range. In general, the process is carried out at temperatures between 0° C. and 200° C., preferably at temperatures between 20° C. and 180° C.

In general, process (c) according to the invention is carried out under atmospheric pressure. However, it is also possible to carry out the process under elevated or reduced pressure.

To carry out process (c) according to the invention, the starting substances required in each case are generally employed in approximately equimolar amounts. However, it is also possible to use one of the two components employed in each case in a relatively large excess. In general, the reactions are carried out in a suitable diluent in the presence of an acid acceptor, and the reaction mixture is stirred for several hours at the temperature required in each case. Working-up in process (c) according to the invention is carried out in each case by customary methods (cf. preparation examples).

The active compounds according to the invention can be used as defoliants, desiccants, agents for destroying broad-leaved plants and, especially, as weed-killers. By weeds, in the broadest sense, there are to be understood all plants which grow in locations where they are undesired. Whether the substances according to the invention act as total or selective herbicides depends essentially on the amount used.

The active compounds according to the invention can be used, for example, in connection with the following plants:

Dicotyledon weeds of the genera: Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver, Centaurea, Trifolium, Ranunculus and Taraxacum.

Dicotyledon cultures of the genera: Gossypium, Glycine, Beta, Daucus, Phaseolus, Pisum, Solanum, Linum, Ipomoea, Vicia, Nicotiana, Lycopersicon, Arachis, Brassica, Lactuca, Cucumis and Cucurbita.

Monocotyledon weeds of the genera: Echinochloa, Setaria, Panicum, Digitaria, Phleum, Poa, Festuca, Eleusine, Brachiaria, Lolium, Bromus, Arena, Cyperus, Sorghum, Agropyron, Cynodon, Monochoria, Fimbristylis, Sagittaria, Eleocharis, Scirpus, Paspalum, Ischaemum, Sphenoclea, Dactyloctenium, Agrostis, Alopecurus and Apera.

Monocotyledon cultures of the genera: Oryza, Zea, Triticum, Hordeum, Arena, Secale, Sorghum, Panicum, Saccharum, Ananas, Asparagus and Allium.

However, the use of the active compounds according to the invention is in no way restricted to these genera, but also extends in the same manner to other plants. The compounds are suitable, depending on the concentration, for the total combating of weeds, for example on industrial terrain and rail tracks, and on paths and squares with or without tree plantings. Equally, the compounds can be employed for combating weeds in perennial cultures, for example afforestations, decorative tree plantings, orchards, vineyards, citrus groves, nut orchards, banana plantations, coffee plantations, tea plantations, rubber plantations, oil palm plantations, cocoa plantations, soft fruit plantings and hopfields, in lawns, turf and pasture-land, and for the selective combating of weeds in annual cultures.

The compounds of the formula (I) according to the invention—inclusively those disclaimed by disclaimer—are particularly suitable for selectively combating dicotyledonous weeds in monocotyledon and dicotyledon cultures, such as, for example, in wheat, maize and soya beans, both in the pre-emergence method and in the post-emergence method, although the individual compounds including those disclaimed by disclaimer, have selective activity in cultures, such as, for example, in wheat, corn and soya beans.

The active compounds can be converted into the customary formulations, such as solutions, emulsions, wettable powders, suspensions, powders, dusting agents, pastes, soluble powders, granules, suspension-emulsion concentrates, natural and synthetic materials impregnated with active compound, and very fine capsules in polymeric substances.

These formulations are produced in a known manner, for example by mixing the active compounds with extenders, that is liquid solvents and/or solid carriers, optionally with the use of surface-active agents, that is emulsifying agents and/or dispersing agents and/or foam-forming agents.

In the case of the use of water as an extender, organic solvents can, for example, also be used as auxiliary solvents. As liquid solvents, there are suitable in the main: aromatics, such as xylene, toluene or alkylnaphthalenes, chlorinated aromatics and chlorinated aliphatic hydrocarbons, such as chlorobenzenes, chloroethylenes or methylene chloride, aliphatic hydrocarbons, such as cyclohexane or paraffins, for example petroleum fractions, mineral and vegetable oils, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulphoxide, as well as water.

As solid carriers there are suitable: for example ammonium salts and ground natural minerals, such as kaolins, clays, talc, chalk, quartz, attapulgite, montmorillonite or diatomaceous earth, and ground synthetic minerals, such as highly disperse silica, alumina and silicates, as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, maize cobs and tobacco stalks; as emulsifying and/or foam-forming agents there are suitable: for example non-ionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates as well as albumen hydrolysis products; as dispersing agents there are suitable: for example ligninsulphite waste liquors and methylcellulose.

Adhesives such as carboxymethylcellulose and natural and synthetic polymers in the form of powders, granules or latexes, such as gum arabic, polyvinyl alcohol and polyvinyl acetate, as well as natural phospholipids, such as cephalins and lecithins, and synthetic phospholipids, can be used in the formulations. Further additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dye-stuffs, and trace nutrients such as salts of iron, manganese, boron, copper, cobalt, molybdenum and zinc.

The formulations in general contain between 0.1 and 95 per cent by weight of active compound, preferably between 0.5 and 90%.

For combating weeds, the active compounds according to the invention, as such or in their formulations, can also be used in mixtures with known herbicides, finished formulations or tank mixtures being possible.

Suitable herbicides for the mixtures are known herbicides, for example anilides such as, for example, diflufenican and propanil; arylcarboxylic acids such as, for example, dichloropicolinic acid, dicamba and picloram; aryloxyalkanoic acids such as, for example, 2,4-D, 2,4-DB, 2,4-DP, fluroxypyr, MCPA, MCPP and triclopyr; aryloxy-phenoxyalkanoic esters such as, for example, diclofopmethyl, fenoxapropethyl, fluazifop-butyl, haloxyfop-methyl and quizalofop-ethyl; azinones such as, for example, chloridazon and norflurazon; carbamates such as, for example, chlorpropham, desmedipham, phenmedipham and propham; chloroacetanilides such as, for example, alachlor, acetochlor, butachlor, metazachlor, metolachlor, pretilachlor and propachlor; dinitroanilines such as, for example, oryzalin, pendimethalin and trifluralin; diphenyl ethers such as, for example, acifluorfen, bifenox, fluoroglycofen, fomesafen, halosafen, lactofen and oxyfluorfen; ureas such as, for example, chlortoluron, diuron, fluometuron, isoproturon, linuron and methabenzthiazuron; hydroxylamines such as, for example, alloxydim, clethodim, cycloxydim, sethoxydim and tralkoxydim; imidazolinones such as, for example, imazethapyr, imazamethabenz, imazapyr and imazaquin; nitriles such as, for example, bromoxynil, dichlobenil and ioxynil; oxyacetamides such as, for example, mefenacet; sulphonylureas such as, for example, amidosulfuron, bensulfuron-methyl, chlorimuron-ethyl, chlorsulfuron, cinosulfuron, metsulfuron-methyl, nicosulfuron, primisulfuron, pyrazosulfuron-ethyl, thifensulfuron-methyl, triasulfuron and tribehuronmethyl; thiocarbamates such as, for example, butylate, cycloate, di-allate, EPTC, esprocarb, molinate, prosulfocarb, thiobencarb and tri-allate; triazines such as, for example, atrazine, cyanazine, simazine, simetryn, terbutryn and terbutylazine; triazinones such as, for example, hexazinone, metamitron and metribuzin; others such as, for example, aminotriazole, benfuresate, bentazone, cinmethylin, clomazone, clopyralid, difenzoquat, dithiopyr, ethofumesate, fluorochloridone, glufosinate, glyphosate, isoxaben, pyridate, quinchlorac, quinmerac, sulphosate and tridiphane.

Mixtures with other known active compounds, such as fungicides, insecticides, acaricides, nematicides, bird repellents, plant nutrients and agents which improve soil structure, are also possible.

The active compounds can be used as such, in the form of their formulations or in the use forms prepared therefrom by further dilution, such as ready-to-use solutions, suspensions, emulsions, powders, pastes and granules. They are used in the customary manner, for example by watering, spraying, atomizing or scattering.

The active compounds according to the invention can be applied either before or after emergence of the plants. They can also be incorporated into the soil before sowing.

The amount of active compound used can vary within a substantial range. It depends essentially on the nature of the desired effect. In general, the amounts used are between 10 g and 10 kg of active compound per hectare of soil surface, preferably between 50 g and 5 kg per ha.

The preparation and use of the active compounds according to the invention can be seen from the following examples.

PREPARATION EXAMPLES

Example 1

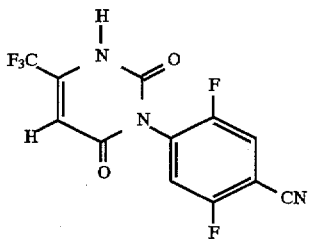

Process (a))

1.8 g (10mMol) of ethyl 3-amino-4,4,4-trifluorocrotonate are introduced into 30 ml of dimethylformamide and 2 ml of toluene, and 0.3 g (10 mMol) of sodium hydride (80%) is added at 0° C. to 5° C. The mixture is stirred for 30 minutes at 0° C. to 5° C. After the mixture has been cooled to –70° C., 0.9 g (5 mMol) of 4-cyano-2,5-difluoro-phenyl isocyanate—dissolved in 10 ml of toluene—are added and the mixture is stirred for 150 minutes at –60° C. to –70° C. After the cooling bath has been removed, 2 ml of acetic acid are added. The mixture is then diluted with water to approximately twice its volume and extracted using ethyl acetate. The organic phase is concentrated, and the residue is crystallized using diisopropyl ether.

1.1 g (69% of theory) of 1-(4-cyano-2,5-difluoro-phenyl)-3,6-dihydro-2,6-dioxo-4-trifluoromethyl-1(2H)-pyrimidine of melting point 194° C. are obtained.

Example 2

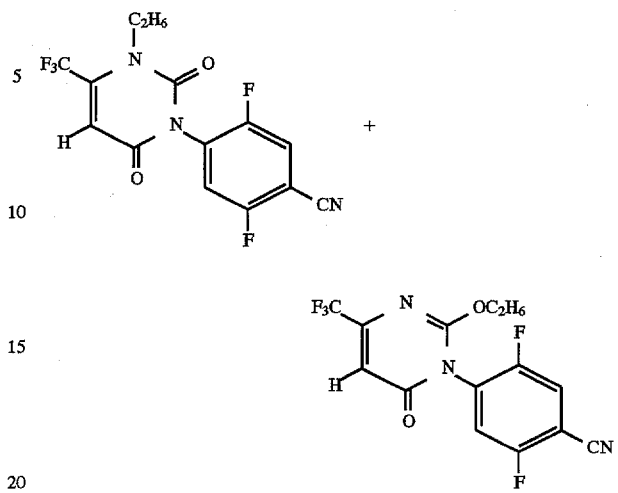

(process (b))

A mixture of 3.2 g (10 mMol) of 1-(4-cyano-2,5-difluoro-phenyl)-3,6-dihydro-2,6-dioxo-4-trifluoromethyl-1(2H)-pyrimidine, 3.1 g (20 mMol) of diethyl sulphate, 2.8 g of potassium carbonate and 100 ml of acetonitrile is refluxed for 3 hours. It is then concentrated in vacuo and extracted by shaking with water/chloroform, and the organic phase, again, is concentrated in vacuo, and the residue is separated by column chromatography (silica gel, petroleum ether/ethyl acetate 1:1).

The first fraction obtained is 0.30 g of 1-(4-cyano-2,5-difluoro-phenyl)-1,6-dihydro-2-ethoxy-6-oxo-4-trifluoromethyl-pyrimidine (amorphous) and the second fraction is 0.38 g of 1-(4-cyano-2,5-difluoro-phenyl)-3,6-dihydro-2,6-dioxo-3-ethyl-4-trifluoromethyl-1(2H)-pyrimidine (amorphous, $^1$-NMR: d=6.36 ppm). Total yield: 0.68 g (20% of theory).

Example 3

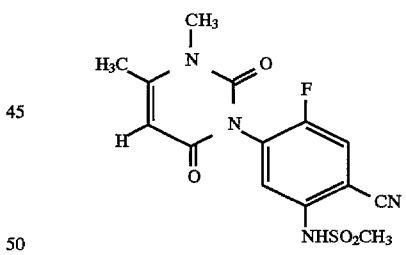

(Process (c))

A mixture of 0.83 g (3 mMol) 1-(4-cyano-2,5-difluoro-phenyl)-3,6-dihydro-2,6-dioxo-3,4-dimethyl-1(2H)-pyrimidine, 0.32 g (3 mMol) of methanesulfonamide, 0.6 g of potassium carbonate and 10 ml of dimethyl sulphoxide is heated for 10 hours at 120° C.. After the mixture has been cooled, it is poured into ice-water and acidified using 2N-hydrochloric acid. It is then extracted using ethyl acetate, and the organic phase is washed with water, dried using sodium sulphate and filtered. The solvent is carefully removed from the filtrate by distillation under a water pump vacuum.

0.8 g (76% of theory) of 1-(4-cyano-2-fluoro-5-methylsulphonylaminophenyl)-3,6-dihydro-2,6-dioxo-3,4-dimethyl-1(2H)-pyrimidine is obtained as a crystalline residue (melting point >250° C).

Examples of the compounds of the formula (I) or of formulae (IA) and (IB) which can be prepared analogously to Examples 1 to 3 and following the general description of the preparation processes according to the invention are those listed in Table 2 below.

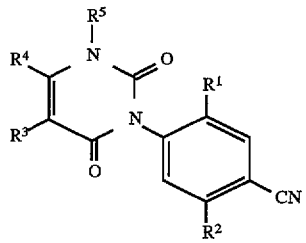

(IA)

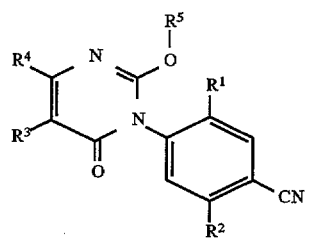

(IB)

TABLE 2

Examples of the compounds of the formula (I)

| Ex. no. | Gen. formula | R¹ | R² | R³ | R⁴ | R⁵ | melting point (°C.) |
|---|---|---|---|---|---|---|---|
| 4 | IA | F | F | H | $CH_3$ | H | 273 |
| 5 | IA | F | F | H | $CH_3$ | $CH_3$ | 264 |
| 6 | IA | F | F | H | $CH_3$ | $CHF_2$ | |
| 7 | IA | F | F | H | $CH_3$ | $NH_2$ | |
| 8 | IA | F | $NHSO_2C_2H_5$ | H | $CH_3$ | $CH_3$ | ¹H-NMR: d = 5.76 ppm |
| 9 | IA | F | $NHSO_2CH_3$ | H | $CH_3$ | $CHF_2$ | |
| 10 | IA | F | $NHSO_2CH_3$ | H | $CH_3$ | $NH_2$ | |
| 11 | IA | H | $NHSO_2CH_3$ | H | $CH_3$ | $NH_2$ | |
| 12 | IA | F | F | H | $CF_3$ | $CH_3$ | 155 |
| 13 | IA | F | F | H | $CF_3$ | $C_3H_7$ | |
| 14 | IA | Cl | F | $CH_3$ | $CF_3$ | $CHF_2$ | |
| 15 | IA | F | $NHSO_2CH_3$ | H | $CF_3$ | $CH_3$ | |
| 16 | IA | F | $NHSO_2C_2H_5$ | H | $CF_3$ | $C_2H_5$ | |
| 17 | IA | F | $NHSO_2$—⊲ | H | $CF_3$ | $CHF_2$ | |
| 18 | IA | F | $NHSO_2CH_3$ | H | $CF_3$ | $NH_2$ | |
| 19 | IA | F | $NHSO_2C_2H_5$ | H | $CH_2Cl$ | $CH_3$ | |
| 20 | IA | F | F | H | $CF_2CF_3$ | H | 172 |
| 21 | IA | F | F | H | $CF_2CF_3$ | $CH_3$ | 97 |
| 22 | IA | H | F | H | $CF_2CF_3$ | $C_2H_5$ | |
| 23 | IA | H | F | H | $CF_2CF_3$ | $CH_2CH=CH_2$ | |
| 24 | IA | F | $NHSO_2CH_3$ | H | $CF_2CF_3$ | $CH_3$ | |
| 25 | IA | F | $NHSO_2C_2H_5$ | H | $CF_2CF_3$ | $CH_3$ | |
| 26 | IA | F | F | H | $CHF_2$ | H | |
| 27 | IA | F | F | H | $CHF_2$ | $CH_3$ | |
| 28 | IA | F | F | H | $CHF_2$ | $CHF_2$ | |
| 29 | IA | F | F | H | $CHF_2$ | $NH_2$ | |
| 30 | IA | F | $NHSO_2CH_3$ | H | $CHF_2$ | $CH_3$ | 188 |
| 31 | IA | F | $NHSO_2CH_3$ | H | $CHF_2$ | $CHF_2$ | |
| 32 | IA | F | $NHSO_2CH_3$ | H | $CHF_2$ | $NH_2$ | |
| 33 | IA | F | $NHSO_2C_2H_5$ | Cl | $CHF_2$ | $CH_2CH=CH_2$ | |
| 34 | IB | F | F | H | $CF_3$ | $CH_3$ | ¹H-NMR: d = 6.92 ppm |
| 35 | IB | F | F | H | $CF_2CF_3$ | $CH_3$ | 116 |
| 36 | IB | F | $NHSO_2CH_3$ | H | $CF_3$ | $CH_3$ | 192 |
| 37 | IB | F | $NHSO_2C_2H_5$ | H | $CF_3$ | $CH_3$ | |
| 38 | IB | F | $NHSO_2CH_3$ | H | $CF_3$ | $C_2H_5$ | |
| 39 | IB | F | $NHSO_2C_2H_5$ | H | $CF_2CF_3$ | $CH_3$ | |
| 40 | IB | F | $NHSO_2C_3H_7$ | H | $CF_3$ | $CH_3$ | |
| 41 | IA | F | $NHSO_2CF_3$ | H | $CH_3$ | $CH_3$ | |
| 42 | IA | F | $NHSO_2CH_3$ | H | $CF_3$ | H | 248 |
| 43 | IA | F | $NSO_2CH_3$ \| $CH_3$ | H | $CF_3$ | $CH_3$ | 115 |
| 44 | IA | F | $NHSO_2C_2H_5$ | H | $CF_3$ | H | 228 |

TABLE 2-continued

Examples of the compounds of the formula (I)

| Ex. no. | Gen. formula | $R^1$ | $R^2$ | $R^3$ | $R^4$ | $R^5$ | melting point (°C.) |
|---|---|---|---|---|---|---|---|
| 45 | IA | F | NSO$_2$C$_2$H$_5$<br>\|<br>CH$_3$ | H | CF$_3$ | H | 49 |
| 46 | IA | F | NSO$_2$C$_2$H$_5$<br>\|<br>C$_2$H$_5$ | H | CF$_3$ | CH$_3$ | 162 |
| 47 | IA | F | NHSO$_2$C$_3$H$_7$ | H | CF$_3$ | H | 154 |
| 48 | IA | F | NSO$_2$C$_2$H$_5$<br>\|<br>C$_2$H$_5$ | H | CF$_3$ | C$_2$H$_5$ | 177 |
| 49 | IA | F | NSO$_2$C$_2$H$_5$<br>\|<br>C$_2$H$_5$ | H | CF$_3$ | H | $^1$H-NMR: 6.5 ppm |
| 50 | IA | F | NSO$_2$C$_3$H$_7$<br>\|<br>CH$_3$ | H | CF$_3$ | CH$_3$ | $^1$H-NMR: 6.4 ppm |
| 51 | IA | F | NHSO$_2$C$_2$H$_5$ | H | CHF$_2$ | H | 258 |
| 52 | IA | F | NSO$_2$C$_2$H$_5$<br>\|<br>CH$_3$ | H | CHF$_2$ | CH$_3$ | 173 |
| 53 | IA | F | NHSO$_2$C$_6$H$_5$ | H | CF$_3$ | H | 253 |
| 54 | IA | F | NSO$_2$C$_6$H$_5$<br>\|<br>CH$_3$ | H | CF$_3$ | CH$_3$ | 136 |
| 55 | IA | F | NHSO$_2$CH$_3$ | H | CF$_3$ | CHF$_2$ | 230 |
| 56 | IA | F | NHSO$_2$CH(CH$_3$)$_2$ | H | CF$_3$ | H | 217 |
| 57 | IA | F | NSO$_2$CH(CH$_3$)$_2$<br>\|<br>CH$_3$ | H | CF$_3$ | CH$_3$ | 163 |
| 58 | IA | F | NHSO$_2$CH$_3$ | CH$_3$ | CF$_3$ | H | 229 |
| 59 | IA | F | NSO$_2$CH$_3$<br>\|<br>CH$_3$ | CH$_3$ | CF$_3$ | CH$_3$ | 115 |
| 60 | IA | F | NHSO$_2$CH$_3$ | H | CHF$_2$ | H | 281 |
| 61 | IA | F | NSO$_2$CH$_3$<br>\|<br>CH$_3$ | H | CHF$_2$ | CH$_3$ | 264 |
| 62 | IA | F | NHSO$_2$— | H | CF$_3$ | H | 262 |
| 63 | IA | F | NHSO$_2$CH$_3$ | H | CF$_2$Cl | H | 269 |
| 64 | IA | F | NSO$_2$—<br>\|<br>CH$_3$ | H | CF$_3$ | CH$_3$ | 150 |
| 65 | IA | F | NSO$_2$CH$_3$<br>\|<br>CH$_3$ | H | CF$_2$Cl | CH$_3$ | 97 |
| 66 | IA | F | NHSO$_2$CH$_3$ | H | CF$_2$Cl | CH$_3$ | 206 |
| 67 | IA | F | NHSO$_2$— | H | CF$_3$ | CH$_3$ | 180 |

Starting substances of the formula (III)

Example (III-1)

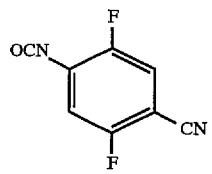

660 g of phosgene are condensed into 1.6 liters of chlorobenzene at −5° C. to 0° C. At the same temperature, a solution of 400 g of 4-cyano-2,5-difluoro-aniline in 800 ml of chlorobenzene is added dropwise in the course of 60 minutes. The reaction mixture is subsequently heated up slowly (HCl evolution!) to 120° C., and, after a temperature of 80° C. has been reached, phosgene is passed in continuously. After heating for 1 hour at 120° C., excess phosgene is purged using nitrogen and the reaction mixture is worked up by means of distillation.

248 g (53% of theory) of 4-cyano-2,5-difluoro-phenyl isocyanate of boiling point 108°–110° C./14 mbar (melting point: 53° C.) are obtained.

Starting materials of the formula (IV)

Example (IV-1)

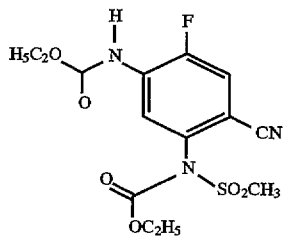

13.0 g (0.05 mol) of ethyl chloroformate are added dropwise to a mixture of 11.5 g (0.05 mol) of 4-cyano-2-fluoro-5-methylsulphonylaminoaniline, 18 g of pyridine and 400 ml of methylene chloride at 20° C. while stirring, and the reaction mixture is stirred for a further 30 minutes at 20° C. to 30° C. Thereafter the mixture is washed with water, then with 5% strength hydrochloric acid and again with water, dried with sodium sulphate and filtered, and the filtrate is evaporated down. The remaining residue is digested with a little ethyl acetate, and the product obtained in crystalline form is isolated by filtration with suction.

15.8 g (85% of theory) of N-ethoxycarbonyl-N-(2-cyano-4-fluoro-5-ethoxycarbonylamino-phenyl)-methanesulphonamide of melting point 129° C. are obtained.

For example, the compounds of the formula (IV) shown in Table 3 below may also be prepared analogously to Example (IV-1)

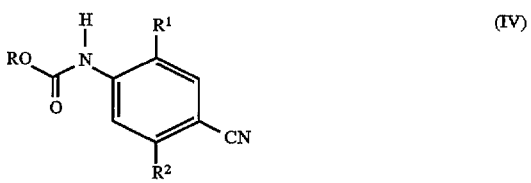

TABLE 3

| Ex. no. | R | $R^1$ | $R^2$ | melting point (°C.) |
|---|---|---|---|---|
| IV-2 | $CH_3$ | H | $NSO_2C_2H_5$<br>\|<br>$COOCH_3$ | |
| IV-3 | $C_2H_5$ | F | $NSO_2C_2H_5$<br>\|<br>$CO-CH_3$ | 129 |
| IV-4 | $C_2H_5$ | F | $NSO_2C_2H_5$<br>\|<br>$COOC_2H_5$ | 140 |
| IV-5 | $CH_3$ | F | $NSO_2C_2H_5$<br>\|<br>$COOCH_3$ | |
| IV-6 | $CH_3$ | F | $N-SO_2CH_3$<br>\|<br>$COOCH_3$ | |
| IV-7 | $CH_3$ | F | $N-SO_2C_3H_7$<br>\|<br>$COOCH_3$ | |
| IV-8 | $CH_3$ | F | $N-SO_2CH(CH_3)_2$<br>\|<br>$COOCH_3$ | |
| IV-9 | $CH_3$ | F | $N-SO_2-\triangleleft$<br>\|<br>$COOCH_3$ | |
| IV-10 | $CH_3$ | F | $N-SO_2C_4H_9$<br>\|<br>$COOCH_3$ | |
| IV-11 | $CH_3$ | F | $N-SO_2C_6H_5$<br>\|<br>$COOCH_3$ | |
| IV-12 | $C_2H_5$ | F | $N-SO_2C_5H_6$<br>\|<br>$COOC_2H_5$ | 178 |
| IV-13 | $C_2H_5$ | F | $N-SO_2C_4H_9$<br>\|<br>$COOC_2H_5$ | 92 |
| IV-14 | $C_2H_5$ | F | $N-SO_2C_3H_7$<br>\|<br>$COOC_2H_5$ | 109 |
| IV-15 | $C_2H_5$ | F | $N-SO_2CH(CH_3)_2$<br>\|<br>$COOC_2H_6$ | 158 |
| IV-16 | $C_2H_5$ | F | $N-SO_2-\triangleleft$<br>\|<br>$COOC_2H_5$ | 142 |

Use Examples

Example A

Pre-emergence test

Solvent: 5 parts by weight of acetone

Emulsifier: 1 part by weight of alkylaryl polyglycol ether

To produce a suitable preparation of active compound, 1 part by weight of active compound is mixed with the stated amount of solvent, the stated amount of emulsifier is added and the concentrate is diluted with water to the desired concentration.

Seeds of the test plants are sown in normal soil and, after 24 hours, watered with the preparation of the active compound. It is expedient to keep constant the amount of water per unit area. The concentration of the active compound in the preparation is of no importance, only the amount of active compound applied per unit area being decisive. After three weeks, the degree of damage to the plants is rated in % damage in comparison to the development of the untreated control. The figures denote:

0%=no action (like untreated control)
100%=total destruction

In this test, the compounds of preparation examples 2 (2nd fraction) and 12, for example, show a very potent activity against weeds, while being well-tolerated by crop plants, such as, for example, maize.

Example B

Post-emergence test

Solvent: 5 parts by weight of acetone

Emulsifier: 1 part by weight of alkylaryl polyglycol ether

To produce a suitable preparation of active compound, 1 part by weight of active compound is mixed with the stated amount of solvent, the stated amount of emulsifier is added and the concentrate is diluted with water to the desired concentration. Test plants which have a height of 5–15 cm are sprayed with the preparation of the active compound in such a way as to apply the particular amounts of active compound desired per unit area. After three weeks, the degree of damage to the plants is rated in % damage in comparison to the development of the untreated control. The figures denote:

0%=no action (like untreated control)
100%=total destruction

In this test, the compounds of preparation examples 2 (2nd fraction) and 12, for example, show potent activity against weeds, while being well tolerated by crop plants, such as, for example, wheat.

It will be understood that the specification and examples are illustrative but not limitative of the present invention and that other embodiments within the spirit and scope of the invention will suggest themselves to those skilled in the art.

What is claimed is:

1. A N-cyanoaryl-nitrogen heterocycle of the formula

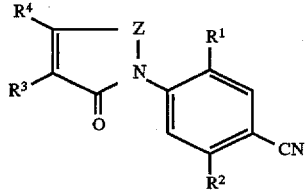

$R^1$ is hydrogen, fluorine, chlorine or bromine, $R^2$ is the group —N($A^1$)SO$_2$A in which A is a radical selected from the group consisting of alkyl, alkenyl and alkinyl, each of which has up to 10 carbon atoms and each of which is optionally substituted by fluorine, chlorine, bromine, cyano or $C_1$–$C_4$-alkoxy, or A is cycloalkyl or cycloalkylalkyl, each of which has 3 to 8 carbon atoms in the cycloalkyl moiety and, if appropriate, 1 to 4 carbon atoms in the alkyl moiety and each of which is optionally substituted by fluorine, chlorine, bromine, cyano or $C_1$–$C_4$-alkyl, or A is aryl or arylalkyl, each of which has 6 or 10 carbon atoms in the aryl moiety and 1 to 4 carbon atoms in the alkyl moiety and each of which is optionally substituted by fluorine, chlorine, bromine, cyano, nitro, carboxyl, carbamoyl, by $C_1$–$C_4$-alkyl, $C_1$–$C_4$-alkoxy, $C_1$–$C_4$-alkylthio, $C_1$–$C_4$-alkylsulphinyl or $C_1$–$C_4$-alkylsulphonyl (each of which is optionally substituted by at least one of fluorine and chlorine), by dimethylaminosulphonyl or diethylaminosulphonyl, by $C_1$–$C_4$-alkoxycarbonyl (which is optionally substituted by fluorine, chlorine, bromine, methoxy or ethoxy), by phenyl, phenyloxy or phenylthio (each of which is optionally substituted by at least one of fluorine, chlorine, bromine, cyano, methyl, methoxy, trifluoromethyl and trifluoromethoxy), or A is thienyl, pyrazolyl, or pyridyl, or thienyl-, pyrazolyl- or pyridyl-alkyl having 1 to 4 carbon atoms in the alkyl moiety and each of which is optionally substituted by fluorine, bromine, cyano, nitro, carboxyl, carbamoyl, by $C_1$–$C_4$-alkyl, $C_1$–$C_4$-alkoxy, $C_1$–$C_4$-alkylthio, $C_1$–$C_4$-alkylsulphinyl or $C_1$–$C_4$-alkylsulphonyl or $C_1$–$C_4$-alkoxycarbonyl (each of which is optionally substituted by at least one of fluorine and chlorine), by phenyl, phenoxy or phenylthio (each of which is optionally substituted by at least one of fluorine, chlorine, bromine, cyano, methyl, methoxy, trifluoromethyl and trifluoromethoxy), and $A^1$ is hydrogen or alkyl, alkenyl, alkinyl, alkoxy, alkylcarbonyl or alkoxylcarbonyl, each of which has up to 6 carbon atoms and each of which is optionally substituted by halogen or $C_1$–$C_4$-alkoxy, or is phenylcarbonyl, naphthylcarbonyl, phenylmethylcarbonyl, substituted by halogen or $C_1$–$C_4$-alkoxy, or is phenylcarbonyl, naphthylcarbonyl, phenylmethylcarbonyl, naphthylmethylcarbonyl, phenoxycarbonyl or naphthyloxycarbonyl (each of which is optionally substituted by at least on of fluorine, chlorine, bromine, cyano, methyl, methoxy, trifluoromethyl and trifluoromethoxy), $R^3$ is hydrogen, fluorine, chlorine, bromine, cyano or alkyl having 1 to 6 carbon atoms which is optionally substituted by at least one of fluorine and chlorine, $R^4$ is alkyl having 1 to 6 carbon atoms which is optionally substituted by fluorine, chlorine, bromine, methoxy or ethoxy, or together with $R^3$ is alkanediyl having 2 to 8 carbon atoms, and Z is

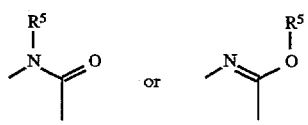

in which $R^5$ is substituted amino, or is alkyl, alkenyl, alkinyl, alkoxycarbonyl, each of which has up to 6 carbon atoms and each of which is optionally substituted by fluorine, bromine, cyano, $C_1$–$C_4$-alkoxy, $C_1$–$C_4$-alkylcarbonyl or $C_1$–$C_4$-alkoxycarbonyl, or a salt thereof, with the exception of the compounds
1-(4-cyano-3-ethyl-sulphonylamino-phenyl)-3,6-dihydro-2,6-dioxo-3-methyl-4-trifluoromethyl-1(2H)-pyrimidine,
1-(4-cyano-3-n-propylsulphonylamino-phenyl)-3,6-dihydro-2,6-dioxo-3-methyl-4-trifluoromethyl-1(2H)-pyrimidine,
1-(4-cyano-3-isopropylsulphonylamino-phenyl)-3,6-dihydro-2,6-dioxo-3-methyl-4-trifluoromethyl-1(2H)-pyrimidine,
1-(4-cyano-5-ethyl-sulphonylamino-2-fluoro-phenyl)-3,6-dihydro-2,6-dioxo-3-methyl-4-trifluoromethyl-1(2H)-pyrimidine,
1-(4-cyano-5-n-propylsulphonylamino-2-fluoro-phenyl)-3,6-dihydro-2,6-dioxo-3-methyl-4-trifluoromethyl-1(2H)-pyrimidine,
1-(4-cyano-5-isopropylsulphonylamino-2-fluoro-phenyl)-3,6-dihydro-2,6-dioxo-3-methyl-4-trifluoromethyl-1(2H)-pyrimidine,
or a salt thereof.

2. A N-cyanoaryl-nitrogen heterocycle according to claim 1, wherein $R^1$ is hydrogen, fluorine or chlorine, $R^2$ is the group $N(A^1)SO_2A$ in which
A is methyl, ethyl, n- or i-propyl, n-, i-, s-, or t-butyl or n-, i-, s- or t-pentyl, each of which is optionally substituted by fluorine or chlorine, or
A is cyclopropyl, cyclobutyl, cyclopentyl, cyclohexyl, cyclopentylmethyl or cylcohexymethyl, each of which is optionally substituted by at least one of fluorine, chlorine, bromine, methyl and ethyl, or
A is phenyl, naphthyl, phenylmethyl or phenylethyl, each of which is optionally substituted by fluorine, chlorine, bromine, cyano, nitro, carboxy, difluoromethoxy, trifluoromethoxy, methylthio, ethylthio, methylsulphinyl, ethylsulphinyl, methylsulphonyl, ethylsulphonyl, dimethylaminosulphonyl, methoxycarbonyl, ethoxycarbonyl, propoxycarbonyl or phenyl, or
A is thienyl, pyrazolyl or pyridyl, each of which is optionally substituted by fluorine, chlorine, bromine, cyano, methyl, ethyl, trifluoromethyl, methoxy, ethoxy, methylthio, ethylthio, methylsulphinyl, ethylsulphinyl, methylsulphonyl, ethylsulphonyl, methoxycarbonyl or ethoxycarbonyl, and
$A^1$ is hydrogen, methyl, ethyl, n- or i-propyl, n- i- or s-butyl, propenyl, butenyl, propinyl, butinyl, methoxy, ethoxy, n- or i-propoxy, n-, i-, s- or t-butoxy, acetyl, propionyl, methoxycarbonyl or ethoxycarbonyl, each of which is optionally substituted by fluorine, chlorine, methoxy or ethoxy, or is phenylcarbonyl or phenoxycarbonyl, $R^3$ is hydrogen, fluorine, chlorine, bromine, methyl, trifluoromethyl, ethyl or n- or i-propyl, $R^4$ is methyl, ethyl, n- or i-propyl, each of which is optionally substituted by fluorine or chlorine, or together with $R^3$ is trimethylene or tetramethylene, and Z is

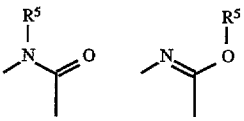

in which
$R^5$ is hydrogen, amino or methyl, ethyl, n- or i-propyl, n-, i- or s-butyl, propenyl, butenyl, propinyl, butinyl, acetyl, propionyl, methoxycarbonyl or ethoxycarbonyl, each of which is optionally substituted by fluorine, chlorine or cyano,
or
a salt thereof with a base selected from the group consisting of sodium, potassium and calcium hydroxide, hydride, amide or carbonate, a sodium or potassium $C_1$-$C_4$-alkanolate, ammonia, a $C_1$-$C_4$-alkylamine, di-($C_1$-$C_4$-alkyl)-amine, tri-($C_1$-$C_4$-alkyl)-amine and tris-(2-hydroxyethyl)amine,
or a salt thereof.

3. A compound according to claim 1, selected from the group consisting of

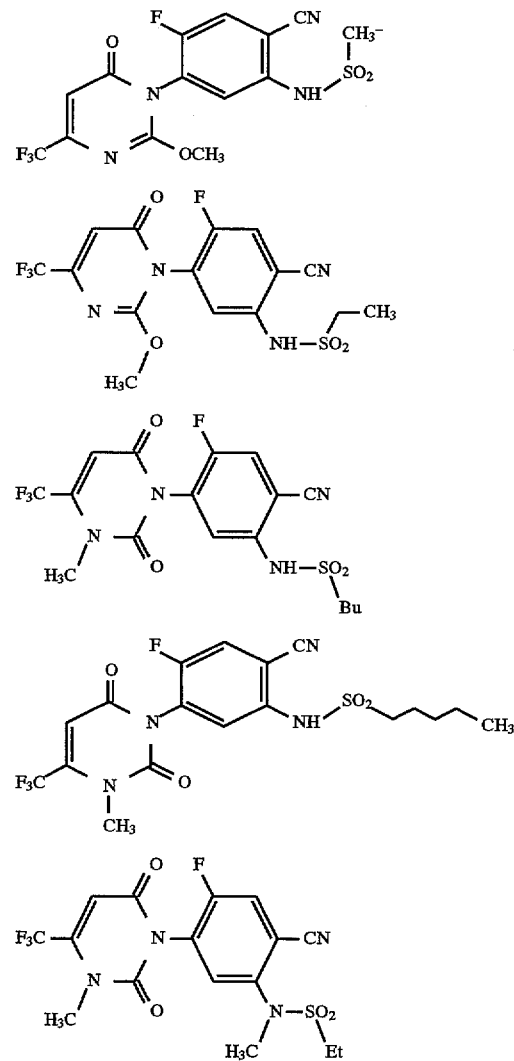

-continued
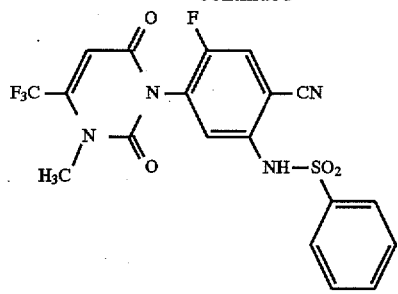
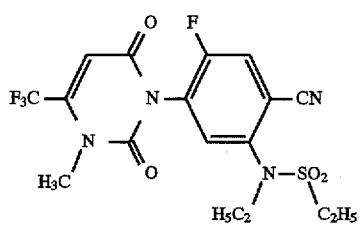
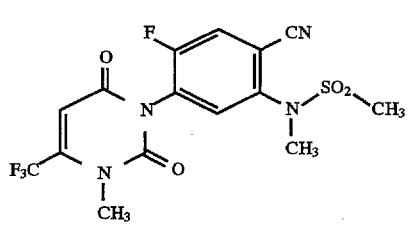
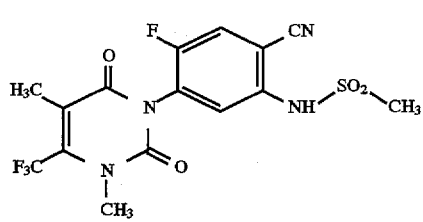
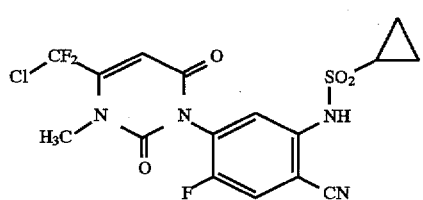
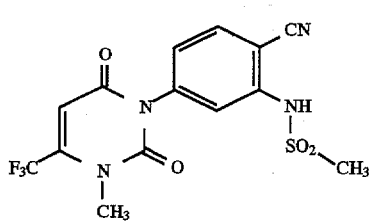
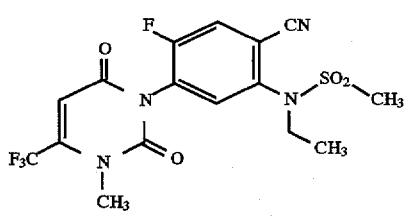
-continued
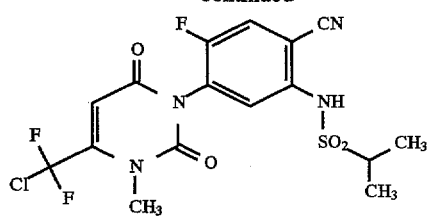
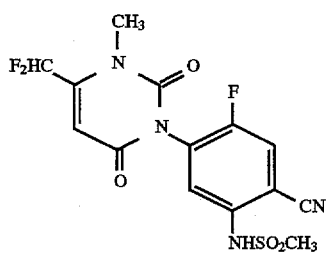
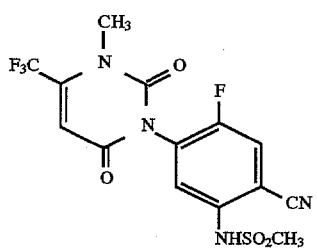
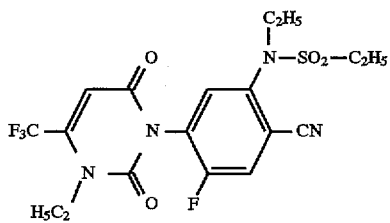
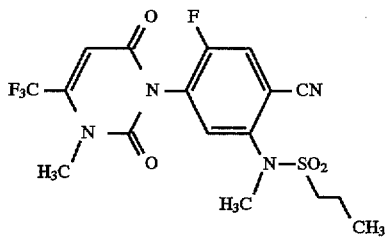
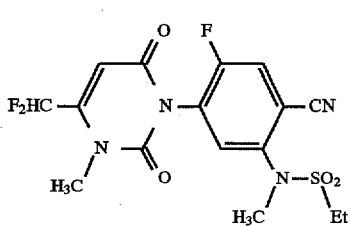

-continued

4. A compound according to claim 1, wherein such compound is or a salt thereof.

5. A compound according to claim 1, wherein such compound is or a salt thereof.

6. A compound according to claim 1, wherein such compound is or a salt thereof.

7. A compound according to claim 1, wherein such compound is or a salt thereof.

8. A compound according to claim 1, wherein such compound is or a salt thereof.

9. A compound according to claim 1, wherein such compound is or a salt thereof.

10. A compound according to claim 1, wherein such compound is or a salt thereof.

11. A compound according to claim 1, wherein such compound is or a salt thereof.

12. A compound according to claim 1, wherein such compound is or a salt thereof.

13. A compound according to claim 1, wherein such compound is or a salt thereof.

14. A compound according to claim 1, wherein such compound is or a salt thereof.

15. A compound according to claim 1, wherein such compound is or a salt thereof.

16. A compound according to claim 1, wherein such compound is or a salt thereof.

17. A compound according to claim 1, wherein such compound is or a salt thereof.

18. A compound according to claim 1, wherein such compound is

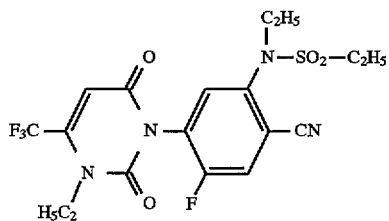

or a salt thereof.

19. A compound according to claim 1, wherein such compound is

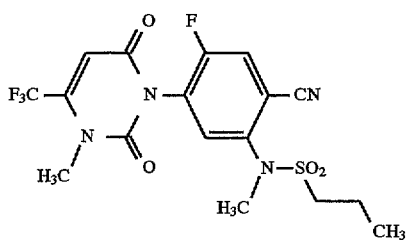

or a salt thereof.

20. A compound according to claim 1, wherein such compound is

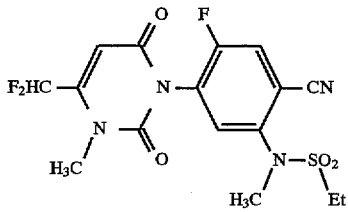

or a salt thereof.

21. A compound according to claim 1, wherein such compound is

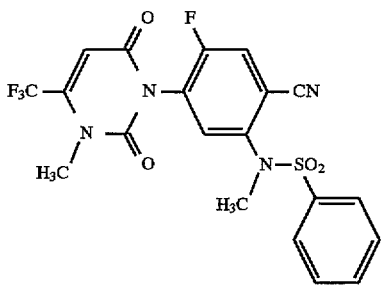

or a salt thereof.

22. A compound according to claim 1, wherein such compound is

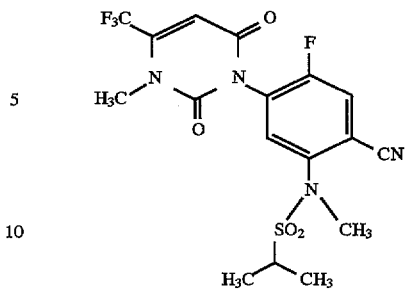

or a salt thereof.

23. A compound according to claim 1, wherein such compound is

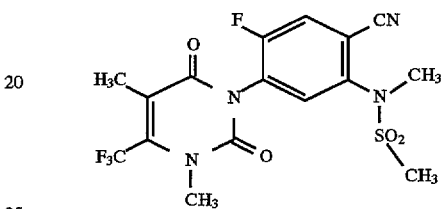

or a salt thereof.

24. A compound according to claim 1, wherein such compound is

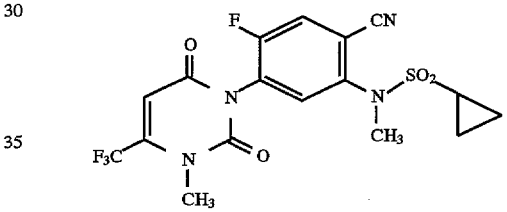

or a salt thereof.

25. A compound according to claim 1, wherein such compound is

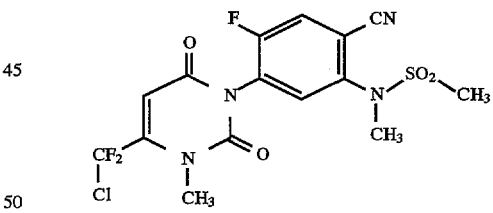

or a salt thereof.

26. A compound according to claim 1, wherein such compound is

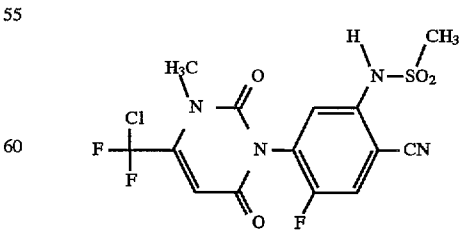

or a salt thereof.

27. A compound according to claim 1, wherein such compound is

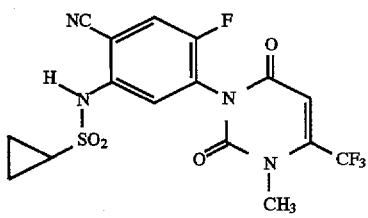

or a salt thereof.

28. A herbicidal composition comprising a herbicidally effective amount of a compound or salt thereof according to claim 1 and a diluent.

29. A method of combatting unwanted vegetation which comprises applying to such vegetation or to a locus from which it is desired to exclude such vegetation a herbicidally effective amount of a compound or salt thereof according to claim 1.

30. A method of combatting unwanted vegetation which comprises applying to such vegetation or to a locus from which it is desired to exclude such vegetation a herbicidally effective amount of a compound or salt thereof according to claim 3.

31. In the cultivation of wheat, corn or soy beans, wherein there is applied to the crop or to the field a selective herbicide for killing or preventing growth of unwanted vegetation but not of said crop, the improvement wherein said selective herbicide comprises a compound or salt thereof according to claim 1.

32. In the cultivation of wheat, corn or soy beans, wherein there is applied to the crop or to the field a selective herbicide for killing or preventing growth of unwanted vegetation but not of said crop, the improvement wherein said selective herbicide comprises a compound or salt thereof according to claim 3.

* * * * *